United States Patent
Poehlmann-Martins et al.

(10) Patent No.: US 12,303,719 B2
(45) Date of Patent: May 20, 2025

(54) MOVABLE/REPLACEABLE HIGH INTENSITY TARGET AND MULTIPLE ACCELERATOR SYSTEMS AND METHODS

(71) Applicant: Varian Medical Systems, Inc., Palo Alto, CA (US)

(72) Inventors: Flavio Poehlmann-Martins, Fremont, CA (US); William Thompson Main, Mariposa, CA (US); Amir Shojaei, Palo Alto, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 282 days.

(21) Appl. No.: 17/404,885

(22) Filed: Aug. 17, 2021

(65) Prior Publication Data
US 2023/0065037 A1 Mar. 2, 2023

(51) Int. Cl.
*A61N 5/10* (2006.01)
(52) U.S. Cl.
CPC ......... *A61N 5/1077* (2013.01); *A61N 5/1001* (2013.01); *A61N 5/1045* (2013.01);
(Continued)
(58) Field of Classification Search
None
See application file for complete search history.

(56) References Cited

U.S. PATENT DOCUMENTS

| | | | |
|---|---|---|---|
| 3,825,786 A | 7/1974 | Einighammer et al. | |
| 5,222,114 A | 6/1993 | Kamata et al. | |

(Continued)

FOREIGN PATENT DOCUMENTS

| | | |
|---|---|---|
| CN | 1185981 | 7/1998 |
| DE | 102010035650 | 3/2012 |

(Continued)

OTHER PUBLICATIONS

Sharma Anil Kumar et al: "Doslmetric Accuracy of a Dual Photon Energy Linac at Low Monitor Setting for Various Pulse Repetition Frequencies", Medical Dosimetry, vol. 19, No. 1, Apr. 1, 1994, pp. 47-49.

(Continued)

*Primary Examiner* — Marcus H Taningco
(74) *Attorney, Agent, or Firm* — Harness, Dickey & Pierce, P.L.C.

(57) ABSTRACT

Presented systems and methods facilitate efficient and effective generation and delivery of radiation. In one embodiment, a radiation generation component includes a high intensity target that produces Bremsstrahlung radiation in response to impacts by charged particles, wherein the high intensity target is configured with operating limitations based primarily on catastrophic failure mechanisms rather than fatigue failure mechanisms. The high intensity target is configured to be compatible with a loading system of a radiation generation system. The high intensity target can have a catastrophic failure strain percentage in the range of 0.5 to 4.0 percent. The catastrophic failure mechanisms can include at least one selected from the group comprising ultimate tensile strength, fracture strain, and melting point. The high intensity target can have a product life in a low cycle fatigue regime range. The high intensity target can comprise a material with a melting temperature in the range of 800 C. to 3,700 C. The high intensity target can be configured to load in an accelerator enclosure. The high intensity target can include an identification feature. The Bremsstrahlung radiation can correspond to average dose rates greater than 1.0 greys per second (Gy/s).

13 Claims, 54 Drawing Sheets

(52) U.S. Cl.
CPC ...... *A61N 5/1048* (2013.01); *A61N 2005/101* (2013.01); *A61N 2005/1019* (2013.01); *A61N 2005/1089* (2013.01)

(56) References Cited

U.S. PATENT DOCUMENTS

| | | | |
|---|---|---|---|
| 6,463,123 | B1 | 10/2002 | Korenev |
| 10,806,950 | B2 | 10/2020 | Fahrig et al. |
| 2002/0101958 | A1* | 8/2002 | Bertsche ................ H01J 35/13 378/65 |
| 2010/0034352 | A1* | 2/2010 | Aoi ...................... A61N 5/1048 378/65 |
| 2011/0235781 | A1 | 9/2011 | Aoki et al. |
| 2013/0121462 | A1* | 5/2013 | Kim ........................ H01J 35/06 378/138 |
| 2015/0092924 | A1* | 4/2015 | Yun ...................... H01J 35/105 378/143 |
| 2016/0247655 | A1 | 8/2016 | Niemann et al. |
| 2018/0075998 | A1 | 3/2018 | Raber et al. |
| 2018/0247786 | A1 | 8/2018 | Liang et al. |
| 2020/0113038 | A1 | 4/2020 | Mishin |
| 2022/0305292 | A1* | 9/2022 | Harper ................. A61N 5/1081 |

FOREIGN PATENT DOCUMENTS

| | | |
|---|---|---|
| JP | S63270066 | 11/1988 |
| RU | 2608189 | 1/2017 |
| WO | 2013185826 | 12/2013 |
| WO | 2021061666 | 4/2021 |
| WO | 2021113323 A9 | 7/2021 |
| WO | 2021149888 | 7/2021 |

\* cited by examiner

3500
High Intensity Target

| 3521 Impact Location | 3522 Impact Location | 3523 Impact Location | 3524 Impact Location |
|---|---|---|---|
| 3525 Impact Location | 3526 Impact Location | 3527 Impact Location | 3528 Impact Location |

| 3531 Impact Location | 3532 Impact Location | 3533 Impact Location | 3534 Impact Location |
|---|---|---|---|
| 3535 Impact Location | 3536 Impact Location | 3537 Impact Location | 3538 Impact Location |

| 3541 Impact Location | 3542 Impact Location | 3543 Impact Location | 3544 Impact Location |
|---|---|---|---|
| 3545 Impact Location | 3546 Impact Location | 3547 Impact Location | 3548 Impact Location |

Fig. 4

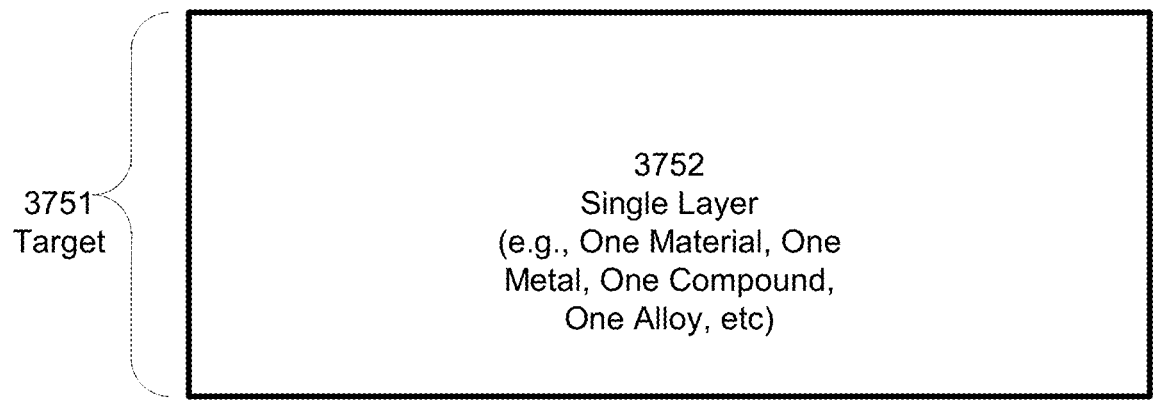
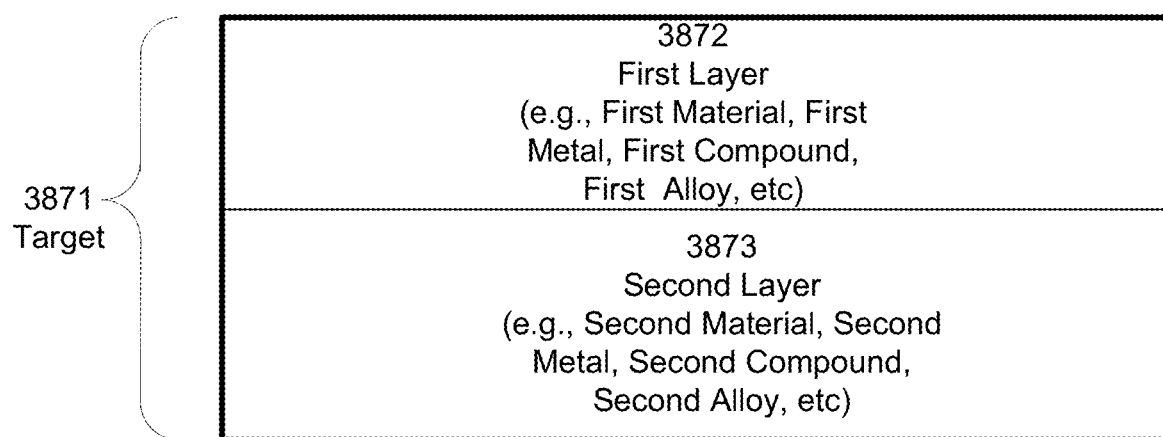
Fig. 6

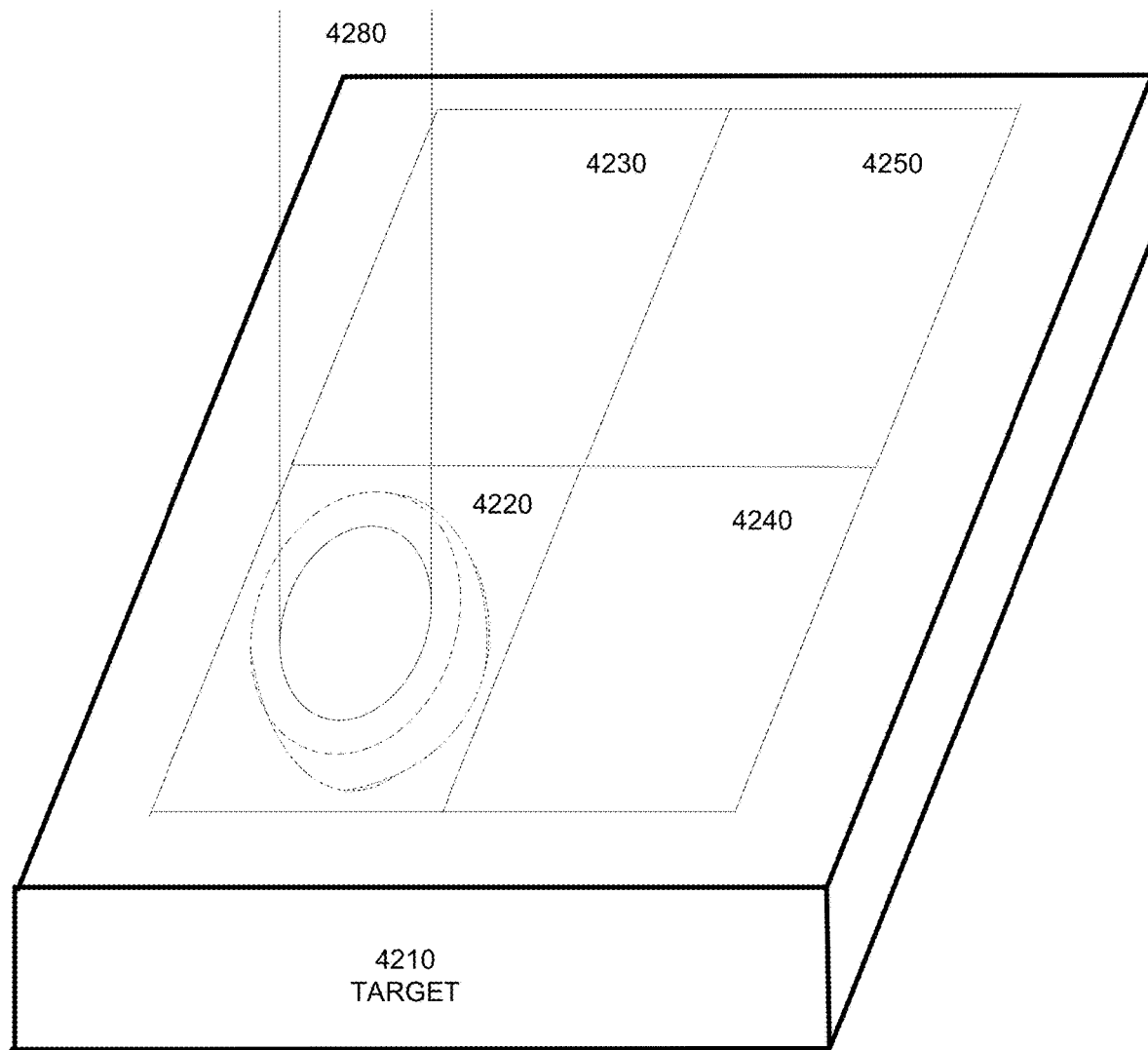
4271
Uniaxial Linear
Motion
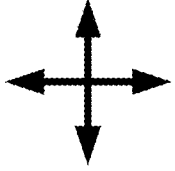
4272
Multi-Stage
Motion
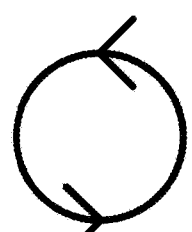
4273
Rotating Motion
Fig. 11

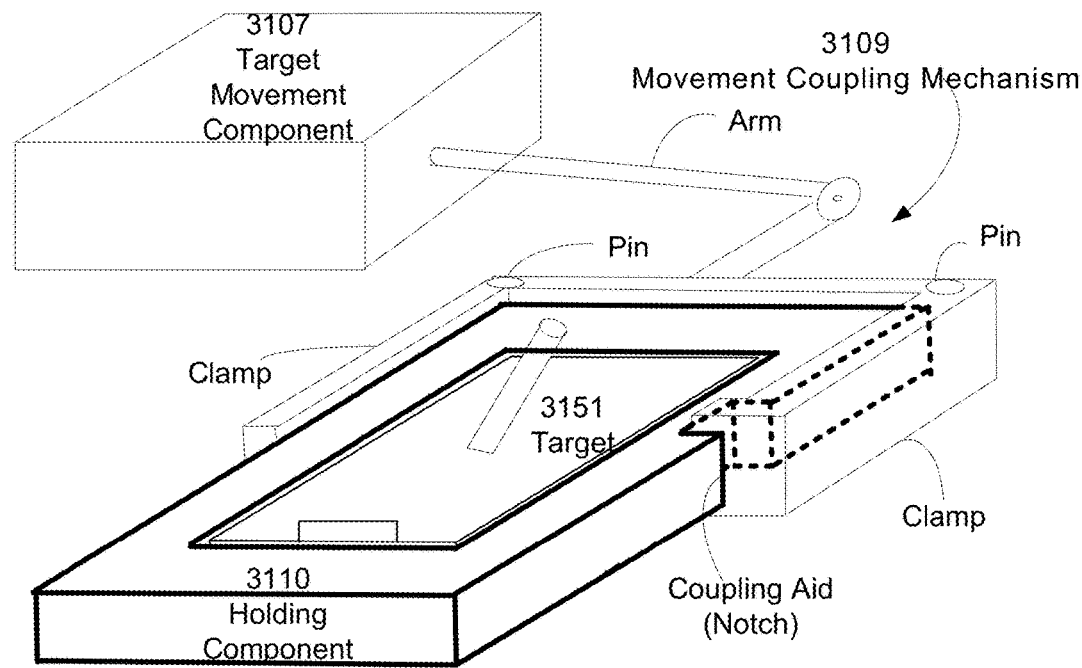
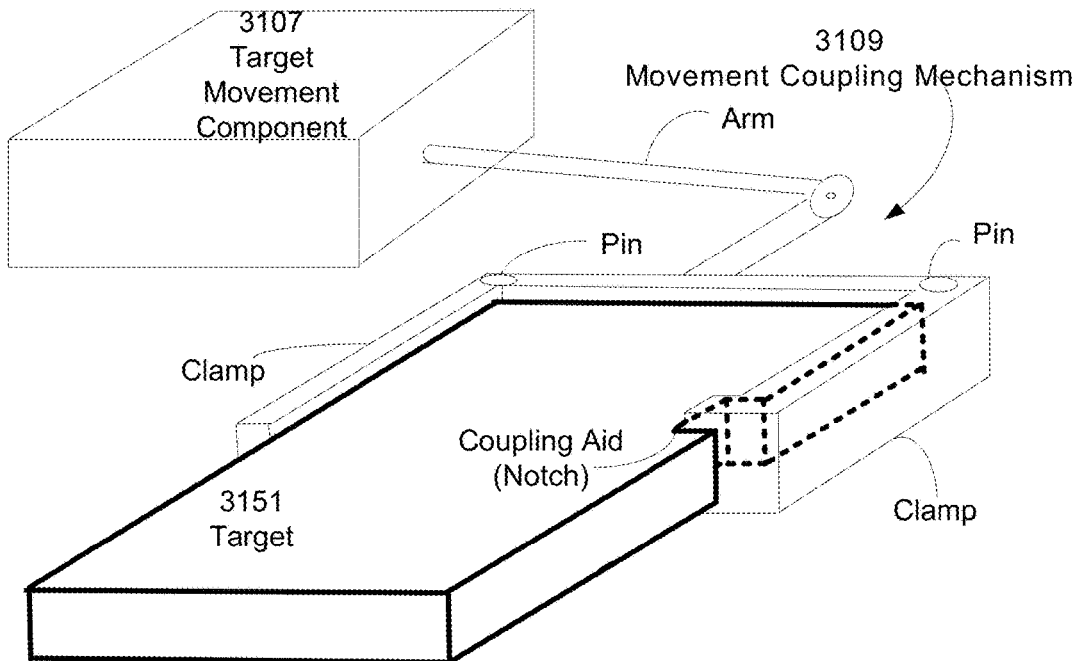
Fig. 16

4700

```
4710
Generating a charged particle.
```

```
4720
Accelerating the charged particle.
```

```
4730
Generating radiation in response to impact by the charged
particle on a high energy target.
```

```
4740
Changing an impact location of the charged particle on the
high energy target,
```

```
4740
Selectively inserting and removing the replaceable high
energy target to and from use.
```

Fig. 18

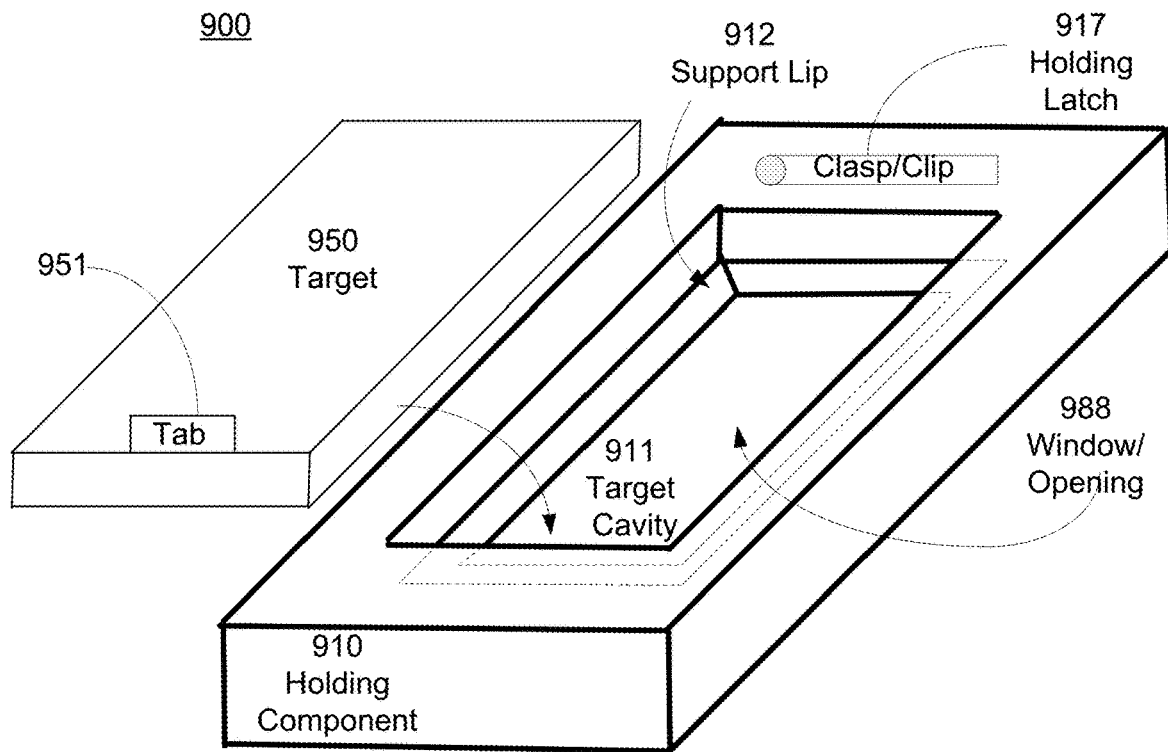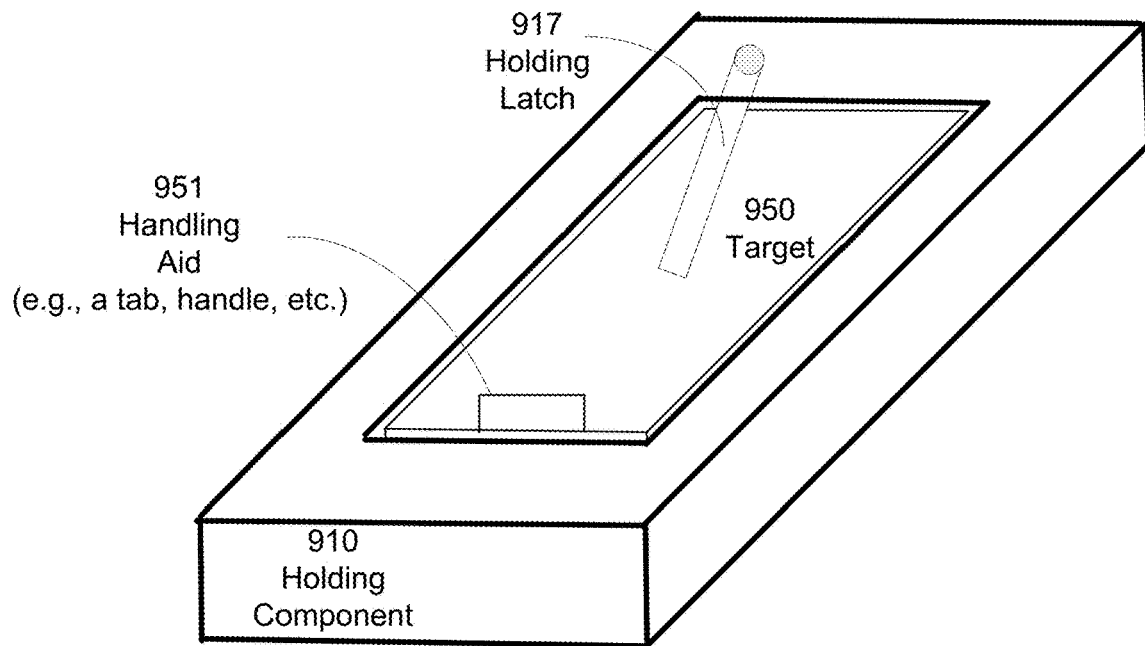
Fig. 20

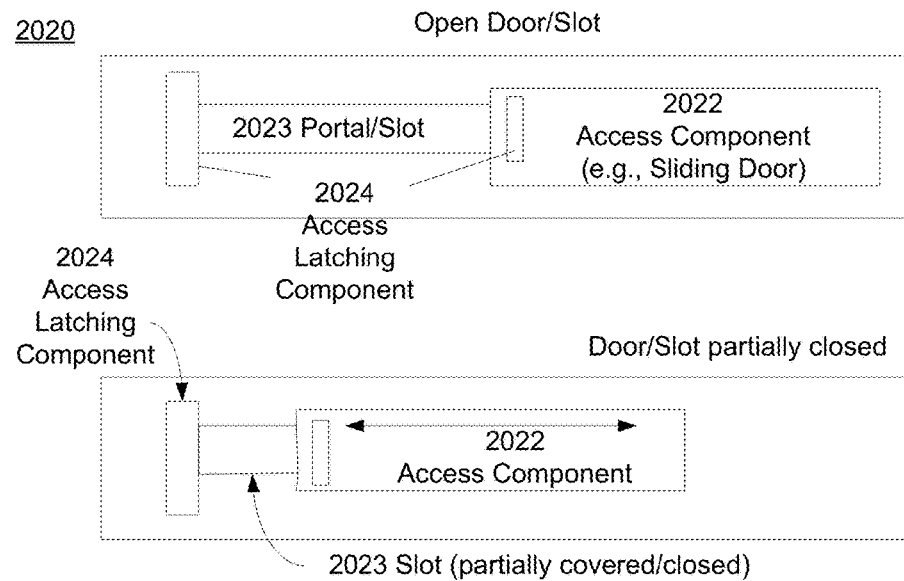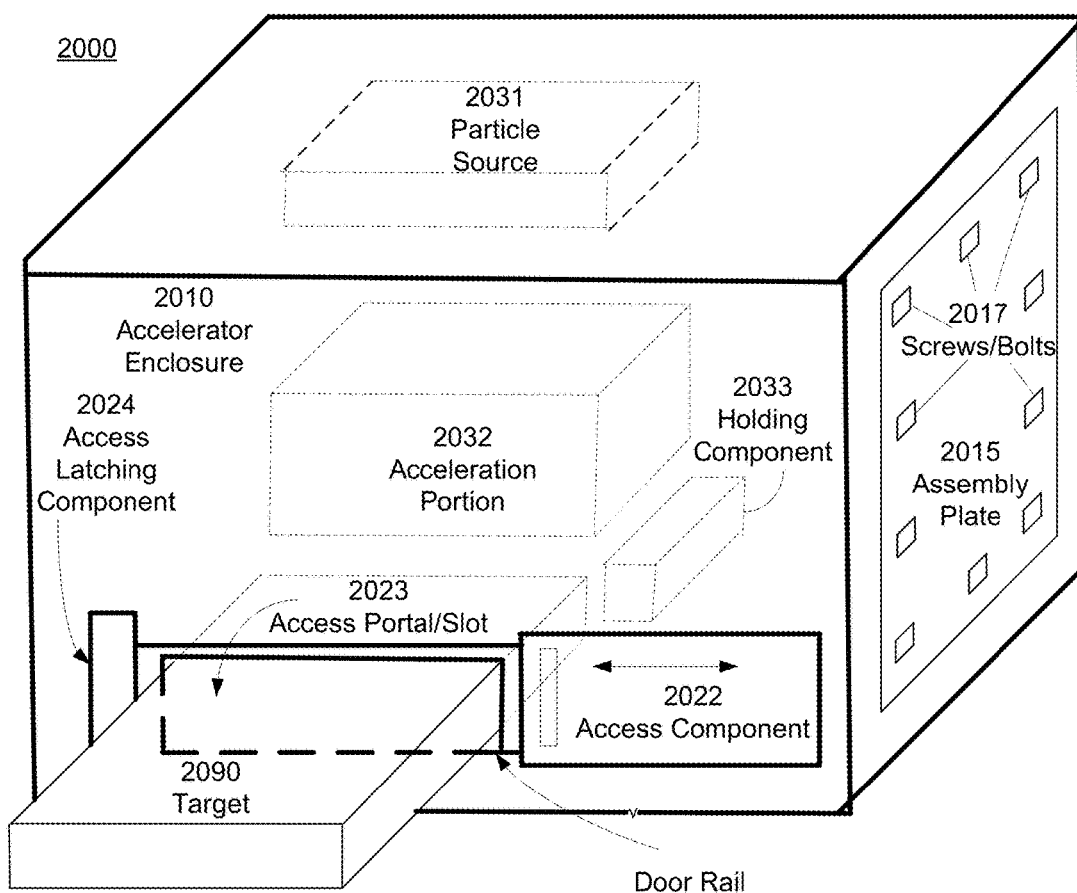
Fig. 23

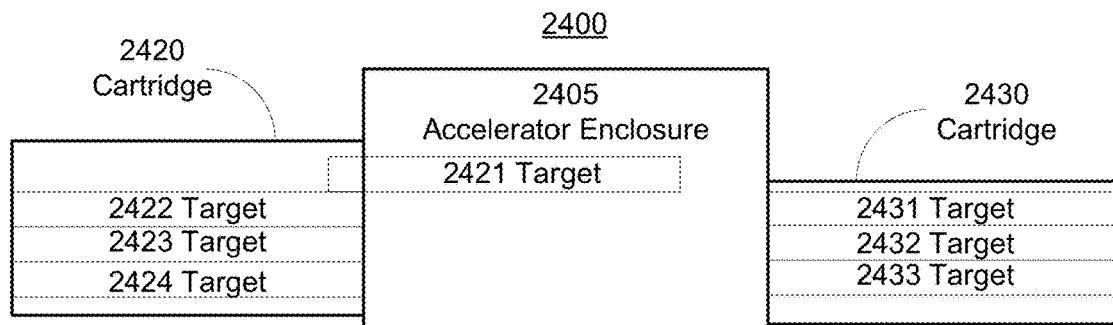
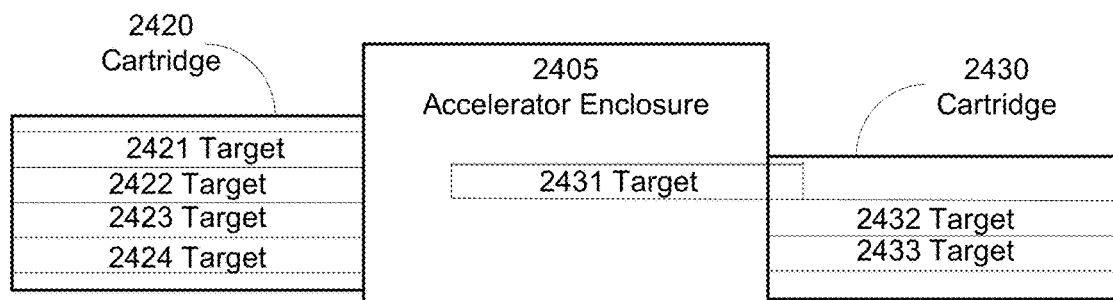
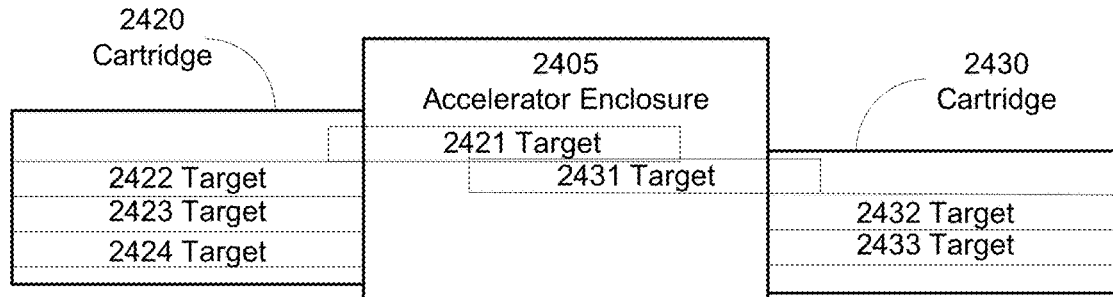
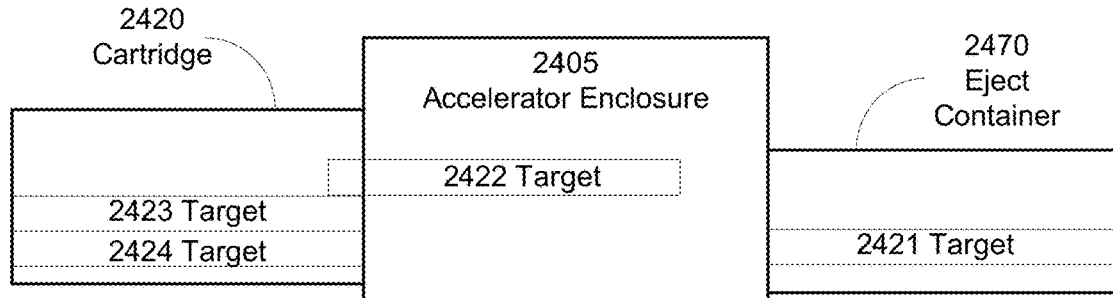
Fig. 40

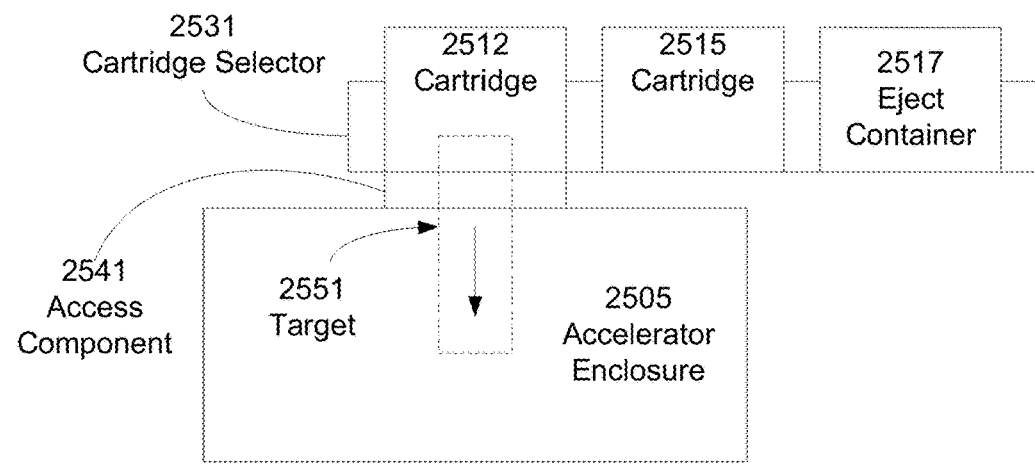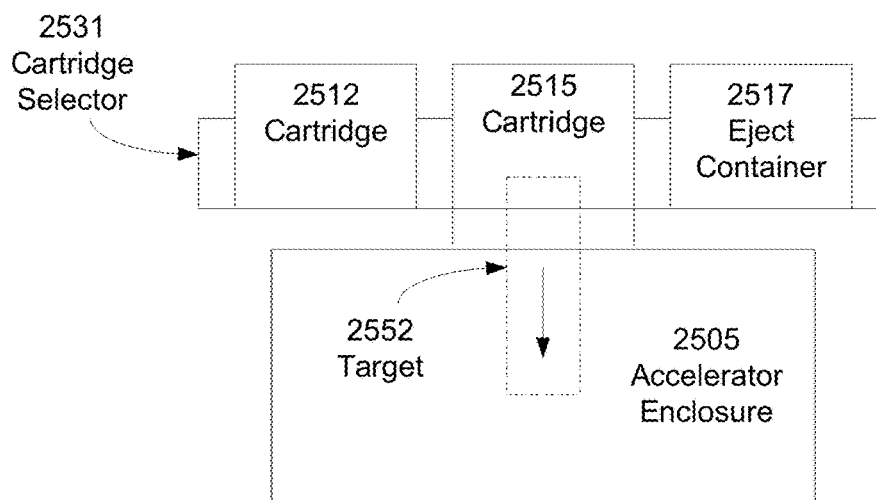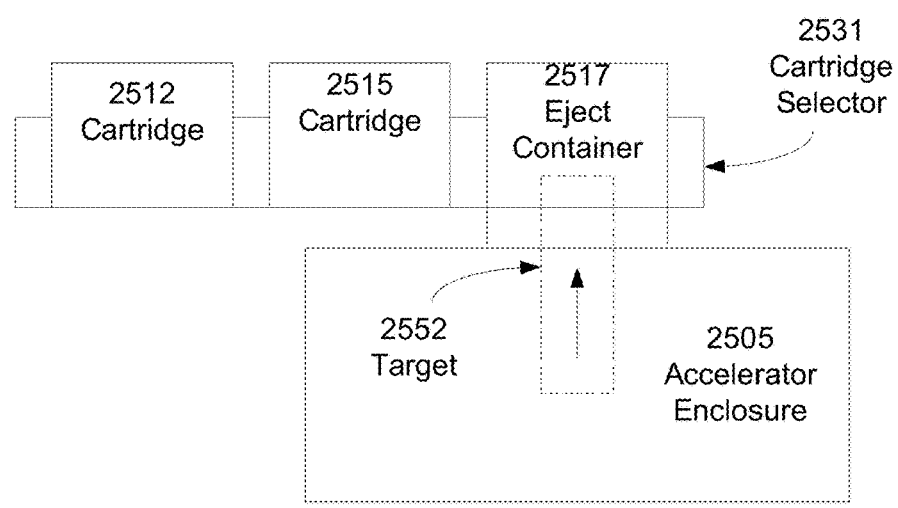
Fig. 41

2900

| 2910 |
| A magazine/cartridge is loaded with multiple replaceable high intensity targets. |

| 2920 |
| The cartridge is loaded in /coupled with a radiation/accelerator system. |

| 2930 |
| A cartridge selection process is performed. |

| 2940 |
| Access to a operational location is obtained. |

| 2950 |
| A replaceable high intensity target is inserted in the operational location. |

| 2960 |
| After a radiation operation is performed, access to the operational location is obtained again. |

| 2970 |
| The replaceable high intensity target is ejected from the operational location. |

| 2980 |
| The ejected replaceable high intensity target is removed from the radiation/accelerator system. |

MOVABLE/REPLACEABLE HIGH INTENSITY TARGET AND MULTIPLE ACCELERATOR SYSTEMS AND METHODS

FIELD OF THE INVENTION

The present invention relates to the field of radiation beam generation and control. In one embodiment, systems and methods facilitate fast and effective application of radiation therapy.

BACKGROUND

Radiation beams can be utilized in a number of different applications and accurately applying an appropriate amount of radiation can be very important. Radiation beam therapy typically includes directing a radiation beam at an area of tissue. There can be various different types of radiation beams (e.g., photon, ionizing particle, etc.). The radiation beams are typically used to stop the growth or spread of the targeted tissue cells by killing them or degrading their cell division ability. While radiation therapy is generally considered beneficial, there can be a number of potential side effects. The side effects can include unintended damage to DNA of healthy tissue cells. The effectiveness of radiation therapy is primarily a function of the dose or amount of ionizing radiation that is applied to cancerous cells while avoiding impacts to healthy cells.

The amount of radiation that is applied to the tissue is typically a function of a dose rate and time the targeted tissue is exposed to the radiation. In some implementations, the dose rate corresponds to the "current" of charged particles used to generate the radiation. The charged particle (e.g., proton, electron, etc.) can be directed at the tissue or can be directed at an intermediate target (e.g., Xray target, etc.) that produces another fundamental or elementary particle (e.g., photons, neutrons, etc.,) which are directed at the tissue. The elementary particles can have radiation characteristics (e.g., X-ray wavelength, ionizing capabilities, etc.). Higher dose rates usually enable shorter exposure times and that can have a number of benefits, including less opportunity for extraneous events to influence the therapy, increased productivity, and greater convenience to the patient.

Various treatment approaches have characteristics that can offer significant benefits. It was recently discovered that delivering a therapeutic dose at ultra high dose rates (>40 Gy/s), referred to as FLASH dose rate delivery, reduces the radiation sensitivity of healthy tissue, but not of tumors. Delivering the same dose, but at ultra-high dose rates can increase the therapeutic ratio over conventional treatment delivery. Proton and electron radiation approaches can provide higher dose rates. Some conventional approaches have attempted to overcome traditional dose limitations by increasing the dose rate through higher MeV values. To be effective in some scenarios (e.g., treating human tissue, etc.) electron and proton radiation approaches require very high beam energies in excess of 100 MeV and therefore require large and expensive systems. However, conventional Xray target systems are typically limited in their ability to participate in/perform with various treatment approaches that offer significant benefits, for example, FLASH dose delivery. Conventional photon radiation approaches typically have a number of practical issues and obstacles that significantly limit and prevent them from being useful in higher dose applications (e.g., human medical applications, etc.). Developing systems and methods compatible with higher MeV values can be difficult and problematic for conventional Xray target approaches.

One considerable conventional obstacle to higher dose rates in photon radiation approaches is avoiding problematic conditions (e.g., overheating, thermal cycle stresses, cycle fatigue, etc.). Heat loading capabilities of traditional Xray targets (e.g., used in incident electron beam deceleration, used in production of Bremsstrahlung radiation, etc.) do not typically provide adequate heat removal at high power densities (e.g., power into the target, etc.) and the targets begin to lose performance characteristics. Heating impacts can be particularly detrimental in pulse and cycle-based radiation system applications. Xray targets typically experience expansion stresses associated with increased heat when a pulse/cycle is in an on/high stage and contraction stresses associated with decreased heat when the pulse/cycle is in an off/low stage. The repeated expansion/contraction and internal stresses/strains can result in structural fatigue and failure. For long-lifetime stationary targets, the acceptable power for a target is often limited by this cyclical fatigue rather than by melting temperatures of target materials or thermal shock (e.g., low cycle failure, instant failure, etc.). Because conventional targets cannot typically handle the power required to obtain FLASH dose rates, traditional FLASH delivery has mainly focused on using protons or electrons.

Traditional FLASH delivery also mainly focused on using protons or electrons because FLASH therapy appears to require a threshold dose before the FLASH effect materializes and also requires that the entire dose is delivered within a very small time window. In conventional state of the art treatment plans, such as in arc therapy or intensity modulated radiation therapy, the therapeutic dose is delivered to the tumor from many different angles and therefore most healthy tissue never reaches the threshold dose at which FLASH dose rates would be beneficial. For FLASH treatments to improve on state-of-the art delivery it therefore also would need to deliver dose from multiple angles and it would have to do that near-simultaneously. Conventional proton and electron systems are typically too expensive to implement multiple accelerators supplying simultaneous beams from multiple angles. Conventional gantry approaches are also usually too slow moving between delivery angles to satisfy the FLASH timings limitations.

If traditional limitations on target power handling capability and delivery from different angles can be overcome, then X-ray FLASH offers several advantages over electron or ion FLASH.

SUMMARY

Presented systems and methods facilitate efficient and effective generation and delivery of radiation. In one embodiment, a radiation generation component includes a high intensity target that produces Bremsstrahlung radiation in response to impacts by charged particles, wherein the high intensity target is configured with operating limitations based primarily on catastrophic failure mechanisms rather than fatigue failure mechanisms. The high intensity target is configured to be compatible with a loading system of a radiation generation system. The high intensity target can have a catastrophic failure strain percentage in the range of 0.5 to 4.0 percent. The catastrophic failure mechanisms can include at least one selected from the group comprising ultimate tensile strength, fracture strain, and melting point. The high intensity target can have a product life in a low cycle fatigue regime range. The high intensity target can comprise a material with a melting temperature in the range of 800 C. to 3,700 C. The high intensity target can be configured to load in an accelerator enclosure. The high intensity target can include an identification feature. The Bremsstrahlung radiation can correspond to average dose rates greater than 1.0 greys per second (Gy/s).

In one embodiment, the consumable radiation generation component includes a first bremsstrahlung radiation zone, a second bremsstrahlung radiation zone, and a third zone of the high intensity target. The first bremsstrahlung radiation zone can generate radiation in response to impacts by a first set of charged particles included in a first set of pulses in an electron beam. The second bremsstrahlung radiation zone of the high intensity target can generate radiation in response to impacts by a second set of charged particles included in a second set of pulses in an electron beam. The third zone can be located between the first bremsstrahlung radiation zone and the second bremsstrahlung radiation zone; wherein the third zone is configured to mitigate detrimental effects associated with the impacts of the first set of charged particles on the second bremsstrahlung radiation zone. The third zone can prevent heat diffusion from the first bremsstrahlung radiation zone reaching the second bremsstrahlung radiation zone before the impacts of the second set of charged particles in the second bremsstrahlung radiation zone.

In one embodiment, the high intensity target can be configured similar to respective ones in a plurality of high intensity targets, wherein a respective first one of the plurality of the high intensity targets is configured to be unloaded from an accelerator system in under 30 minutes and a respective second one of the plurality of high intensity targets is configured to be loaded into an accelerator system in under 30 minutes. The high intensity target can be a multilayer structure and at least two of the layers include different materials. The high intensity target can be a monolithic structure comprising at least 80 percent of one metal by atomic weight. The high intensity target can include at least one material selected from the group consisting of copper, tungsten, and steel.

In one embodiment, a radiation generation component includes a plurality of high intensity targets, and a cartridge that holds the plurality of high intensity targets, wherein the cartridge is configured to feed the plurality of high intensity targets into a radiation generation system. In one exemplary implementation, the cartridge automatically feeds the plurality of high intensity targets into a radiation generation system. The cartridge can automatically feed the plurality of high intensity targets into a radiation generation system one at a time. The cartridge can automatically feed the plurality of high intensity targets into a radiation generation system so that more than one of the plurality of high intensity targets is utilized by the radiation generation system at the same time. The cartridge can automatically feed one of the plurality of high intensity targets into the radiation generation system in response to a trigger. The trigger can be associated with an indication that another one of the plurality of high intensity targets is ready to be replaced. A first one of the plurality of high intensity targets can have a first set of characteristics and a second one of the plurality of high intensity targets can have a second set of characteristics. The respective ones of the high intensity target can be configured to be inserted into an operational location from the cartridge in under 2 minutes and ejected from the operational location. The cartridge can be configured to load into the radiation system in under 30 minutes and unload from the radiation system in under 30 minutes.

BRIEF DESCRIPTION OF THE DRAWINGS

The accompanying drawings together with the description are incorporated in and form a part of this specification. They illustrate exemplary embodiments and explain exemplary principles of the disclosure. They are not intended to limit the present invention to the particular embodiments illustrated therein. The drawings are not to scale unless otherwise specifically indicated.

FIG. 4 is a block diagram of particle beam impact locations on a high intensity target surface in accordance with one embodiment.

FIG. 6 is a block diagram of exemplary configurations of high intensity targets in accordance with one embodiment.

FIG. 11 is a block diagram of exemplary particle impact adjustment motions or patterns in accordance with one embodiment.

FIG. 16 is a block diagram of an exemplary target movement system in a first configuration and second configuration in accordance with one embodiment.

FIG. 18 is a flow chart of an example high intensity target method in accordance with one embodiment.

FIG. 20 is a block diagram of an exemplary holding system in accordance with one embodiment.

FIG. 23 is block diagram of an exemplary multiple access system in accordance with one embodiment.

FIG. 40 is a block diagram of an exemplary multiple cartridge system in accordance with one embodiment.

FIG. 41 is a block diagram of another exemplary multiple cartridge system in accordance with one embodiment.

FIG. 42 is a flow chart of a high intensity target loading/unloading method/process in accordance with one embodiment.

DETAILED DESCRIPTION OF THE INVENTION

Figure 1:
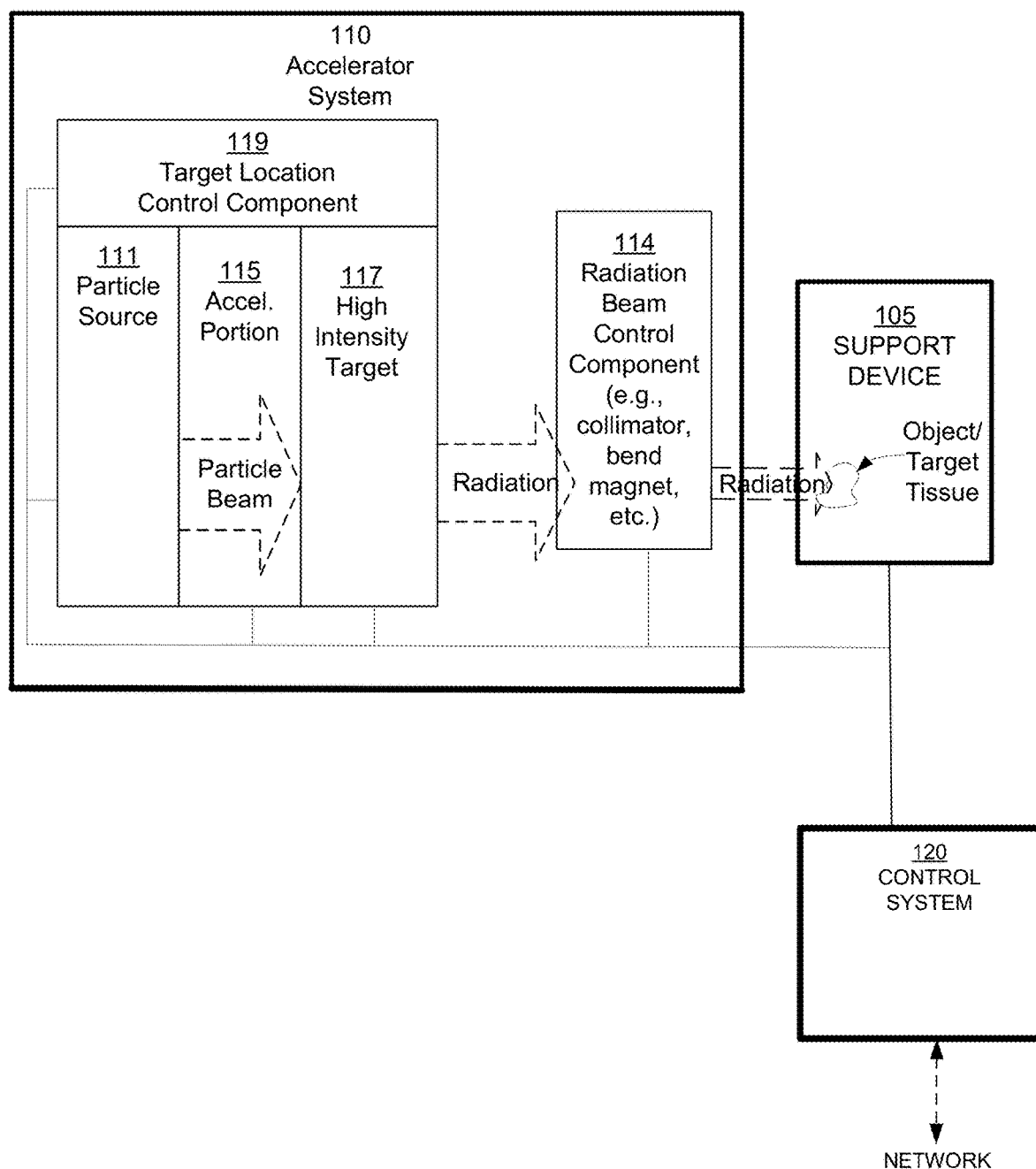
FIG. 1 is a block diagram of an exemplary radiation therapy system in accordance with an embodiment.

Reference will now be made in detail to the illustrated, exemplary embodiments in the accompanying drawings. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one ordinarily skilled in the art that the present invention may be practiced without these specific details. In other instances, well known methods, procedures, components, and circuits have not been described in detail as not to unnecessarily obscure aspects of the current invention.

Presented systems and methods facilitate efficient and effective radiation generation and control. High intensity target systems and methods are capable of operating with high energy beams. In one embodiment, high intensity target systems and methods produce Bremsstrahlung generated radiation capable of delivering more than the traditional photon system dose rate of less than 1 Gy/s. In one exemplary implementation, high intensity target systems and methods produce Bremsstrahlung generated radiation capable of delivering FLASH dose rates (e.g., greater than or equal to 40 Gy/s, etc.).

It is appreciated that high intensity target systems and methods include various features/configurations that enable delivery of dose rates greater than or equal to 1 Gy/s, and overcome issues and limitations of conventional approaches. The features/configurations can include movable target characteristics, replaceable target characteristics, adjustable source axis distance SAD, and coordinated utilization of multiple accelerators. While explanation of the various configurations/features may appear to be presented individually in the following detailed description, it is appreciated that a system and method can include one or a combination of more than one of these characteristics and features.

A high intensity target can be configured to be compatible with changes/movement of charged particle impact locations on the high intensity target. In one embodiment, a high intensity target is moveable (e.g., within an accelerator, etc.) causing the charged particle impact location to move/change. In one exemplary implementation, movement of the charged particle impact location is based on thermal diffusion and is moved at a rate greater than diffusion of detrimental heat impacts on the high intensity target. In one embodiment, detrimental heat impacts are ones that rise to a level of unacceptably interfering with reliable radiation generation and delivery. In one exemplary implementation, heat impacts can cause localized damage in a high intensity target, but high intensity target system and method features and characteristics (e.g., moveable target, replaceable target, etc.) can mitigate or prevent the heat impacts and localized damage from reaching a detrimental level that adversely affects radiation delivery. Additional explanation of charged particle impact locations and high intensity target movement is presented in other portions of this detailed description.

A high intensity target can be configured to be removable. In one embodiment, a high intensity target is easily loaded to and unloaded from an accelerator system. In one embodiment, a high intensity target can be configured for use with a loading system/mechanism that loads/unloads a high intensity target. In one exemplary implementation, a cartridge/magazine with a plurality of high intensity targets can be loaded to and unloaded from an accelerator system. Additional explanation of removable high intensity targets is presented in other portions of this detailed description.

High intensity target systems and methods can be compatible with source axis distance (SAD) adjustments. Additional explanation of SAD adjustments is presented in other portions of this detailed description.

In one embodiment, multiple accelerator systems are utilized to deliver doses from different orientations or angles. The delivery can be simultaneous or substantially at the same time. In one embodiment, simultaneously or substantially simultaneous means multiple things existing or occurring in less than or equal to one second of one another. In one embodiment simultaneously or substantially simultaneous means less than or equal to one milli-second. The multiple accelerator systems can be implemented in various configurations. The number of accelerator systems and differences in radiation beam application angles can vary. In one embodiment, a microwave generation system can power multiple independent accelerator systems. In one exemplary implementation, a microwave generation system can power a plurality of independent accelerator systems via a plurality of independent RF chains, in which separate ones of the plurality of independent accelerator systems are powered by a separate respective one of a plurality of separate RF systems included (e.g., bunched together, etc.) in the microwave generation system. Additional explanation of multiple accelerator systems is presented in other portions of this detailed description.

High Intensity Target Accelerator Systems and Methods

FIG. 1 is a block diagram of an exemplary radiation therapy system 100 in accordance with an embodiment. Radiation therapy system 100 includes an accelerator system 110, radiation beam control component 114 (e.g., collimator, bend magnet, etc.), control system 120, and support device 105. In one exemplary implementation, the accelerator system 110 generates particles (e.g., photons, etc.) that have radiation characteristics. In one embodiment, elementary particles travel in substantially the same direction and are included in a radiation beam. In one exemplary implementation, the radiation beam includes X-rays. The system is compatible with a variety of accelerator systems (e.g., a continuous wave beam accelerator, bevatron, an isochronous cyclotron, a pulsed accelerator, a synchrocyclotron, a synchrotron, etc.). In one embodiment, accelerator system 110 is considered a linear accelerator (LINAC) configuration. In one exemplary implementation, the accelerator system 110 is capable of relatively continuous wave output and extracts particles with a specified energy. In one exemplary implementation, the accelerator is pulsed.

Accelerator system 110 includes particle source 111, acceleration portion 115, high intensity target 117, and target location control component 119. Particle source 111 can generate a particle beam (e.g., electron beam, etc.). In one embodiment, particle source 111 is compatible with particle acceleration using electromagnetic waves in the microwave frequency range. The acceleration portion 115 allows particles (e.g., electrons, protons, photons, etc.) emitted by the particle source 111 to travel to the high intensity target 117. The acceleration portion 115 can accelerate the particles. It is appreciated the acceleration portion can have various configurations (e.g., drift tube, acceleration channel, waveguide, etc.) In one exemplary implementation, the acceleration portion can also control the direction of the particles. The accelerator system 110 can include various other components (e.g., dipole magnets, bending magnets, solenoid magnets, steering magnets, etc.) that direct (e.g., bend, steer, guide, etc.) resulting radiation beam or x-rays through the system in a direction toward and through the radiation control component 114. The accelerator system 110 may also include components that are used to adjust the beam energy.

In one embodiment, the particle source 111 generates a beam of electron particles that are accelerated by acceleration portion 115 towards high intensity target 117. When the electron particles collide with high intensity target 117 a secondary photon Bremsstrahlung radiation beam is created. In one exemplary implementation, the high intensity target generates radiation in the form of X-rays. High intensity target 117 can receive high energy input (e.g., greater than 1 MeV, etc.) and generate a relatively high quantity of radiation while maintaining overall system integrity and radiation delivery performance (e.g., including handling stressful heat conditions, etc.). In one embodiment, a high intensity target can experience localized damage while other aspects of system integrity and radiation delivery performance are maintained. Additional description of high intensity target systems and methods ability to maintain reliable performance and accurate radiation delivery at high energy input levels is presented in later portions of this specification.

In one embodiment, radiation control component 114 includes components that control a radiation beam shape. In one exemplary implementation, radiation control component 114 can include a multi-leaf collimator (MLC) in which each MLC leaf can be independently adjusted (e.g., moved back-and-forth, etc.) to shape an aperture through which a beam can pass. The adjustments can be directed by control system 120. The aperture can block or not block portions of the radiation beam and thereby control beam shape and exposure time. The beam can be considered a relatively well-defined beam. The radiation control component 114 can be used to aim the beam toward various locations within an object (e.g., a patient, target tissue, etc.). In one embodiment, the radiation control component 114 controls a radiation beam in "X and Y directions" to scan a target tissue volume.

A target intended to receive the radiation (e.g., an object, a target tissue volume in a patient, etc.) can be located on the supporting device 105 (e.g., a chair, couch, bench, table, etc.) in a treatment room. In one embodiment, the accelerator system and the supporting device can be moved with respect to one another. The accelerator system and supporting device can have various configurations (e.g., fixed, movable arm, movable gantry, etc.).

In one embodiment, control system 120 receives and directs execution of a prescribed treatment plan. In one exemplary implementation, the control system 120 includes a computer system having a processor, memory, and user interface components (e.g., a keyboard, a mouse, a display, etc.). The control system 120 can control parameters and operations of the accelerator system 110 and supporting device 105, including parameters such as the energy, intensity, direction, size, shape of the beam, and so on. The control system 120 can receive data regarding operation of the system 100 and control the components according to data it receives. The data can be included in the prescribed treatment plan. In one embodiment, the control system 120 receives information and analyzes the performance and treatment being provided by radiation therapy system 100. In one embodiment, the control system 120 can direct adjustments to the radiation therapy system 100 based upon the analysis of dose and dose rate.

Figure 2A:
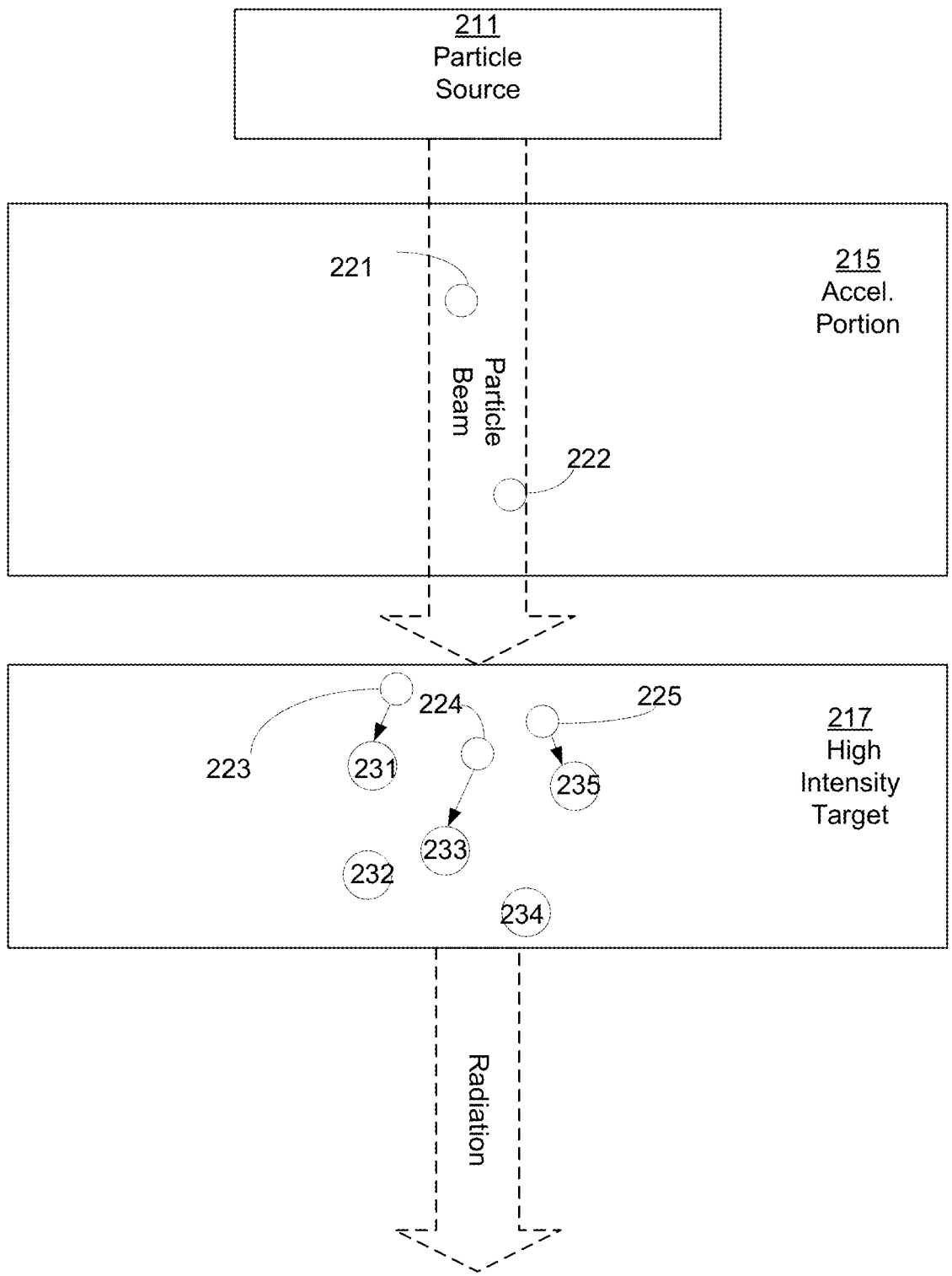
FIG. 2A is a block diagram of an exemplary accelerator system in accordance with one embodiment.

FIG. 2A is a block diagram of an exemplary accelerator system 200A in accordance with one embodiment. In one exemplary implementation, accelerator system 200A produces Bremsstrahlung radiation. Accelerator system 200A includes, particle source 211, accelerator portion 215, and high intensity target 217. Particle source 211, accelerator portion 215, and high intensity target 217 are similar to particle source 111, accelerator portion 115, and high intensity target 117. Particle source 211 generates charged particles (e.g., 221, 222, 223, 224, 225, etc.) that are accelerated by accelerator portion 215 towards high intensity target 217 when high intensity target 217 is in an operational location in an accelerator system. Additional explanation of an operational location is presented in other portions of this detailed description. High intensity target 217 includes particles (e.g., 231, 232, 233, 234, 235, etc.). The charged particles (e.g., 223, 224, 225, etc.) impact or collide with particles (e.g., 231, 233, 235, etc.) in the high intensity target 217. The impact/collision causes a deceleration or braking of the charged particles resulting in a loss of kinetic energy. In accordance with conservation of energy principles in physics, the resulting loss of kinetic energy is converted into a release of energy in the form of electromagnetic radiation (e.g., photons, etc.) and heat. The heat can cause temperatures in portions of the high intensity target to increase. The resulting radiation can be considered Bremsstrahlung radiation.

In one embodiment, an operational location is one in which high intensity target 217 can be impacted by electrons and resulting Bremsstrahlung radiation is released. An operational location can be configured to facilitate the release of the radiation in an intended manner while preventing release in an unintended manner. In one embodiment, an operational location is enclosed in manner that allows a radiation beam to exit in an intended manner while preventing release in an unintended manner. In one exemplary implementation, a high intensity target can be moved to different positions within an operational location so that an electron beam impacts different locations on a surface of the high intensity target. Additional explanation of operational locations, movement of a high intensity target to different positions within an operational location, operational locations within enclosures, and intended/unintended radiation release from an operational location is presented in other portions of this detailed description.

Figure 2B:
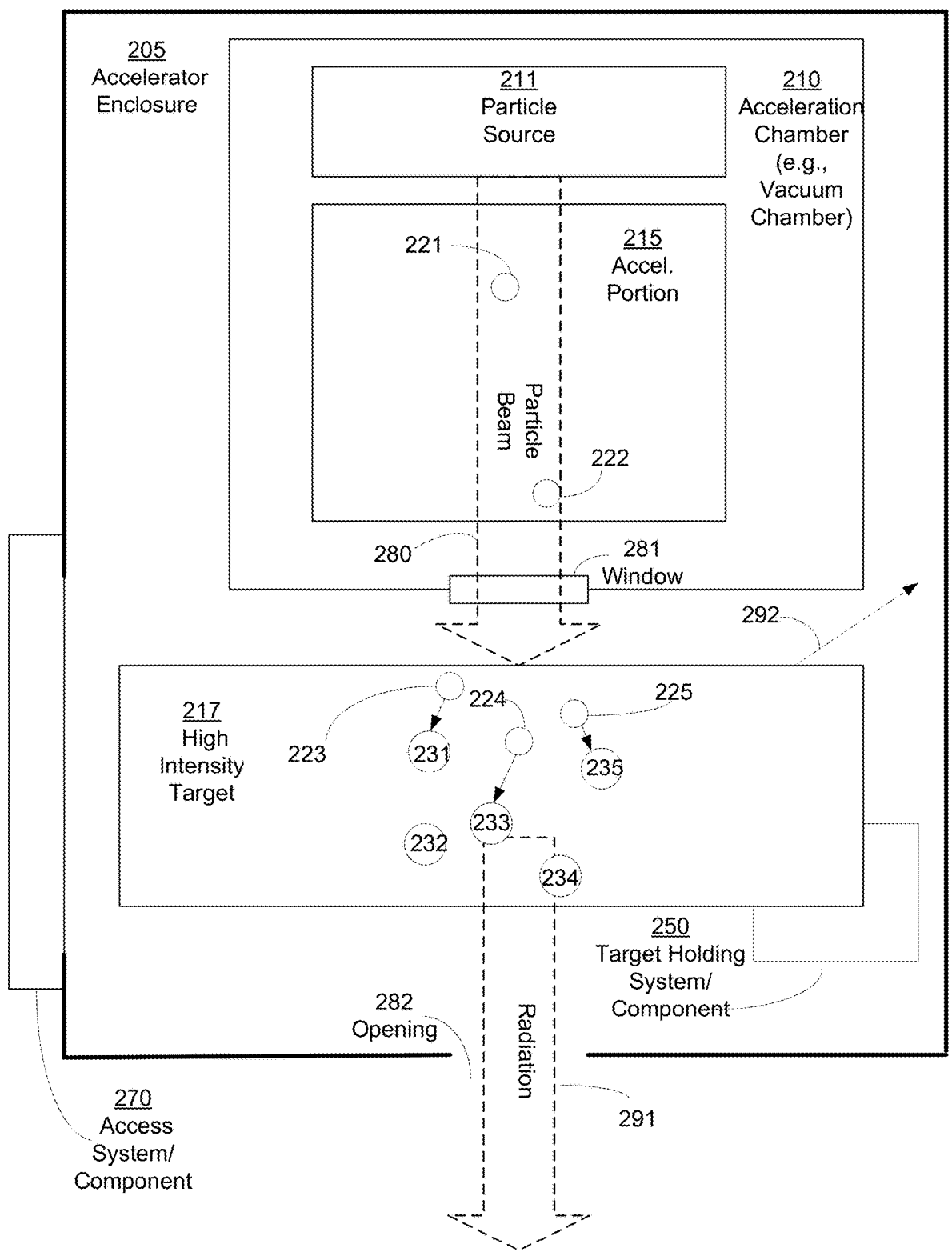
FIG. 2B is another block diagram of an exemplary accelerator system in accordance with one embodiment.

FIG. 2B is another block diagram of an exemplary accelerator system 200B in accordance with one embodiment. In one embodiment, accelerator system 200B is similar to accelerator system 200A in a different configuration. FIG. 2B shows additional features of accelerator system 200B that enable high intensity target 217 to be placed in an operational location within an accelerator system. FIG. 2B shows additional features of accelerator system 200B including accelerator enclosure 205, target holding system/component 250 and access system/component 270. In one embodiment, accelerator system 200B particle source 211 and acceleration portion 215 are included in vacuum/acceleration chamber 210. Target holding system/component 250 is configured to hold high intensity target 217 in an operational location within the accelerator enclosure 205. In one embodiment, holding system/component 250 also moves high intensity target 217 to various positions within the operational location so that an electron beam impacts different locations on a surface of the high intensity target 217. Access system/component 270 is configured to provide access to an operational location (e.g., within acceleration enclosure 205, etc.). Additional discussion on high intensity target loading and unloading is presented in other portions of this detail description section.

In one embodiment, accelerator enclosure 205 serves as a general enclosure for accelerator system 200B. In one exemplary implementation, accelerator enclosure 205 can be considered a treatment head enclosure. In one embodiment, an operational position for a high intensity target is located in the accelerator enclosure 205. In one exemplary implementation, accelerator enclosure 205, access system/component 270, and target holding system/component 250 can cooperatively operate to allow a radiation beam to exit in an intended manner (e.g., a radiation beam in direction 291, etc.) while preventing release in an unintended manner (e.g., in direction 292, etc.). In one embodiment, vacuum/acceleration chamber includes window 281 that allows electron beam 280 to pass through towards high intensity target 217 and accelerator enclosure 205 includes an opening 282 that allows radiation beam 291 to pass through (e.g., towards tissue target, tumor, etc.). Accelerator enclosure 205 can also act as a radiation shield against radiation transmission/leaking in other directions (e.g., direction 292, etc.). It is appreciated accelerator system 200B can include other components not shown in FIG. 2B. In one embodiment, accelerator system 200B can include a collimator (e.g., similar to collimator 2355 in FIG. 39, etc.) that acts as both a holding component and collimator that allows radiation to pass through the opening in the holding component/collimator while preventing radiation leaks in other directions.

Figure 2C:
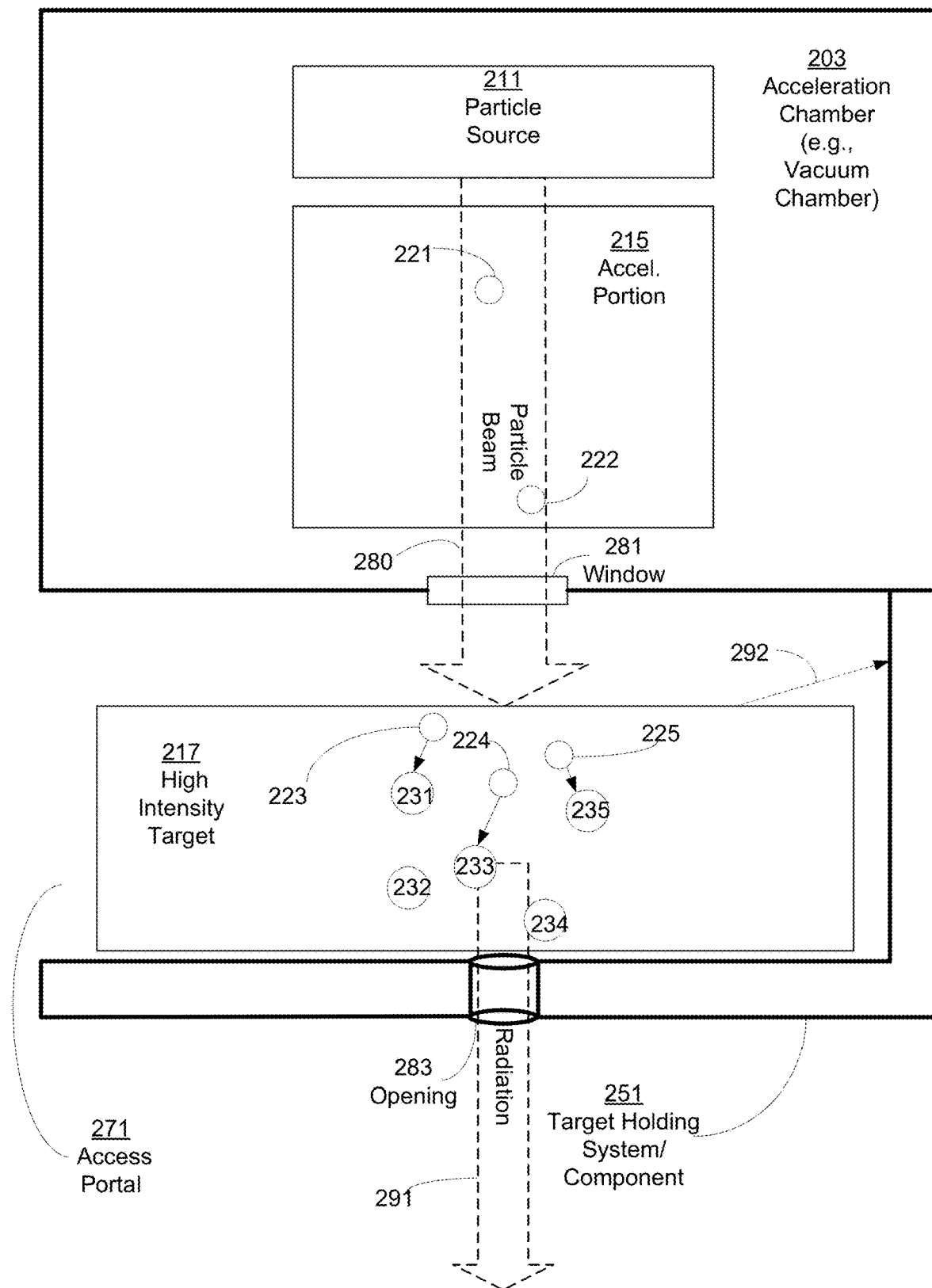
FIG. 2C is another block diagram of an exemplary accelerator system in accordance with one embodiment.

FIG. 2C is another block diagram of an exemplary accelerator system 200C accordance with one embodiment. In one embodiment, accelerator system 200C is similar to accelerator system 200A in a different configuration. FIG. 2C shows additional features of accelerator system 200C that enable high intensity target 217 to be placed in an operational location. FIG. 2C shows different features of accelerator system 200C including target holding system/component 251 and access portal 271. In one exemplary implementation, target holding system/component 251 can allow a radiation beam to exit in an intended manner (e.g., a radiation beam exit through opening 282 in direction 291, etc.) while preventing release in an unintended manner (e.g., in direction 293, etc.). In one exemplary implementation, target holding system/component 251 can act as both a holding component and collimator (e.g., similar to collimator 2355, etc.).

It is appreciated that an accelerator system can have various configurations. In one embodiment, a target can be inserted/ejected to and from an operational location in an acceleration/vacuum chamber (e.g., similar to acceleration chamber 210, etc.). In one exemplary, implementation, a target can be inserted/ejected to and from an operational location considered outside an accelerator enclosure. In one exemplary implementation, an operational location can be considered an open-air location.

Figure 3A:
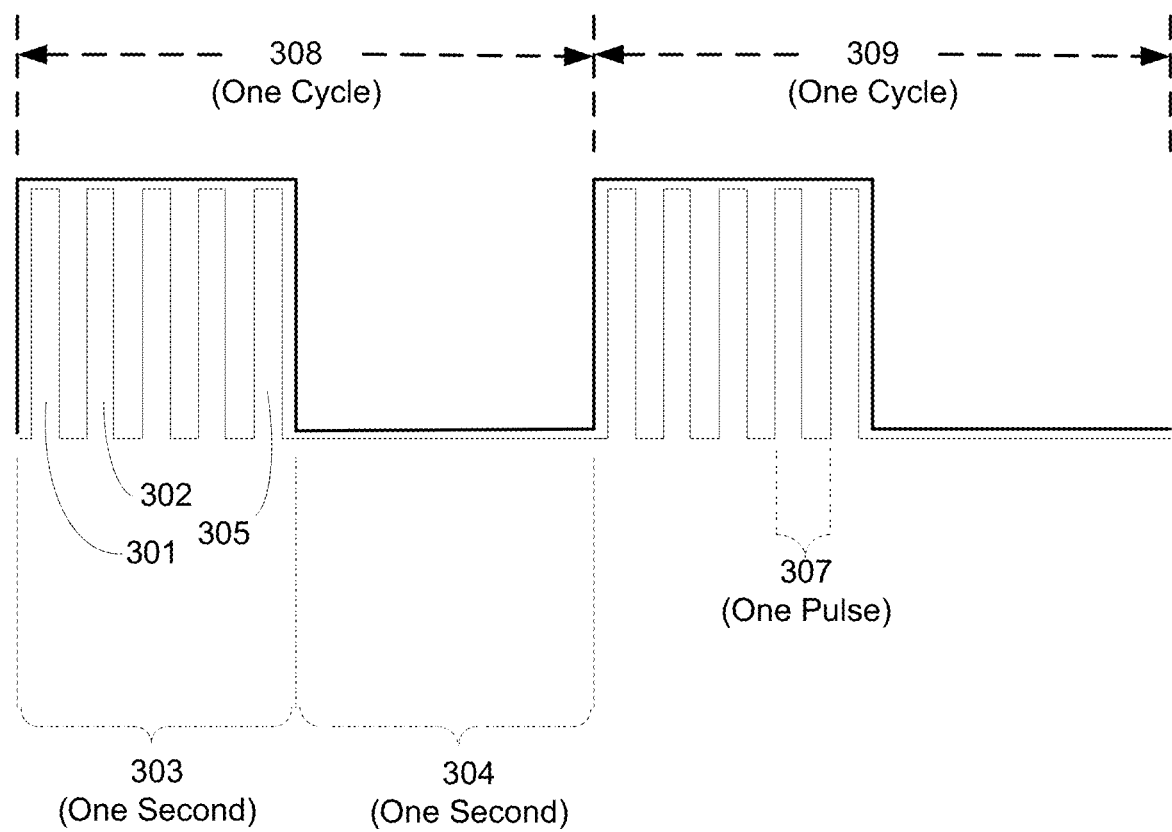
FIG. 3A is a block diagram of exemplary multiple pulses per cycle in accordance with one embodiment.

It is appreciated a high intensity target approach is compatible with various forms of radiation generation (e.g., characteristic radiation generation, reflection radiation generation, etc.). The radiation emissions can include X-rays. The radiation can include elementary particles (e.g., photons, ions, electrons, etc.) and radiation emissions can be configured in a beam. In one embodiment, electron beam energy is delivered to a high intensity target in power cycles of multiple pulses. FIG. 3A is a block diagram of exemplary multiple pulses per cycle in accordance with one embodiment. In one exemplary implementation, a pulse (e.g., 307 etc.) occurs when power is turned on and off multiple times per second (e.g., pluses 301, 302, 305, etc.). In one embodiment, pulses are delivered in cycles (e.g., 308, 309, etc.). A cycle can be considered to have an on phase and an off phase. In one embodiment, an on phase occurs when the power is delivered in multiple pulses (e.g., pluses 301, 302, 305, etc.) per second (e.g., second 303, etc.). In one embodiment, an off phase occurs when no pulses are delivered for at least one second (e.g., second 304, etc.). In one exemplary implementation, a power cycle starts when an electron beam hits a high intensity target and ends after the electron beam has been off for at least one second.

The operating parameter values and conditions for high intensity target systems and methods (e.g., high temperature, high strain, easy target replacement, etc.) can be different than conventional systems. The operating parameter values and conditions for high intensity target systems and methods (e.g., high temperature, high strain, easy target replacement, etc.) can provide high dose rates, unlike traditional systems in which the operating parameters and conditions (e.g., low temperature, low strain, very difficult target removal, etc.) as a practical matter typically prevent higher dose rates (e.g., greater than 1 Gy/s, etc.). In one embodiment, a high intensity target system and method is configured to be operable with a high energy input electron beam (e.g., greater than 1 MeV, 25 MeV, etc.) and high dose rates. In one exemplary implementation, the higher power operation associated with a high intensity target can enable delivery of average dose rates greater than 1.0 gray per second (Gy/s) and peak dose rates greater than 0.002 Grays per pulse (Gy/pulse). In one embodiment, the Bremsstrahlung radiation corresponds to average dose rates greater than or equal to 1.5 greys per second (Gy/s) at isocenter.

In one embodiment, if the high intensity target is adjusted/moved at a speed of 3-5 m/s then different/sequential pulses hit a different beam impact location that has no/negligible temperature increase due to dissipated heat associated with another pulse. In one exemplary implementation, there is room for a temperature increase by a factor of 2.

In one embodiment, when generating radiation (e.g., x-rays, etc.) from electron beams via Bremsstrahlung mechanisms, most of the electron beam energy delivered to the high intensity target is converted to heat. The conversion to heat can result in high intensity target temperature changes. In one exemplary implementation, a thermal cycle corresponds to rises and falls in temperature as power/energy delivery to a high intensity target is turned on and off in electron beam pulses and cycles. The changes in temperature can lead to detrimental impacts and potentially result in damage to a target. The characteristics of the temperature rise and fall (e.g., how much, how fast, how often, etc.) can determine the amount and type of damage. In one embodiment, efficiently and effectively dealing with potential damage to a target includes addressing failure limitations. The failure limitations can be associated with a point at which a loss of reliable radiation delivery occurs. In one embodiment, a failure includes a permanent change to a target that renders it unable to create/deliver radiation with clinically required properties. In one exemplary implementation, a target fails when it is unable to deliver the radiation properties appropriate for a treatment plan. Failure limitations can be associated with different failure mechanisms.

As indicated above, there are several characteristics of temperature changes (e.g., how much the temperature value changes/rises, how many times/cycles the temperature changes, the rate at which the temperature changes, etc.) due to particle beam impacts that can result in problems/failures in a target. Higher electron beam energy levels can produce higher temperature rises. High temperature rises/values that reach melting point levels can cause a high intensity target to melt. The number of thermal cycles or rises and falls in temperature causes stresses/strains that can result in target failure. A large number of cycles with low temperature changes can cause failure. Also, a small number of cycles with high temperature changes can cause failure. In addition to potential problems associated with the value a temperature rise reaches (e.g., such as melting, etc.), how fast the rise occurs can potentially have other detrimental impacts. Higher electron beam energy levels applied over a short period of time can produce higher temperature rises in a short period of time. A significant amount of temperature change at a rapid rate can cause transient mechanical loads (e.g., stresses, strains, etc.) that result in target failure (e.g., can exceed the ultimate tensile strength of the target, etc.). The different failure mechanisms and limitations can involve exposing a high intensity target to a relatively few cycles (e.g., over a short duration, etc.) versus exposing a traditional target to relatively many cycles (e.g., over a long duration, etc.). Again, it is appreciated that different failure mechanisms and failure limitations can be associated with different characteristics of a temperature rise and fall.

A failure mechanism that involves a rapid and significant change in high intensity target temperature can be referred to as a catastrophic failure mechanism. In one exemplary implementation, a catastrophic failure occurs within one/few thermal cycles (e.g., associated with a few electron beam impact energy cycles, etc.). In one exemplary implementation, a catastrophic failure mechanism can be based upon different factors (e.g., ultimate tensile strength, fracture strain, melting point, etc.). A failure mechanism that involves many thermal cycles and corresponding numerous stress cycles that eventually result in failure/detrimental damage can be referred to as a protracted failure mechanism. A primary factor in a protracted failure mechanism is typically more a focus on a large number of cyclical rises and falls in temperature rather than the rate of temperature change (e.g., per electron beam pulse, etc.) or the amount of temperature change. In one embodiment, catastrophic failure mechanisms cause a failure in 1,000 thermal cycles or less and protracted failure mechanisms cause a failure in more than 1,000 thermal cycles. In one embodiment, a single or few thermal cycles with relatively low temperature changes are not typically problematic. It is appreciated that as a general proposition, the different failure mechanisms can involve different durations/times between the initial introduction of an underlying/root cause of a failure (e.g., electron beam pulse, thermal cycle, stress/strain, etc.) and the point at which a high intensity target fails. In one embodiment, catastrophic failure mechanisms are associated with what is considered substantially instantaneous failure under static load and prolonged failure mechanisms are associated with what is considered prolonged incremental deteriorating cyclical loads that eventually lead to failure.

While catastrophic failure mechanisms and prolonged failure mechanisms can be considered different, it is appreciated that catastrophic failure mechanisms and prolonged failure mechanisms are not necessarily mutually exclusive in every possible failure of a target. It is also appreciated that sometimes in general vernacular catastrophic failure means sudden and debilitating, and that in prolonged failure mechanisms involving fatigue the actual failure (e.g., breaking apart, etc.) may appear to happen suddenly (e.g., within a few cycles, within a short duration, within the 5 cycles between cycle 1,750,000 and cycle 1,750,005, etc.) with debilitating impacts. However, the application of the underlying/root cause (e.g., electron beam pulses, thermal cycles, etc.) in the prolonged failure mechanism can occur over a relatively long duration/many cycles (e.g., from 0 to 1,750,005 cycles, etc.).

In addition, to the extent conventional approaches may coincidentally avoid catastrophic failure mechanism problems (e.g., melting, etc.), traditionally catastrophic failure mechanisms were not the controlling/primary focus in traditional systems, rather traditional approaches mainly focused on prolonged failure mechanisms involving fatigue. Traditional target operation parameter and condition limitations controlled by or based on prolonged failure mechanisms and high lifetime cycles may operate under particular conditions (e.g., low temperature, low percent strain, very infrequent target removal, etc.) that may coincidentally avoid catastrophic failure. However, importantly the traditional target approaches (e.g., operation limits primarily based on/controlled by considerations such as prolonged fatigue failure mechanisms, low currents, low temperatures, etc.) cannot typically generate dose rates greater than 1 Gy/s.

In one embodiment, even though protracted fatigue failure mechanisms do not control/dictate limits on operating parameters and conditions for a high intensity target, having catastrophic failure mechanisms control/dictate limits on operating parameters and conditions can also avoid protracted fatigue failure mechanisms problems. In one exemplary implementation, a high intensity target is replaced before protracted fatigue failure mechanisms cause problems or issues. In one exemplary implementation, replacement based on or controlled by limits associated with catastrophic failure mechanism, a target may suffer catastrophic failure if used for more than 1000 cycles and thus a replacement schedule limitation may indicate to replace the target at or before 1000 cycles (the replacement is based upon and controlled by the catastrophic failure limits). The target may also have failure limitations associated with protracted fatigue failure mechanisms. For example, the target may suffer protracted fatigue failures after 1,000,000 cycles. In one embodiment, catastrophic failure mechanisms cause a failure in 1,000 thermal cycles or less and protracted fatigue failure mechanisms cause a failure in more than 1,000 cycles. There can be different sets of conditions, and a target may suffer catastrophic failure under a first set of conditions (high pulse rate, high current, high temperature, etc.) and protracted fatigue failure under a second set of conditions (low pulse rate, low current, low temperature etc.). The fact that replacing the target after 1,000 cycles may also coincidentally avoid limits associated with fatigue failures (e.g., after 1,000,000 cycles) does not mean a replacement is based upon fatigue failure mechanisms, rather the controlling factor in scheduled replacement is based upon catastrophic failure mechanisms.

Figure 3B:
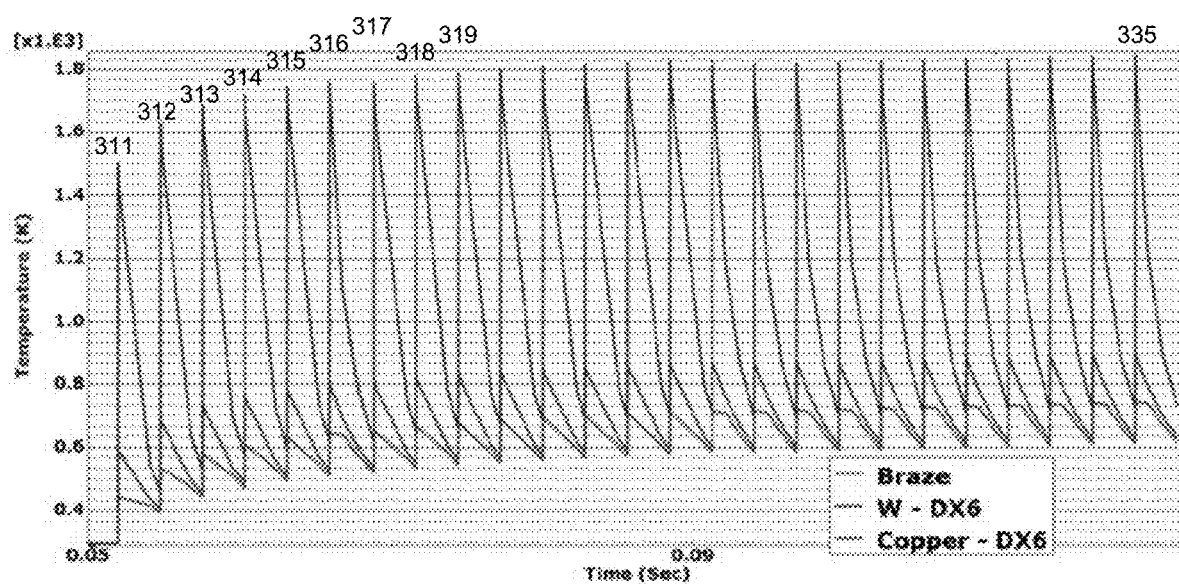
FIG. 3B is an exemplary graph indicating temperature of a high intensity target over time when being impacted by particles in accordance with one embodiment.

As indicated above, it is appreciated the electron beam energy can be delivered to a high intensity target in cycles of multiple pulses. It is also appreciated that the thermal cycle temperature rise and fall can correspond to the energy pulse and cycle delivery. In one embodiment, a power cycle corresponds to a thermal cycle (e.g., applying and removing thermal energy, etc.). A thermal cycle can occur when temperature rises and falls as power is turned on and off. FIG. 3B is an exemplary graph indicating temperature of a high intensity target over time when being impacted by particles in accordance with one embodiment. FIG. 3B illustrates maximum temperature cycles (e.g., 311-319, 335, etc.) in Tungsten, Braze, and Copper for a 6 MeV beam in accordance with one embodiment. In one embodiment, the maximum current of an electron beam impacting a target is 150 (mA) at a pulse repetition rate of 360 (Hz) and an electron beam spot size is 2 (mm). In 2.8 (ms) the max temperature in the tungsten button drops by 780 (C). In one embodiment, nearly the entire energy of the beam pulse is converted into temperature rise of the impacted high intensity target material and absorbed by that particle beam impact location. The temperature jump $\Delta T$ is therefore mainly a function of the impact spot thermal capacity (C) and the energy delivered per pulse (E). In one embodiment, the change/delta in temperature is approximately equal to the energy delivered per pulse divided by impact spot thermal capacity (e.g., $\Delta T \cong E/C$). There is no or negligible heat transfer (e.g., dissipation, conduction to portions of a high intensity target outside the beam impact location, etc.) during a pulse (heat transfer outside the beam impact location requires significantly more time than pulse duration). In one exemplary implementation, the graph shows how the temperature characteristics on three key locations of the target evolve with time over the first few particle beam pulses. As indicated above, the changes in temperature can cause impacts associated with failure mechanisms and in order to reliably provide radiation treatment attention should be given to failure limitations.

Figure 3C:
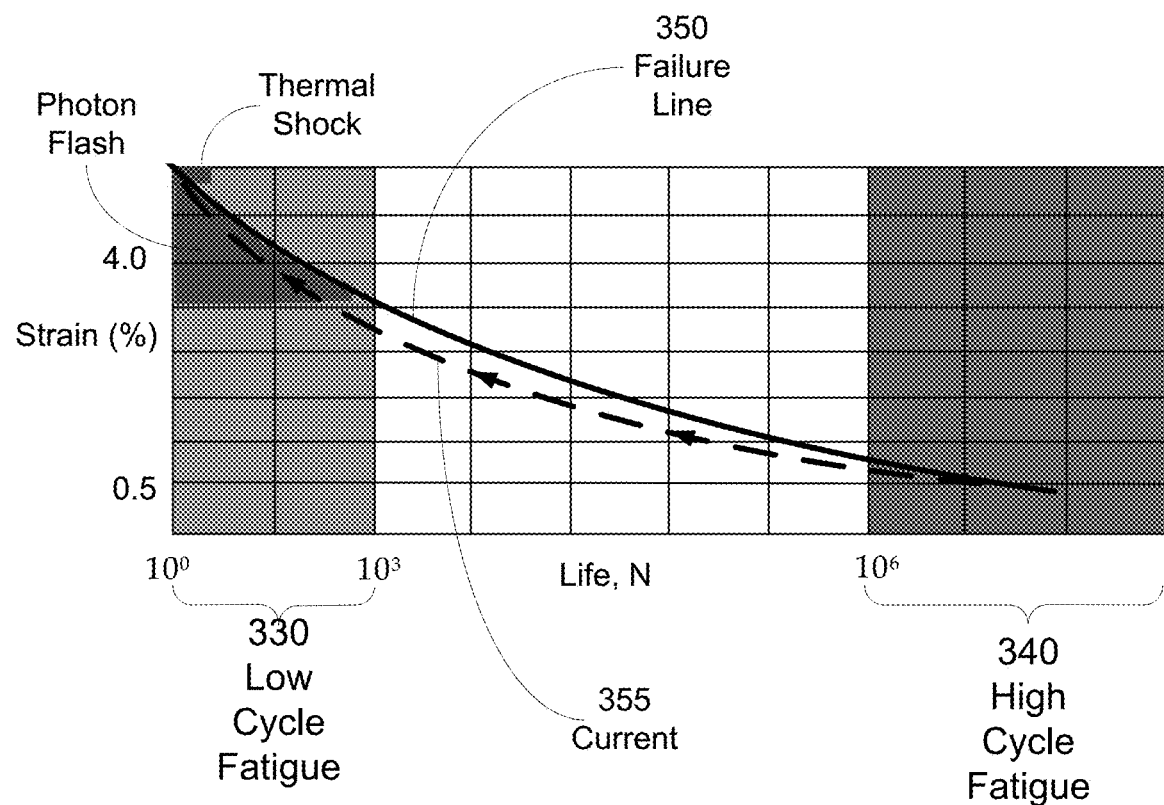
FIG. 3C is a graphical representation of an example of a failure limitation curve illustrated in terms of electron beam impacts vs corresponding strains in accordance with one embodiment.

FIG. 3C is a graphical representation of an example of a failure limitation curve illustrated in terms of electron beam impacts vs corresponding strains in accordance with one embodiment. The horizontal X-axis corresponds to the target life in terms of electron beam impact cycles. The vertical Y-axis corresponds to the amount strain (%) associated with the electron beam impact cycles. In one embodiment, a high intensity target can have a catastrophic failure strain percentage in the range of 0.5 to 4.0 percent. The solid black curve line 350 indicates a failure limitation curve, and targets operating at parameters/values above the failure limitation curve line are likely to fail. Since, as a general proposition increases in stress/strain result from increases in temperature changes caused by electron beam energy, in one embodiment the Y-axis can be considered to have a correlation to electron beam energy. The dashed black curve line 355 indicates the general relationship between an electron beam energy curve and the failure limitation curve line 350.

Low cycle fatigue region 330 is shown in light blue shade and high cycle fatigue region 340 is shown in dark blue.

Typically, traditional targets are not able to handle the thermal cycle changes (e.g., similar to those illustrated in FIG. 3B, etc.) and resulting strains (e.g., similar to those illustrated in FIG. 3C, etc.) associated with high electron beam energy impacts. This dictates that operation of traditional targets is typically limited to a High Cycle Fatigue (HCF) regime (e.g., region 340 in FIG. 3C, etc.). As illustrated in FIG. 3C, allowable strains within a traditional target must be several times lower than in a Low Cycle Fatigue (LCF) regime 330 of a high intensity target. In addition, the HCF reliability regime of a traditional target also places other constraints on the maximum allowable electron beam power compared to LCF reliability regimes of a high intensity target, as illustrated in Table 1 below.

TABLE 1

| | Multi-Use Long Lifetime Traditional Target (HCF regime) | Disposable Intensity Target (LCF regime) |
|---|---|---|
| Maximum allowable temperature in tungsten button. | Recrystallization Temperature Approximately 1,350 C. | Melting Point Approximately 3,400 C. |
| Maximum allowable temperature in Braze layer. | Solidus Approximately 1,000 C. | Not Applicable |
| Maximum allowable temperature in substrate. | Material softens almost linearly with temperature. | Melting temperature of the material |

With reference still to FIG. 3C, the HCF region 340 below the failure line 350 corresponds to a high quantity of cycles with low strain. A portion of the LCF region 330 close to the failure line 350 corresponding to a low quantity of cycles with high strain. The high strain tolerance enables the high intensity target to reliably function in a region (shown in green) with high current and electron beam energy characteristics corresponding to high dose rates (e.g., FLASH, etc.). In one embodiment, electron beam energy and current are controlled to prevent a significant rise in temperature value at a fast rate in a very short time (e.g., within one or few pulses or cycles, etc.), otherwise the high intensity target can potentially experience a thermal shock failure (shown in red).

In one embodiment, a high intensity target system and method includes several novel features that enable realization of photon or X-ray based high dose rate therapies (e.g., greater than 1 Gy/s, FLASH, etc.). The high intensity target system and method novel features/configurations can include movable target characteristics, replaceable target characteristics, adjustable SAD, and coordinated utilization of multiple accelerators. Additional explanation of the high intensity target system and method novel features/configurations as described in other portions of the detailed description.

Movable High Intensity Target

In one embodiment, a moveable high intensity target includes novel features and characteristics that overcome many of the traditional issues/problems associated with temperature rises (e.g., similar to those illustrated in FIG. 3B) and failure limitations (e.g., similar to those illustrated in FIG. 3C). With reference back to FIG. 3C, as previously explained during the few microseconds of beam pulse duration no or negligible heat is conducted away from the initial particle beam impact location since thermal conduction typically occurs on a much slower timescale of milliseconds. In one embodiment, a location the particle beam impacts on a high intensity target is changed/moved from a first location to a second location so that a later beam pulse hits the second location. In one embodiment, the change from the first location to the second location occurs at a rate faster than the thermal conduction rate of the high intensity target. Thus, the second location does not have heat build-up and corresponding raised temperature effects associated with heat conduction from the first location the particle beam impacted. Since the second location is not experiencing temperature effects conducted from the first location, in one embodiment initiation of an electron beam pulse impact can be directed at the second location without concerns for heat effects from prior particle beam pulses, unlike traditional targets. In order for conventional stationary targets to operate reliably and avoid various failure limitations it is usually necessary to wait several milliseconds to allow the target temperature to decay before the next beam pulse is delivered. This typically limits acceptable pulse repetition rates in traditional systems to a few hundred pulses per second. Thus, typical traditional pulse and energy constraints prevent realization of photon or X-ray based high dose rate therapies (e.g., FLASH, etc.).

However, rather than waiting for the temperature to sufficiently decay in an electron beam impact location, a high intensity target system can change/move the electron beam impact location. In one embodiment, movement of an electron beam impact location on a high intensity target can vary (e.g., moved in a step function, continuously moved during treatment, etc.). In one embodiment, the number of pluses that hit an impact location before/while a high intensity target is moved can vary (e.g., a single pulse, multiple pulses, a cycle of pulses, etc.). In one embodiment, movement of an electron beam impact location and a high intensity target can vary (e.g., moved in a step function, continuously moved during treatment, etc.). The different location can be a new location that has not been impacted by a previous pulse. The different location can be a location that was hit by a previous pulse but has sufficiently recovered (e.g., enough time has passed for the heat/temperature associated with the previous pulse to have sufficiently been dissipated/reduced, etc.). In one exemplary implementation, the different location has sufficient thermal capacity to handle/absorb the new pulse energy without melting.

It is appreciated that while it may appear there are some similarities between traditional target approaches and new high intensity target systems and methods, in reality there are numerous significant novel and non-obvious differences. In one embodiment, high intensity target systems and methods are configured with failure limitations based primarily on catastrophic failure mechanisms rather than protracted fatigue failure mechanisms, unlike traditional approaches. Additional discussion on different aspects of high intensity target systems and methods are presented in other portions of this detail description section.

FIG. 4 is a block diagram of particle beam impact locations on a high intensity target 3500 surface in accordance with one embodiment. The impact locations can have various configurations. The impact locations 3521 through 3528 are adjacent to one another. The impact locations 3531 through 3538 have spaces between one another. The impact locations 3541 through 3548 overlap one another. The footprint or outline of the particle beam impact locations can have different shapes (e.g., square, circle, rectangle, etc.). In one embodiment, regardless of the impact location configuration, movement of the location of charged particle impact is based on thermal diffusion and is moved at a rate greater than diffusion of detrimental heat impacts on the replaceable high intensity target. In one exemplary implementation, the speed or rate of target movement is not less than the speed at which the thermal power in the target travels by diffusion. As explained above, this can avoid run-away stack up of temperature jumps.

In one embodiment, an electron beam impact overlap occurs when a portion of a previous electron beam pulse impact and a subsequent electron beam pulse impact hit the same surface area of a target while heat effects associated with the previous electron beam pulse is still present in the location. In one exemplary implementation, an energy per pulse value for the electron beam is picked to account for an overlap in impact locations. In one embodiment, the energy per pulse value for the electron beam is selected so that the high intensity target does not suffer a failure and is unable to provide reliable radiation generation.

Figure 5:
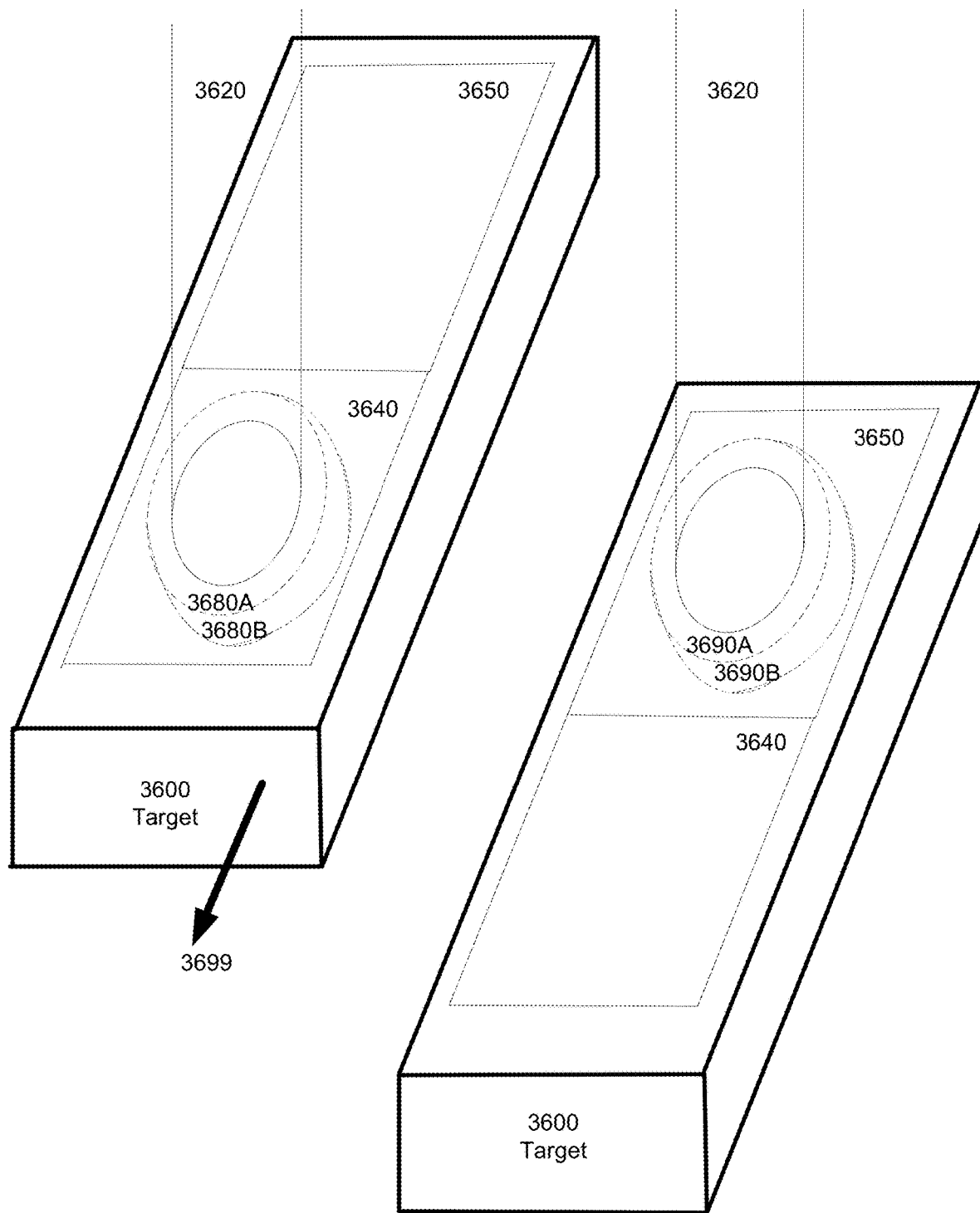
FIG. 5 is a block diagram of an exemplary adjustment of a particle impact location on a high intensity target in accordance with one embodiment.

FIG. 5 is a block diagram of an exemplary adjustment of a particle impact location on a high intensity target 3600 in accordance with one embodiment. High intensity target 3600 includes particle impact locations 3640 and 3650. Particle impact locations 3640 and 3650 are shown as adjacent locations similar to impact locations 3521 through 3528 in FIG. 4. It is appreciated that the movement of impact locations can also apply to impact locations that have spaces between one another (e.g., similar to 3531 through 3538 in FIG. 4, etc.), impact locations that overlap one another (e.g., similar to 3541 through 3548 in FIG. 4, etc.) and so on. The particles from particle beam 3620 collide with molecules in high intensity target 3600 resulting in the release of energy as radiation and heat. During a first time period particle beam 3620 impacts replaceable high intensity target 3600 in particle impact location 3640. The particle beam 3620 penetrates into the high intensity target material and then diffuses radially outwards. The resulting heat is dispersed in region 3680 with the heat spread from a surface perspective shown as 3680A and the heat spread into high intensity target 3600 shown as 3680B.

During a second time period (e.g., before detrimental heat spread can reach the boundaries of particle impact location 3650) the impact of particle beam 3620 is adjusted or moved to particle impact location 3650. In one embodiment, the particle impact location is adjusted by moving the high intensity target 3600 in the direction 3699 until the particle beam 3620 is in particle impact location 3650. The resulting heat is dispersed in region 3690 with the heat spread from a surface perspective shown as 3690A and the heat spread into high intensity target 3600 shown as 3690B. In one exemplary implementation, the heat impact 3680 significantly dissipates and is substantially gone from particle impact location 3640 during the second or future time period.

In one embodiment, the number of pluses that hit an impact location before/while a high intensity target is moved can vary (e.g., a single pulse, multiple pulses, a cycle of pulses, etc.). In one exemplary implementation, a single pulse 311 hits particle impact location 3640 and the target is moved so that the next pulse 312 hits particle impact location 3650. In one exemplary implementation, a first plurality of pulses (e.g., 311, 312, 313, 314, etc.) hit particle impact location 3640 and the target is moved so that the next plurality of pulses (e.g., 315, 316, 317, 318, etc.) hit particle impact location 3650. It is appreciated that the number of cycles/pulses that can impact a high intensity target before reaching failure limits (e.g., less than pulse 335, more than pulse 335, etc.) can change based upon various things (e.g., type of high intensity target material, configuration of the high intensity target, energy level of electron beam impacting the high intensity target, etc.).

It is appreciated a high intensity target can have a variety of configurations. The configurations can provide additional assistance/aid to various radiation system operations (e.g., achieving radiation generation characteristics, dose rates, target insertion ejection, target movement, etc.,) beyond simple generation of Bremsstrahlung radiation. The changes can lead to a difference in the actual configuration (material, shape, size, etc.) of the target relative to traditional approaches. For example, a high intensity target can be structurally different (e.g., different material, etc.) than a traditional target.

It is appreciated a high intensity target can include various materials. Different regions or portion of a high intensity target can be made of different composition and have different characteristics in different regions/locations. In some embodiments, the components of a high intensity target can have various characteristics including one or more of the following: a layer of high atomic number material having high density, a layer of low atomic number, and low density material, high heat capacity, high thermal conductivity, high melting point, high boiling point, high electrical conductivity, high yield strength, physical properties relatively unaffected by radiation (radiation hard or Rad-hard), noncorrosive, and so on. The high intensity target can be configured with various materials (e.g., beryllium, titanium, carbon, copper, tungsten, braze, etc.). Coordinated configuration of a high intensity target can facilitate enhanced performance In one embodiment, a high intensity target includes various materials (e.g., copper, steel, tungsten, etc.). In one exemplary implementation, a high intensity target includes at least 80 percent of one material by atomic weight. The high intensity target can be a monolithic structure and remaining portions can be impurities by atomic weight. A high intensity target can include 95 to 99.7 percent copper by atomic weight; and 0.3 to 5 percent impurities by atomic weight. A high intensity target can be steel based and include 95 to 99.7 percent iron by atomic weight; and 0.3 to 5 percent impurities by atomic weight. A high intensity target can include 95 to 99.9 percent Tungsten by atomic weight; and 0.1 to 5 percent impurities by atomic weight. It is appreciated a replaceable high intensity target can include various combinations of material (e.g., Tungsten and Steel, Cooper and Steel, Tungsten and Copper, etc.). The combinations can be made with various joining techniques (e.g., brazing, welding, back casting, etc.). A high intensity target can include alloys. In one exemplary implementation, a high intensity target includes at least 80 percent of an alloy by weight.

A high intensity target can have different configurations including varying contours (e.g., bumps, ridges, etc.), shapes, and thicknesses based upon heating characteristics of the replaceable high intensity target. In one embodiment, a high intensity target is thick enough to stop a high energy electron beam while thin enough to avoid self-attenuation. The contours, shape, and thicknesses can be configured to mitigate detrimental heating characteristics and disbursement issues. The contours, shapes, and thicknesses can be configured for radioactive emission characteristics. In some embodiments, the contours, shapes, and thicknesses can be configured for radiation resistance or blocking ability. In some embodiments, a high intensity target enables increased controllability and performance over conventional Xray target applications.

In addition, the target does not have to include a tungsten layer or copper substrate. Reduced cost of the high intensity target can be achieved by using all copper targets, such as used for the 8× and 10× modes on a Varian TrueBeam for example, or by replacing the copper substrate with less expensive materials, such as steel for example. The high intensity target can be configured to collaboratively contribute to radiation emission, energy absorption, heat dissipation, and so on. In one embodiment, a high intensity target can be configured to handle 200 pulses in 2 mm particle impact locations and have a total length of approximately 0.04 m long.

In one embodiment, a high intensity target is configured in layers. The layers can have different characteristics (e.g., radiation generation capability, z value, heat dissipation, heat transfer, melting points, thermal strain characteristics, etc.). FIG. 6 is a block diagram of exemplary configurations of high intensity targets in accordance with one embodiment. High intensity target 3751 is a single layer 3752 comprising a single layer configuration of the same substance (e.g., metal, compound, alloy, etc.). High intensity target 3871 is a multiple layer configuration. High intensity target 3871 includes layer 3872 and layer 3873. In one embodiment, layer 3872 and layer 3873 include different substances. In one embodiment, layer 3872 and layer 3873 include the same substances.

Figure 7:
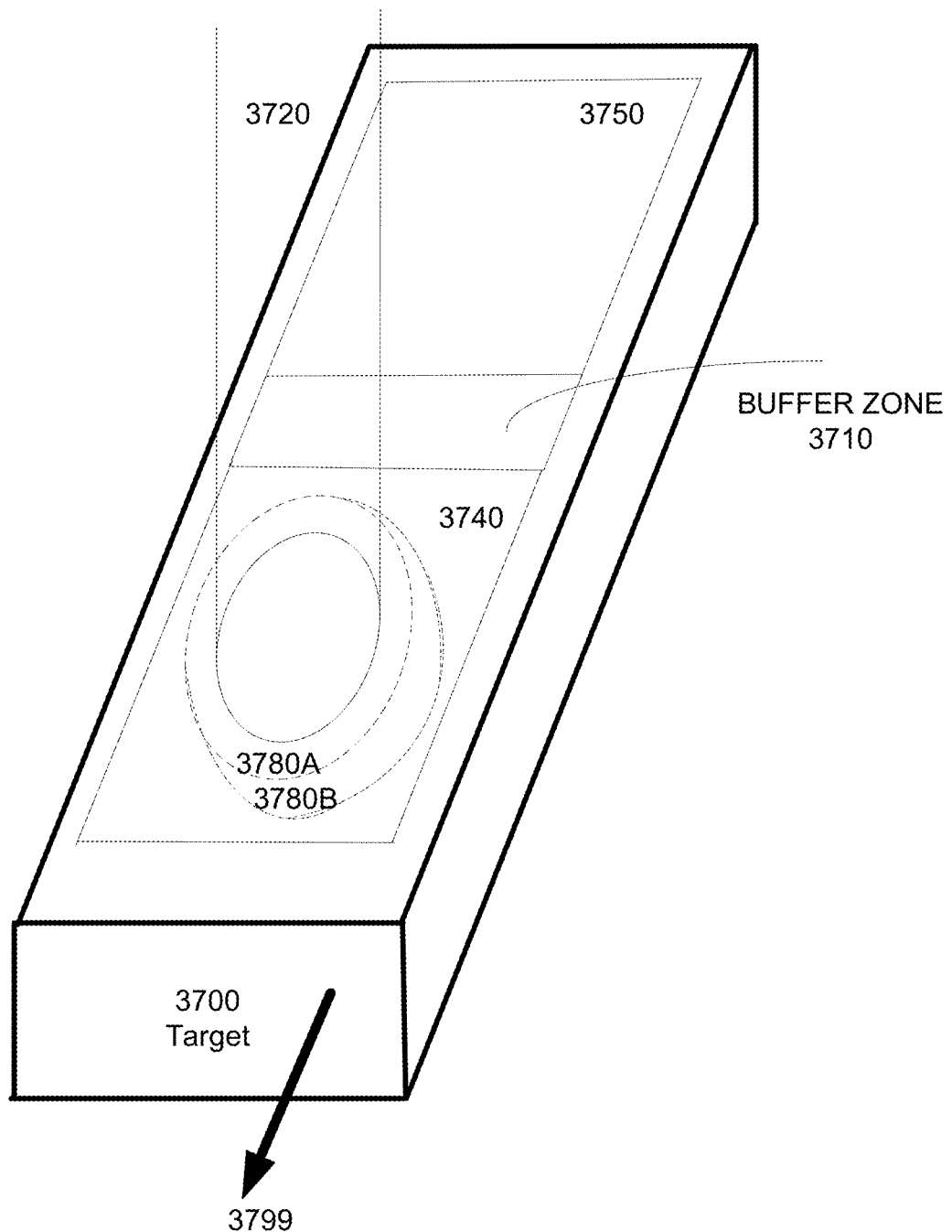
FIG. 7 is a block diagram of a high intensity target in accordance with one embodiment.

FIG. 7 is a block diagram of a high intensity target 3700 in accordance with one embodiment. In one embodiment, high intensity target 3700 is similar to high intensity target 3600. High intensity target 3700 includes particle impact locations 3740 and 3750. The particle beam 3720 penetrates into the high intensity target material and then diffuses radially outwards. The resulting heat is dispersed in region 3780 with the heat spread from a surface perspective shown as 3780A and the heat spread into high intensity target 3710 shown as 3780B. Buffer zone 3710 can help prevent/deter the diffusion/spread of heat into that area of particle impact location 3750, and vice versa. In one embodiment, high intensity target features and characteristics (e.g., configuration, substance, shape, contour, material, etc.) enables buffer zone 3710 to help prevent/deter heat diffusion/spread.

Figure 8:
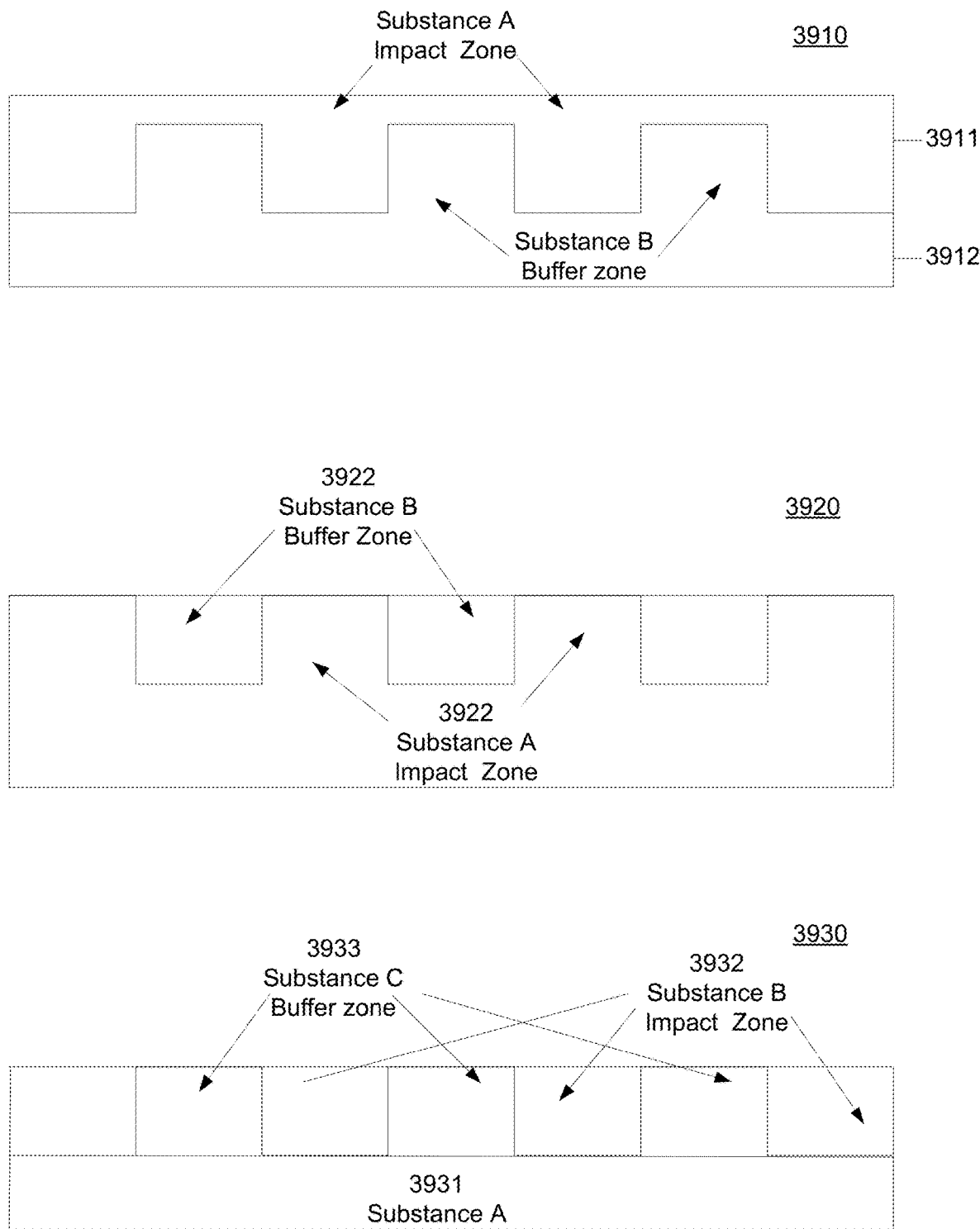
FIG. 8 is block diagram of high intensity target configurations in accordance with one embodiment.

FIG. 8 is block diagram of high intensity target configurations in accordance with one embodiment. High intensity target 3910 includes layers 3911 and 3912. In one embodiment, layer 3911 includes substance A and layer 3912 includes substance B. In one embodiment, high intensity target 3910 includes higher concentrations of substance A in an impact zone and higher concentrations of substance B in a buffer zone. In one embodiment, substance A is a high radiation generation substance and substance B is resistant to heat dissipation. High intensity target 3920 includes portions or zones comprising substance A (e.g., 3921, etc.) and portions or zones comprising substance B (e.g., 3922, etc.). The contour of the substances can be configured to align with particle impact locations/zones and buffer areas. In one embodiment, high intensity target 3930 includes portions or zones comprising substance A (e.g., 39931, etc.), portions or zones comprising substance B (e.g., 3932, etc.), and portions or zones comprising substance C (e.g., 3939, etc.). In one exemplary implementation, substance A can act as a substrate, substance B can act as particle beam impact location, and substance C areas can act as a heat transfer buffer.

Figure 9:
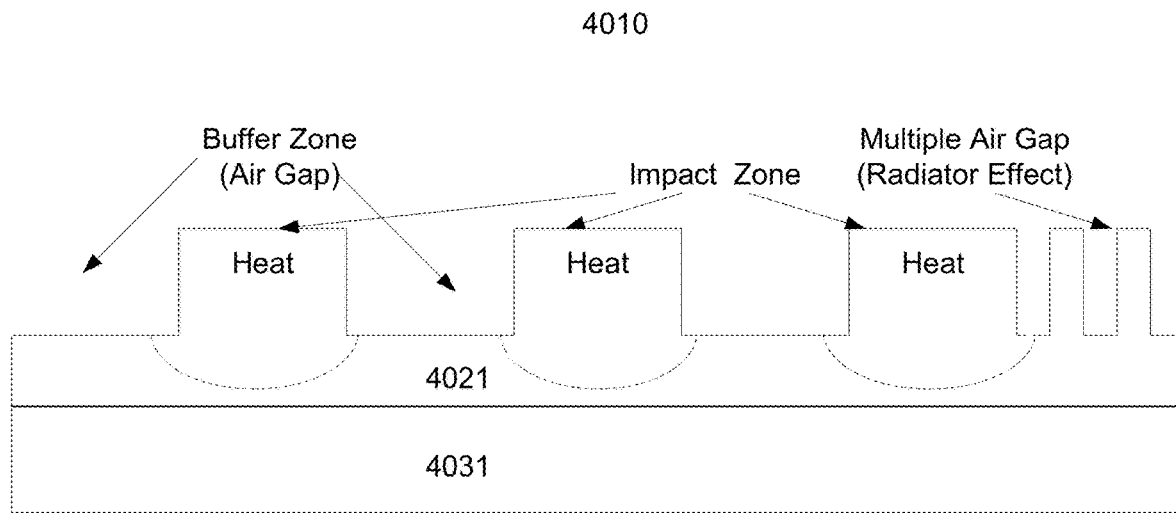
FIG. 9 is a block diagram of exemplary high intensity target in accordance with one embodiment.

FIG. 9 is a block diagram of exemplary high intensity target 4010 in accordance with one embodiment. Replaceable high intensity target 4010 includes layers 4021 and 4031. In one embodiment, the surface contours of high intensity target 4010 can help prevent/deter the diffusion/spread of heat within the replaceable high intensity target 4010. In one exemplary implementation, the contours create air gaps between particle impact locations/zones. In one embodiment, the surface contours of replaceable high intensity target 4010 can also help promote or aid the release/emission of heat from the replaceable high intensity target 4010. In one exemplary implementation, the contours create a radiation effect that helps release heat from the replaceable high intensity target 4010.

Figure 10:
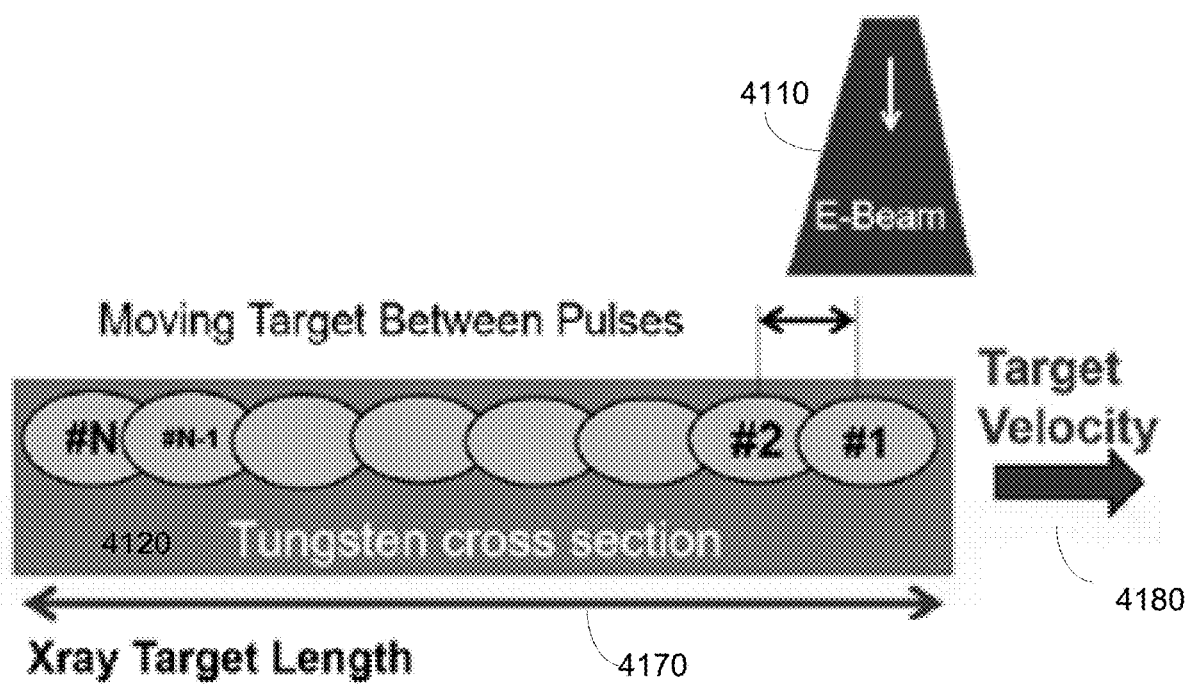
FIG. 10 is a block diagram illustrating the movement of a replaceable high intensity target in accordance with one embodiment.

FIG. 10 is a block diagram illustrating the movement of a replaceable high intensity target in accordance with one embodiment. A particle beam 4110 impacts high intensity target 4120. Replaceable high intensity target 4120 is moved at a target velocity of 4180 so that particle impact from particle beam 4110 traverses from particle impact location #1 to particle impact location #2. The movement traverses the particle impact locations up to and including particle impact locations #N−1 and #N along a length 4170 of the high intensity target. In one exemplary implementation, the length 4170 the particle beam 4110 traverses is equal to the velocity times a treatment duration. In one exemplary implementation, the length the particle beam 4110 traverses before changing direction is a portion/fraction of overall length 4170. In one embodiment, location of charged particle impacts on the replaceable high intensity target is changed at a speed of greater than or equal to 0.3 meters per second.

It is appreciated that particle impact adjustment motions or patterns on a high intensity target can vary. FIG. 11 is a block diagram of exemplary particle impact adjustment motions or patterns in accordance with one embodiment. A replaceable high intensity target 4210 is adjusted so that particle beam 4280 traverses the particle impact location 4220, 4230, 4240, and 4250. Particle beam 4280 can move in a uniaxial linear motion 4271 (e.g., from particle location 4220 to 4230 and 4230 to 4220, or alternatively from particle location 4220 to 4240 and 4240 to 4220, etc.). Particle beam 4280 can move in a multi stage motion 4272 (e.g., from particle location 4220 to 4230, 4230 to 4220, 4220 to 4240, 4250 to 4230, 4250 to 4240, etc.). Particle beam 4280 can move in a circular motion 4273 (e.g., from particle location 4220 to 4230 to 4250 to 4240 to 4220, or from particle location 4220 to 4240 to 4250 to 4230 to 4220, etc.). The movement of a location charged particle impact on a high intensity target can be based upon various factors (e.g., melting temperature, power limits, etc.).

In one embodiment, a replaceable high intensity target travels between pulses so that each electron beam pulse hits a new, previously non-impacted spot (see FIG. 4, 5, etc.). In one exemplary implementation, a pulse repetition rate can be 500 pulses per second (pps). In one exemplary implementation, for a pulse repetition rate of 1,800 pps, the target can move at a linear speed of approximately 5 m/s. In one exemplary implementation, for a pulse repetition rate of less than 1,000 pps the translation speed would be approximately 3 m/s. This is well in the range of high speed linear actuators and on the low end of what can be achieved with conventional rotating mechanisms. In one exemplary implementation, for a 10 cm diameter track, a rotational speed of only 20 Hz or 1,200 rpm is utilized. It would then take 50 ms before a previously exposed spot would be hit again. This can be sufficient time for the deposited energy from the previous pulse to dissipate through the material. In one embodiment, a 20 Gy treatment utilizes 6 revolutions per target, placing it well into the Low Cycle Fatigue (LCF) regime.

Figure 12:
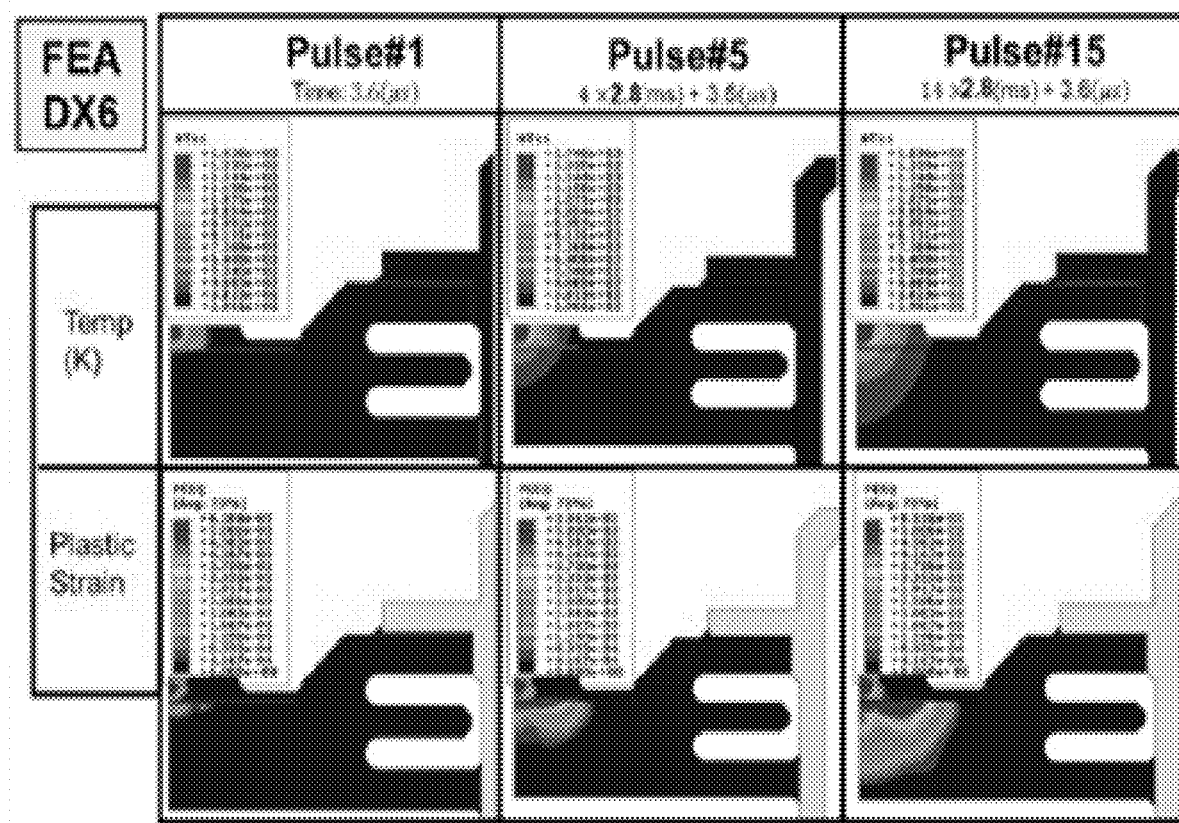
FIG. 12 is a graphical representation example for a thermal profile of a non-moving conventional Xray target.

FIG. 12 is a graphical representation example for a thermal profile of a non-moving conventional Xray target. The graphical representation illustrates how the thermal profile within the target evolves with each additional pulse. In one embodiment, the temperature and plastic strain maps correspond to utilization of a fixed 6 MeV target. In one exemplary implementation, the max target current is 150 mA, the repetition rate is 360 Hz, and the beam spot size is 2 mm.

Figure 13:
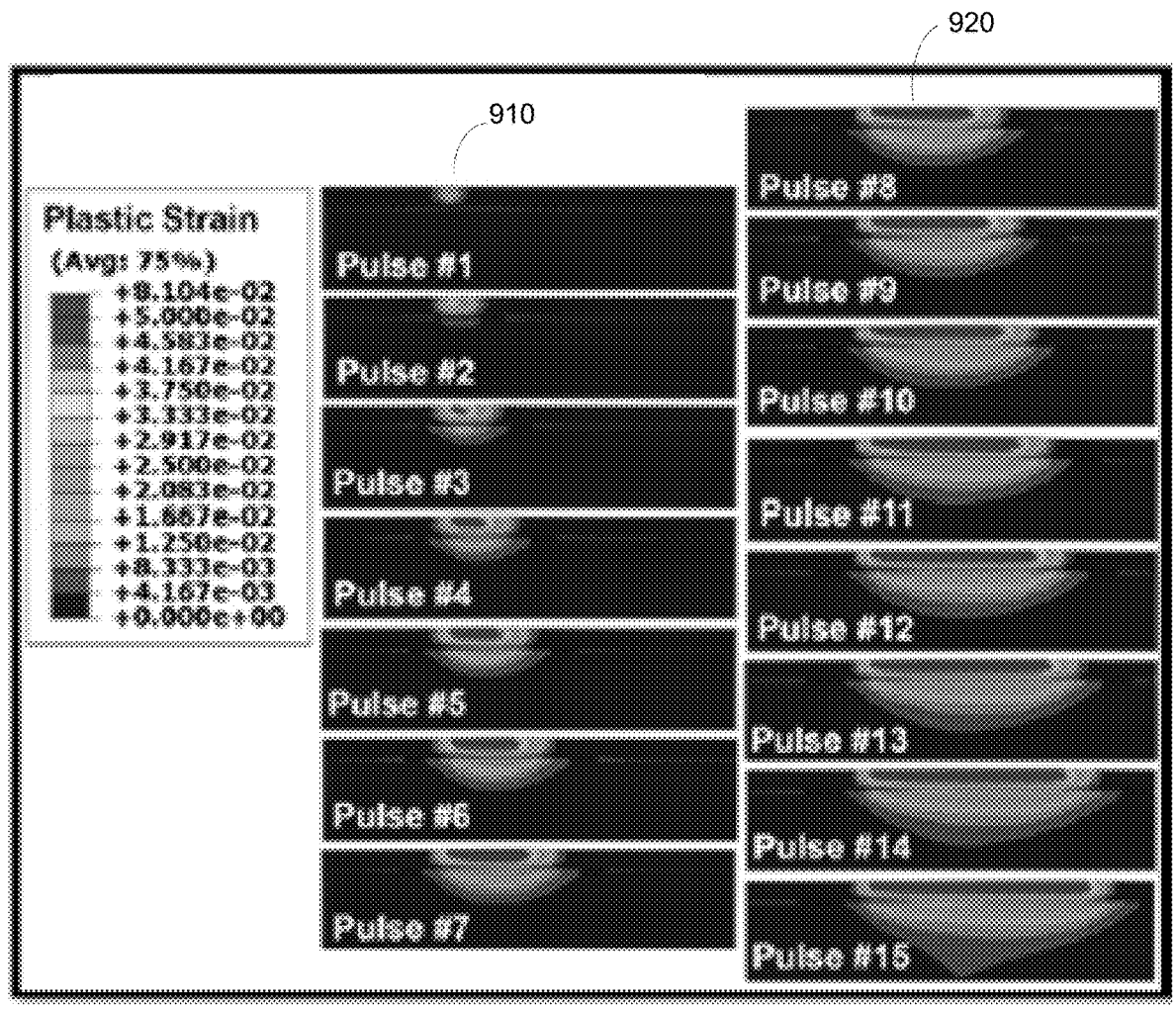
FIG. 13 is a graphical representation of an example maximum plastic strain map for a moving target in accordance with one embodiment.

FIG. 13 is a graphical representation of an example maximum plastic strain map for a moving target in accordance with one embodiment. The center of the impact regions (e.g., 910, 920, etc.) show the relative increase to greater than 5% equivalent plastic strain. In one embodiment, the max target current is 275 mA, the repetition rate is 650 Hz, and the beam spot size is 2 mm.

Figure 14:
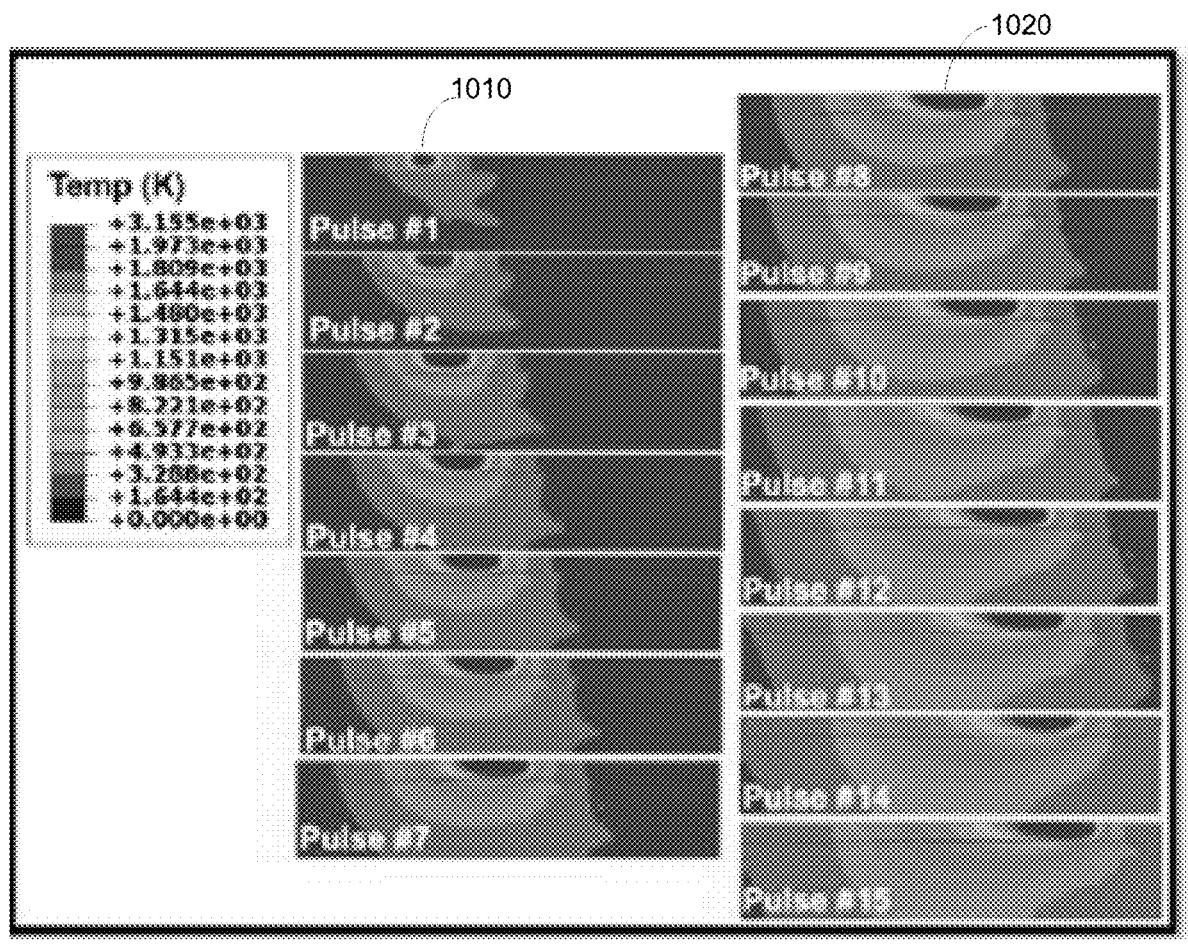
FIG. 14 is a graphical representation of an example maximum temperature for a moving target in accordance with one embodiment.

FIG. 14 is a graphical representation of an example maximum temperature for a moving target in accordance with one embodiment. The center of the impact regions (e.g., 1010, 1020, etc.) show the relative increase to regions with greater than 1973K (1700 C.) temperature.

FIGS. 13 and 14 illustrate that in one embodiment an adjustment in the particle beam impact location on a high intensity target of 2-3 mm in-between pulses is enough to avoid melting of target material.

Figure 15:
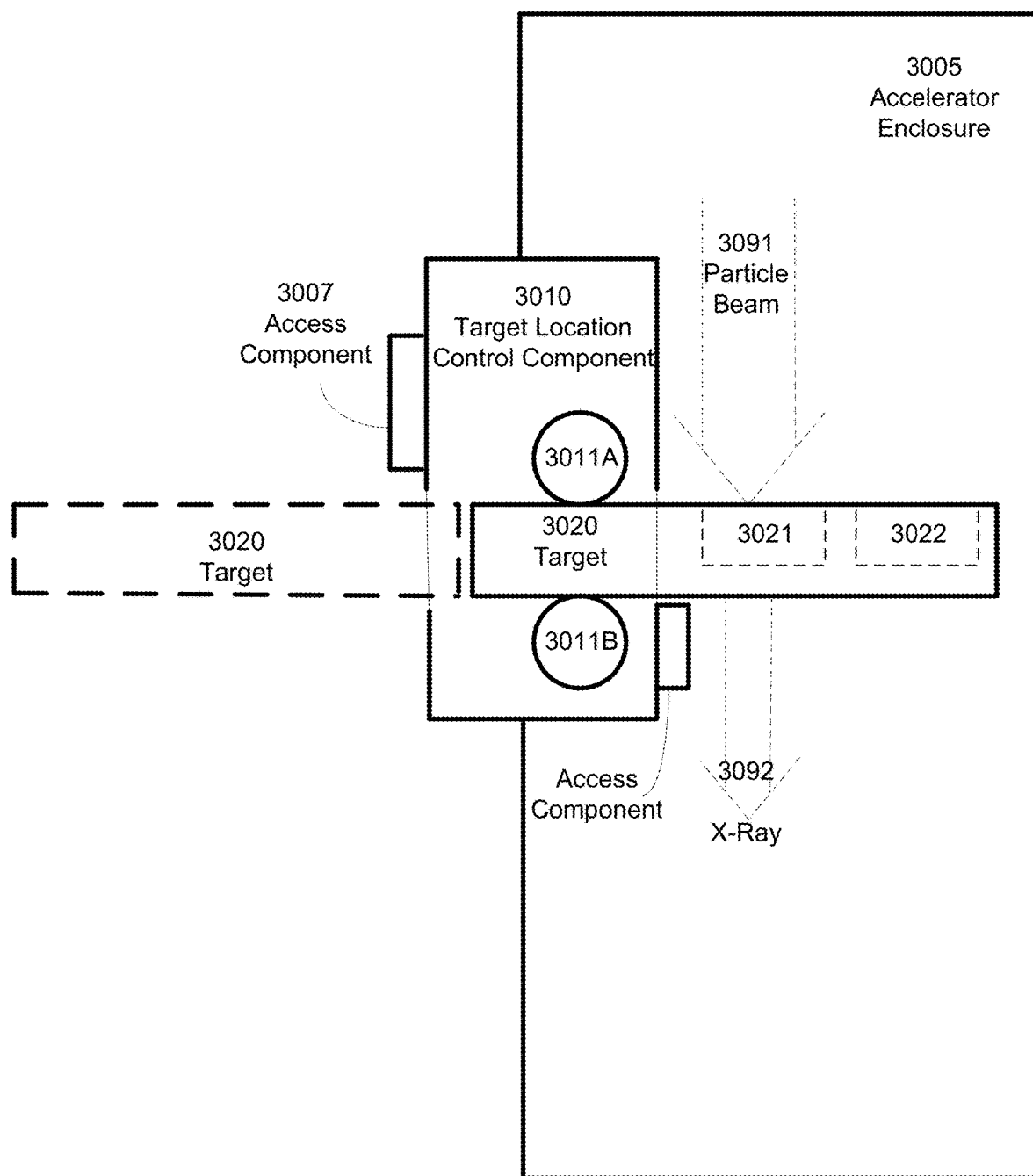
FIG. 15 is block diagram of a high intensity target system in accordance with one embodiment.

FIG. 15 is block diagram of a high intensity target system 3000A in accordance with one embodiment. High intensity target system 3000A includes target location control component 3010. In one embodiment, target location control component 3010 is similar to target location control component 119 in FIG. 1. Target location control component 3010 includes a mechanism for controlling the movement of the high intensity targets. It is appreciated that target location control component 3010 can include various types of mechanisms for controlling the movement of the high intensity targets (e.g., roller, ball, belt, rack and pinion, spring, pneumatic, electronic actuator, etc.). In one embodiment, target location control component 3010 includes mechanism 3011A and 3011B for controlling adjustments or movements of high intensity target 3020. Target location control component 3010 can be used to assist loading and unloading of target 3020 (e.g., from a location shown in dashed lines outside accelerator enclosure 3005 to a location within accelerator enclosure 3005, etc.). In one exemplary implementation, access component 3007 can be used to permit/deny access to accelerator enclosure 3005. Target location control component 3010 adjusts high intensity target 3020 into a position to be impacted by particle beam 3091 and generate X-ray beams (e.g., 3092, etc.). During a first time period high intensity target 3020 is adjusted/moved so that particle beam 3091 impacts location 3022 and during a second time period high intensity target 3020 is adjusted/moved so that particle beam 3091 impacts location 3021, or vice versa. High intensity target 3020 can be adjusted/moved so that particle beam 3091 impacts various locations in different configurations (e.g., adjacent, overlapping, separated, similar to FIG. 4, etc.). In one embodiment, a high intensity target is moved to and from a location (e.g., 3022, 3022, etc.) multiple times.

It is appreciated the target can be moved by an automated movement system. FIG. 16 is a block diagram of an exemplary target movement system 3100 in a first configuration 3100A and second configuration 3100B in accordance with one embodiment. The target movement control component 3107 and movement coupling mechanism 3109 can be located in an accelerator enclosure (not shown). The movement coupling mechanism 3109 can be a releasable coupling mechanism (e.g., grabbing, clamping, clasping, etc.) that selectively couples with holding component 3100 (that holds high intensity target 3151) in configuration 3100A and selectively couples with high intensity target 3152 in configuration 3100B. In one embodiment, a holding component and high intensity target can include holding/moving assist features to help the holding component/moving system engage with the holding component and high intensity target. In one exemplary implementation, holding component 3010 and high intensity target 3151 are configured with a coupling aid (e.g., notch, grasping, clamping, etc.) that also acts as a holding/moving assist feature.

Figure 17:
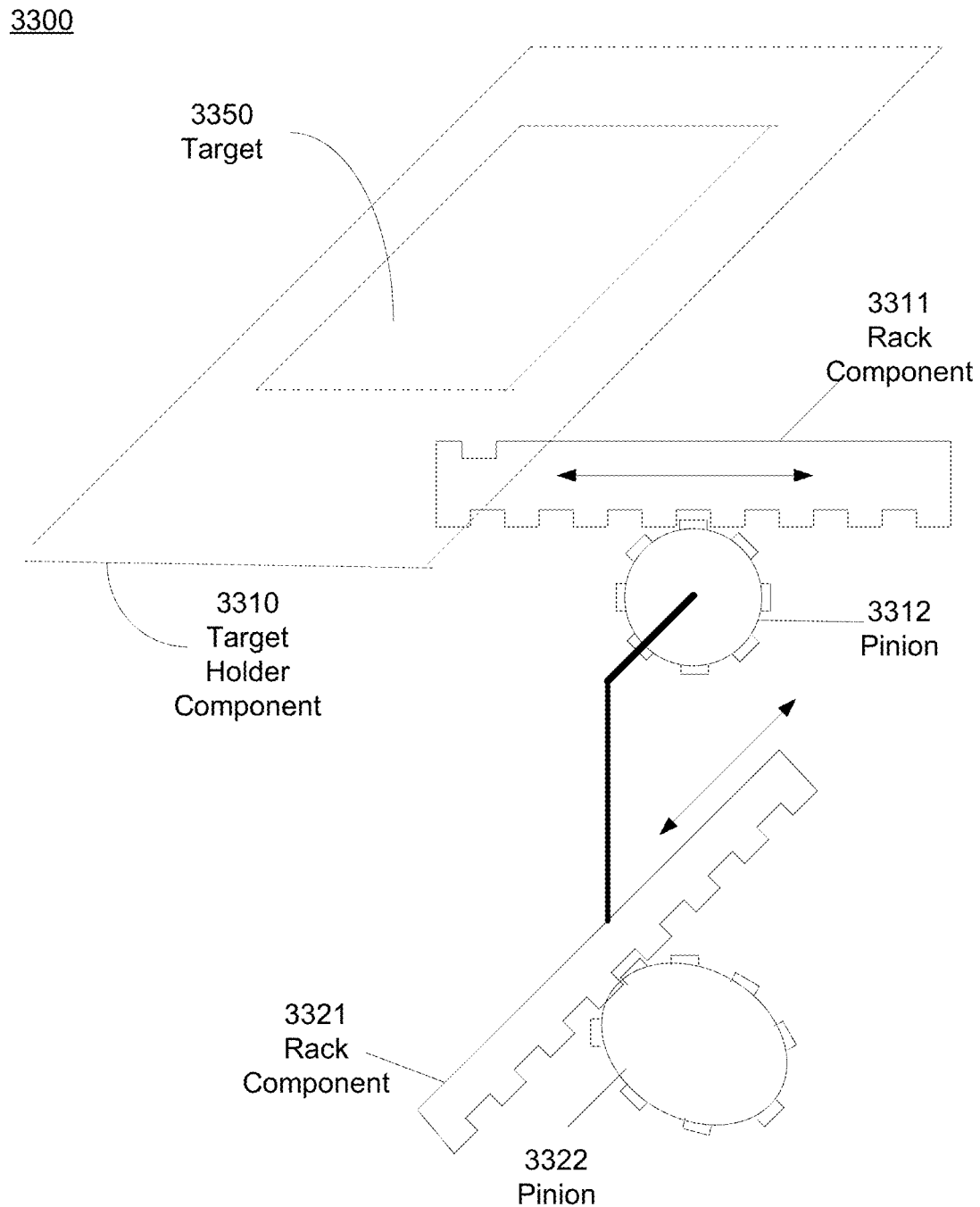
FIG. 17 is a block diagram of an exemplary rack and pion movement system in accordance with one embodiment.

FIG. 17 is a block diagram of an exemplary rack and pion movement system 3300 in accordance with one embodiment. Rack and pion movement system 3300 includes target holding component 3310 that is moved in a plane. Holding component 3310 holds replaceable high intensity target 3350. Rack 3311 moves the holding component 3310 in a first direction in the plane based upon rotation of the pinion 3312 and rack 3321 moves the holding component 3310 in a second direction in the plane based upon rotation of the pinion 3322.

With reference back to FIG. 1, the target location control component 119 is configured to control the impact location of particles on the replaceable high intensity target 117. In one embodiment, the target location control component 119 adjusts/moves the replaceable high intensity target 117 resulting in adjustments to the location of particle impact on the replaceable high intensity target 117. In one embodiment, the target location control component 119 can use other mechanisms (e.g., adjustments to the particle beam, the particle source 111, the acceleration portion 115, etc.) to cause adjustments to the location of particle impact on the high intensity target 117. In one exemplary implementation the particle beam is manipulated (e.g., bent, steered, etc.). In one embodiment, adjustments in the location of particle impact on the replaceable high intensity target 117 are based upon heat generated by the impact and collision with the replaceable high intensity target 114 components. Additional description of adjustments to the location of particle impact on the replaceable high intensity targets is presented in other portions of this specification.

As previously mentioned, charged electron collisions with high intensity targets can result in thermal impacts that can cause localized damage in a high intensity target. In one embodiment, even though electron beam impact locations can be changed/moved to help reduce/mitigate the occurrence and extent of localized damage, when operating at high energy levels some localized damage may occur. The amount of localized damage that occurs with an electron beam pulse can vary (e.g., based upon power level, duration, target material, etc.). In one exemplary implementation, an impact location can take multiple applications of a pulsed high energy electron beam before the localized damage reaches a level of unacceptably interfering with reliable radiation generation and delivery. In one exemplary implementation, an electron beam can return to an impact location multiple times (e.g., up to a number where detrimental impacts begin to reach a level of unacceptably interfering with reliable radiation generation and delivery). It is appreciated, that high intensity target approaches for dealing with potential localized impacts are compatible with various adjustments schemes and regimes.

In one embodiment, efficiently and effectively dealing with localized damage includes addressing failure limitations. The failure limitations can be associated with a point at which a loss of either reliable radiation delivery performance at relatively high dose rates (e.g., greater than 1 Gy/s, etc.) or overall system integrity maintenance occurs. In one embodiment, failure limitations can be associated with different failure mechanisms. With reference back to FIG. 3C, it is appreciated that a high intensity target with movable electron beam impact locations can reliably operate at higher energy levels, the high intensity target can be at risk of failure when operating above the failure curve in the low cycle fatigue region. In one embodiment, a high intensity target is readily replaceable at a "life time" corresponding to a low cycle value (e.g., 1,000 or less electron beam pulse cycles, etc.).

FIG. 18 is a flow chart of an example high intensity target method 4700 in accordance with one embodiment. In one embodiment, high intensity target method 4700 includes processes for efficiently and effectively dealing with localized damage that can be associated with increased dose rates (e.g., greater than 1 Gy/s, etc.) and increased power levels (e.g., greater than 1 Mev, etc.). In one exemplary implementation, high intensity target method 4700 includes changing/moving particle impact locations and replacing high intensity targets.

In block 4710, a charged particle is generated.

In block 4720, the charged particle is accelerated.

In block 4730, radiation is generated in response to impact by the charged particle on a high intensity target.

In block 4740, an impact location of the charged particle on the high intensity target is changed. The change in the impact location is in part based upon heat generation resulting from the impact of the charged particle on the high intensity target and generation of the radiation.

In block 4750, the high intensity target is selectively inserted and removed to and from use. In one embodiment, the high intensity target is removed after 5 treatment uses. In one exemplary implementation, a high intensity target is disposed of after removal. The inserting and removing of the high intensity target can be performed automatically.

High intensity target systems and methods can have various operational aspects (e.g., actions, features, components, scheduling, characteristics, etc.) that are different from traditional systems and methods. Unlike typical conventional Xray targets, a high intensity target can operate under a catastrophic failure mechanism regime and in the LCF region. In one embodiment, a high intensity target with a product life in the LCF regime range can therefore be pushed significantly harder with respect to energy and temperature levels than a traditional target since a high intensity target only has to withstand catastrophic failure mechanism energy and cycle limitations instead of more stringent energy and cycle limitations associated with protracted failure mechanisms and cyclical fatigue. In one exemplary implementation, a high intensity target only needs to last a limited number of thermal cycles before it fails. In one embodiment, a change from a HCF to the LCF regime can allow approximately a doubling of energy deposition per electron beam pulse. In one embodiment, a LCF regime means increasing the allowable dose per pulse. In one exemplary implementation, there is at least a doubling of beam current or pulse width and hence at least doubling of the dose rate. A change from a HCF to the LCF regime can allow a power limit to be set by or based upon melting temperature of a material which constitutes at least a portion of a high intensity target rather than cyclical fatigue/strain limitations. In one embodiment, a switch from a HCF to a LCF regime means a target needs to accommodate different replacement regimes.

High intensity targets can accommodate replacement regimes associated with operations and performance subject to catastrophic failure mechanisms and LCF regimes. In one embodiment, replacement regimes of a high intensity target are different (e.g., easy, fast, convenient, simple, less effort, etc.) compared to traditional approaches. High intensity target system and method replacement regimes can differ in replacement initiation triggers and ease of target loading/unloading. In one embodiment, the occurrence of replacement of the replaceable high intensity target is based upon thermal shock rather than cycle protracted fatigue failure. Additional discussion on different aspects of high intensity target systems and methods are presented in other portions of this detail description section.

Various aspects of high intensity target system and method replacement regimes can be different than conventional approaches. Various target replacement metrics can be used to measure/indicate when initiation of target replacement should commence (e.g., a particular predetermined date/time, before a particular event/activity, before a certain number of radiation pulses, before a certain number of treatments, etc.). There can be shorter durations between scheduled replacements of a high intensity target (e.g., less than or equal to a month, less than or equal to a week, less than or equal to 2 days, etc.), unlike a conventional system or method that waits a significant time (e.g., multiple years, decades, etc.) before a target is removed. There can be less radiation activities (e.g., less than or equal to 10,000 pulses, less than or equal to 1 million pulses, less than or equal to 10,000 Monitor Units (MU), etc.) between replacements of a high intensity target than a typical traditional target approach. There can be less patient treatment activities (e.g., less than 100 treatments, less than 3 treatments, one treatment, etc.) between replacements of a high intensity target than a typical traditional target approach. In one exemplary implementation (e.g., see FIG. 3C, etc.), a high intensity target operating in an LCF regime is scheduled for replacement at the end of the LCF life range (e.g., under 1,000 use cycles, etc.) versus a traditional approach schedule operating in a HCF regime scheduled for replacement at the end of the HCF life range (e.g., above 100,000 use cycles, etc.).

In one embodiment, a high intensity target replacement is very different than conventional assembly/disassembly of the accelerator enclosure and removal/attachment of a target by a user. A high intensity target system and method can involve simple access to the target without involving other radiation components. A prior art target removal/repair typically involves significant assembly/disassembly of an accelerator enclosure that gains general access to multiple components and can require removal of other components (e.g., radiation shielding, drive mechanism, etc.). In one embodiment, a high intensity target is easily replaceable.

In one embodiment, a high intensity target replacement is very different than conventional assembly/disassembly of the accelerator enclosure and removal/attachment of a target by a user. A high intensity target system and method can involve simple access to the target without involving other radiation components. The novel convenient configuration can enable the high intensity target systems and methods to efficiently and effectively execute the new replacement regimes.

In one exemplary implementation, replacement includes loading and unloading a high intensity target to and from an accelerator enclosure system. High intensity target loading and unloading can have various operational aspects (e.g., actions, features, components, characteristics, etc.).

The loading/unloading can include access activities (e.g., accessing a part of a radiation system, accessing an operational location, accessing an accelerator enclosure, etc.). The loading/unloading can also include activities associated with holding a high intensity target in a manner that prevents unintended movement (e.g., displacement, dislocation, dislodgement, etc.).

The different loading/unloading aspects of high intensity target systems and methods can include various implementations. One loading/unloading aspect is providing/taking away a high intensity target to/from an accelerator enclosure (e.g., a single target, multiple targets in a cartridge, etc.). Another loading/unloading aspect is injecting/ejecting an individual high intensity target into/out of an intended operational location (e.g., inside an accelerator enclosure, etc.). The different loading/unloading aspects can be implemented as actions or steps. The actions or steps can be implemented various ways (e.g., single actions, multiple actions, combined actions, separate action, continuous action, discrete, etc.).

In one embodiment, a user loads/unloads a single high intensity target in one continuous single step by accessing the operational location, ejecting a used high intensity target from the operational location, providing a new high intensity target by injecting it into the operational location, closing the access, and taking away/disposing the used high intensity target. In one exemplary implementation, the high intensity target is loaded/unloaded to or from a target holding component. The target holding component can move the high intensity target to an operational location and electron beam impact positions within the operational location.

In another embodiment, a user loads/unloads a plurality of high intensity targets in multiple separate distinct steps. In a first step a user provides a cartridge full of a plurality of high intensity targets to a radiation system and takes away a container with used high intensity targets. In some embodiments, later in separate distinct steps multiple openings/closings of an access to the operational location are implemented to allow insertion and ejection of the individual high intensity targets. When an access component permits access (e.g., is open, engaged, etc.) respective ones of the plurality of high intensity targets can be individually inserted in an operational location and respective used ones of the plurality of high intensity targets can be ejected out of the operational location into an ejection container. In one embodiment, after multiple high intensity targets have been ejected the ejection container can be easily removed from the accelerator enclosure. After a target has been inserted/ejected, an access component can deny/restrict access (e.g., is closed, disengaged, etc.) to the operational location. Additional detail is presented in other portions of this detail description section.

In one embodiment, a high intensity target is easily and readily replaceable. In one exemplary implementation, the ease at which a high intensity target can be loaded/unloaded enables the high intensity target to meet new replacement regime scheduling (e.g., associated with new operating conditions and parameter limitations, higher dose rates, etc.). In one embodiment, loading and unloading activities are effectively and efficiently executed. The loading and unloading can include simple/quick activities (e.g., single action, pushing in or pulling out of operational location, dropping into or lifting out of an operational location, etc.). In one exemplary implementation, effectively and efficiently executing loading/unloading includes inserting and ejecting a high intensity target to and from an operational location in under 30 minutes. In one exemplary implementation, effectively and efficiently executing loading/unloading includes inserting and ejecting a high intensity target to and from an operational location in under 5 minutes, including accessing the operational location in under 1 minute, inserting or ejecting to/from the operational location under 1 minute, placing a high intensity target in a holding component under 1 minute, and coupling a cartridge/magazine to the acceleration enclosure in under 1 minute. In one embodiment, the durations are indicative of times of activities executed in proximity of the radiation system. In one exemplary implementation, the coupling of a cartridge/magazine to the radiation system in under 1 minute addresses the time expended actually coupling the cartridge to the radiation system. The durations do not include additional time transporting/bringing the cartridge from a remote location (e.g., another room, storage location, another facility, etc.) to the radiation system or performing quality assurance (QA).

In one embodiment, high intensity target systems and methods are easily and readily implemented by an ordinary user. High intensity target systems and methods can be easy to understood/comprehended. High intensity target loading and unloading activities can be simple and intuitive (e.g., straight forward, not complicated, etc.). In one exemplary implementation, an ordinary user does not need sophisticated (e.g., extensive, specialized, rigorous, technical, etc.) characteristics (education, training, skills, expertise, physical attributes, etc.) to use the high intensity target loading/unloading systems and methods. While high intensity target loading/unloading systems and methods do not need users with sophisticated characteristics to load and unload high intensity targets, the users can have sophisticated characteristics. In one exemplary implementation, a user can have sophisticated characteristics in other areas that are not directly related to radiation system assembly/disassembly. A user (e.g., radiology technician, nurse, doctor, etc.) operating a radiation system can have other types of specialized characteristics (e.g., education, skills, knowledge, training, expertise, etc.) related to the operation of radiation systems and medical treatments.

It is also appreciated, that while high intensity target loading/unloading systems and methods can be easy and convenient, it does not preclude establishing restrictions/authorizations regarding the use of high intensity target loading/unloading systems and methods. While it is easy and convenient to load and unload high intensity targets in a radiation system, proper utilization of other features of the radiation system (e.g., generating radiation, medical treatments, etc.) can involve complicated and sophisticated aspects. In one embodiment, a high intensity target is utilized for important activities (e.g., medical treatments, procedures, etc.) having grave and severe consequences if not utilized appropriately. In one exemplary implementation, restriction/authorizations on using high intensity target loading and unloading systems and methods can be limited to certain users.

In one embodiment, a radiation accelerator system includes a target loading system configured to assist loading and unloading of high intensity targets to and from the accelerator system. The loading/unloading system can be configured to assist the insertion/ejection of a high intensity target to and from an operational location. It is appreciated that the terms high intensity target loading systems and methods are naming conventions that do not necessarily preclude unloading. In one exemplary implementation, high intensity target loading systems and methods can be utilized for both loading and unloading of a high intensity target. As indicated above, operational location access and holding a high intensity target to prevent unintended movement can be included in target loading systems and methods.

It is appreciated that high intensity target loading systems and methods can have various implementations. High intensity target loading systems and methods can be manual, automatic, combinations of manual and automatic (in which some of the loading/unloading is performed manually and some of the loading/unloading is performed automatically). In one embodiment, high intensity target systems and methods include mechanized assistance for manual loading/unloading. While the specification includes numerous paragraphs describing aspects of high intensity target loading systems and methods without explicitly indicating in that paragraph whether they are manual, automatic, or a combination of manual and automatic, nevertheless it is appreciated that aspects of high intensity target loading systems and methods can be manual, automatic, or a combination of manual and automatic.

In one embodiment, a target holding system can include holding components and methods that hold or restrict a high intensity target from un-intended movement. Loading and unloading (including injecting/ejecting) a high intensity target into/out of a target holding system can be easily/readily accomplished. In one embodiment, holding system/component activities (e.g., inserting, ejecting, etc.) are effectively and efficiently executed. In one embodiment, the insertion or ejection of a high intensity target to and from a holding component involves a simple/quick activity (e.g., single action, pushing in or pulling out of a holding component, dropping into or lifting out of a holding component, etc.). Target holding systems can include various efficient handling aids (e.g., handles, tabs, etc.) that assist various loading/unloading activity (e.g., grasping, grabbing clutching, seizing, griping, etc.). Holding systems can include various holding latches. The holding latches can assist holding the high intensity target in a proper position within the holding system. The holding latches can include an efficient (e.g., quick, simple, single action, etc.) release type component or action to engage/release the high intensity target (e.g., a clasp, clip, snap, latch, bolt, Velcro strip, door knob, handle, etc.). In one exemplary implementation, target holding system can enable a high intensity target to be loaded or unloaded in under 30 minutes. In one exemplary implementation, target holding system can enable a high intensity target to be loaded or unloaded in under 5 minutes.

Holding systems can include various additional features. Holding systems can include various sensors. The sensors can include position sensors that sense the location of a high intensity target in the holding system. The sensors can provide a signal indicating if a high intensity target is in a proper holding position or not. The sensors can have various configurations. In one exemplary implementation, a high intensity target can be loaded into a position that exerts a pressure/force and the sensor can sense the force/pressure. Based upon the pressure/force the sensor can determine a correlation with the position of the high intensity target. The sensor can be a light/laser based sensor that senses the location of high intensity target based upon impacts (e.g., reflection, interruption, etc.) on the light due to the position of the high intensity target. It is appreciated that various types of sensors can be utilized (electromagnetic/inductive, sound, optical, sensors that recognize features of a high intensity target, etc.). Additional discussion on high intensity target loading and unloading is presented in other portions of this detail description section. In one embodiment, a sensor provides information to the accelerator system. The accelerator system can prevent radiation generation and issue warnings to a user if the high intensity target is not in the proper position.

Figure 19:
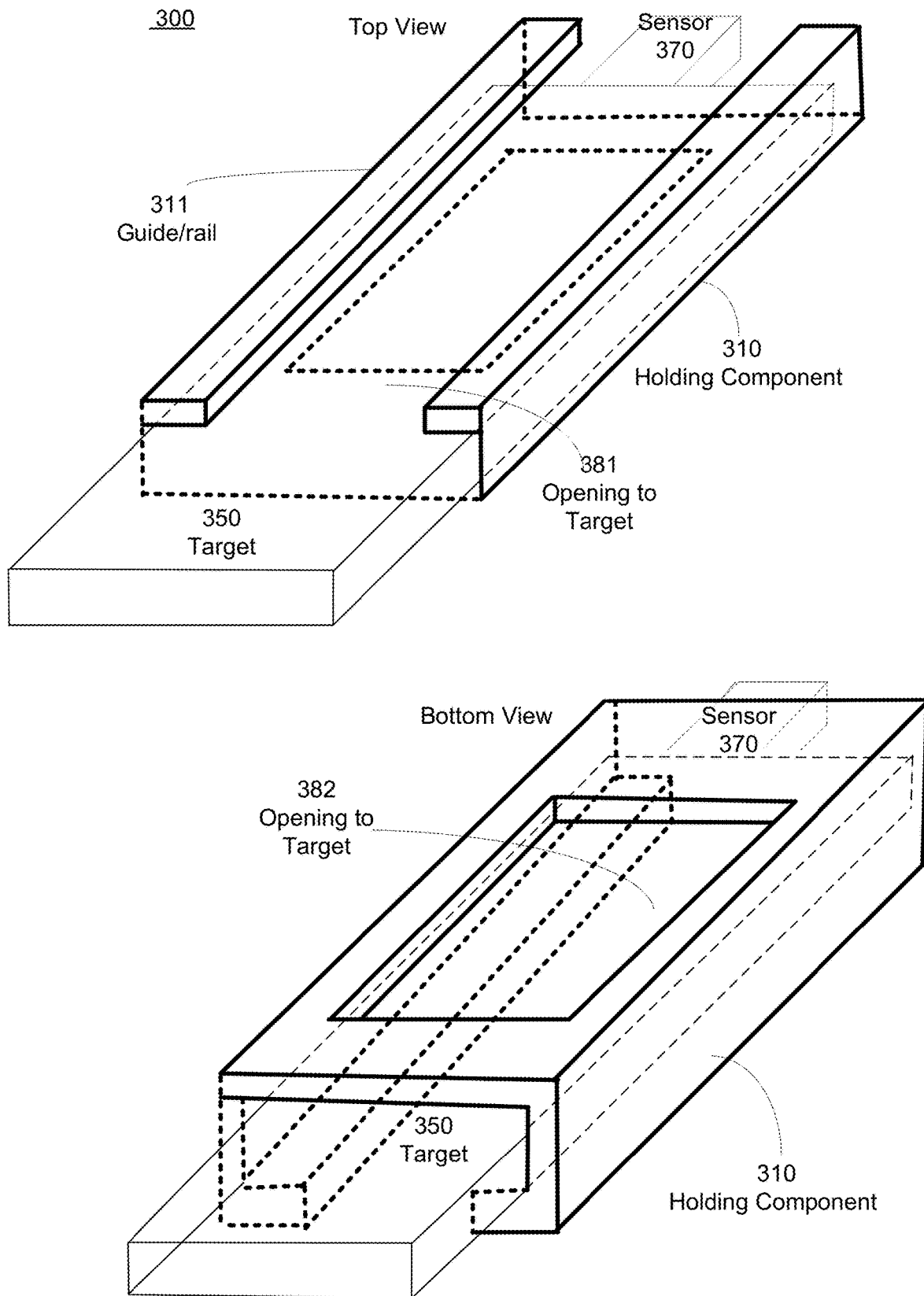
FIG. 19 is a block diagram of an exemplary holding system in accordance with one embodiment.

FIG. 19 is a block diagram of an exemplary holding system 300 in accordance with one embodiment. Holding system 300 includes holding component 310, openings 381 and 382, and sensor 370. Additional explanation of holding system 300 is presented in other portions of the detailed description.

FIG. 20 is a block diagram of an exemplary holding system 900 in accordance with one embodiment. Holding system 900 includes holding component 910, holding latch 917 and opening 988. Additional explanation of holding system 900 is presented in other portions of the detailed description.

Figure 21:
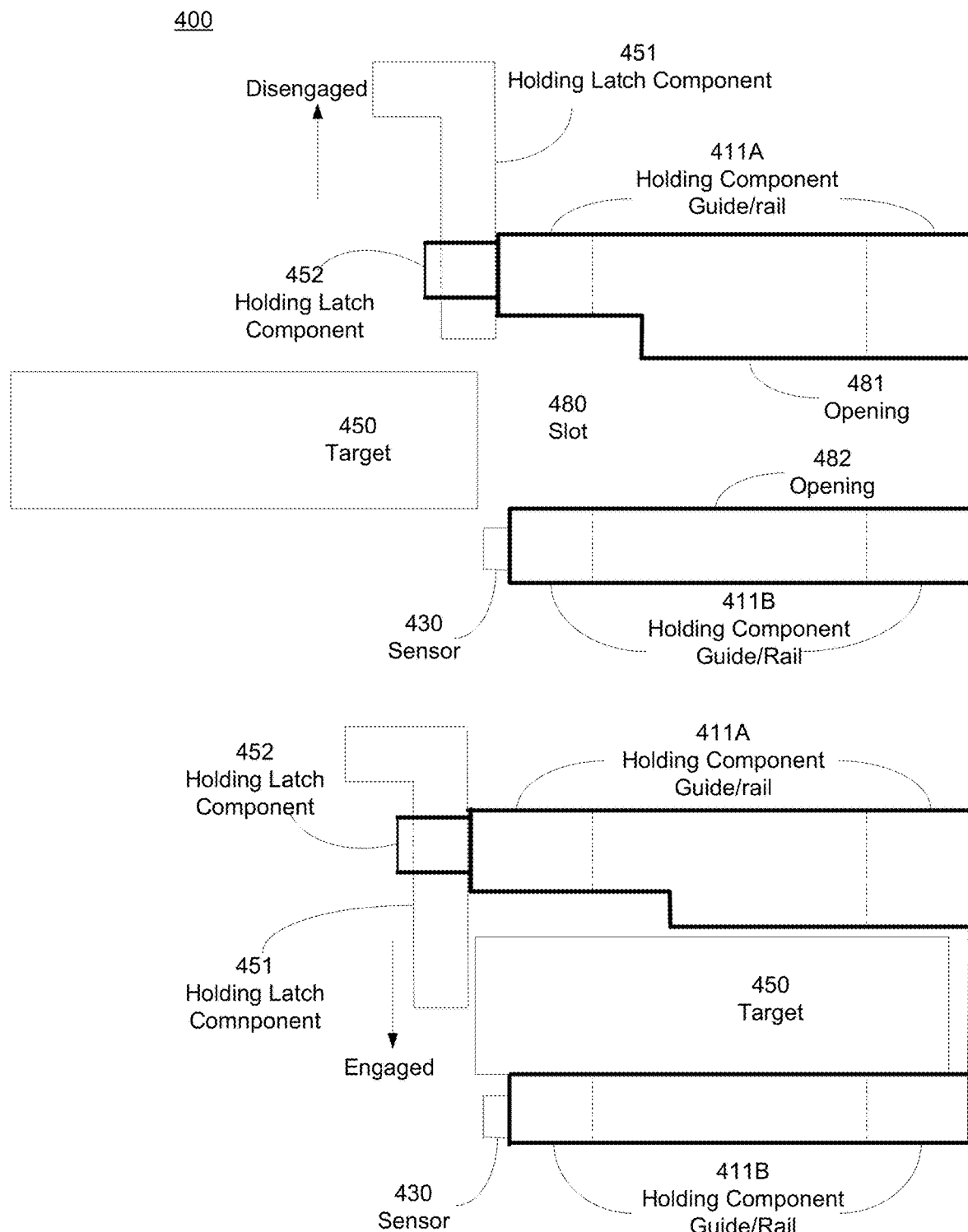
FIG. 21 is a block diagram of an exemplary holding system in accordance with one embodiment.

FIG. 21 is a block diagram of an exemplary holding system 400 in accordance with one embodiment. The holding system includes holding component 411 (shown as portions 411A and 411B), holding latch components component 451 and 452, and sensor 430. Additional explanation of holding system 400 is presented in other portions of the detailed description.

Figure 22A:
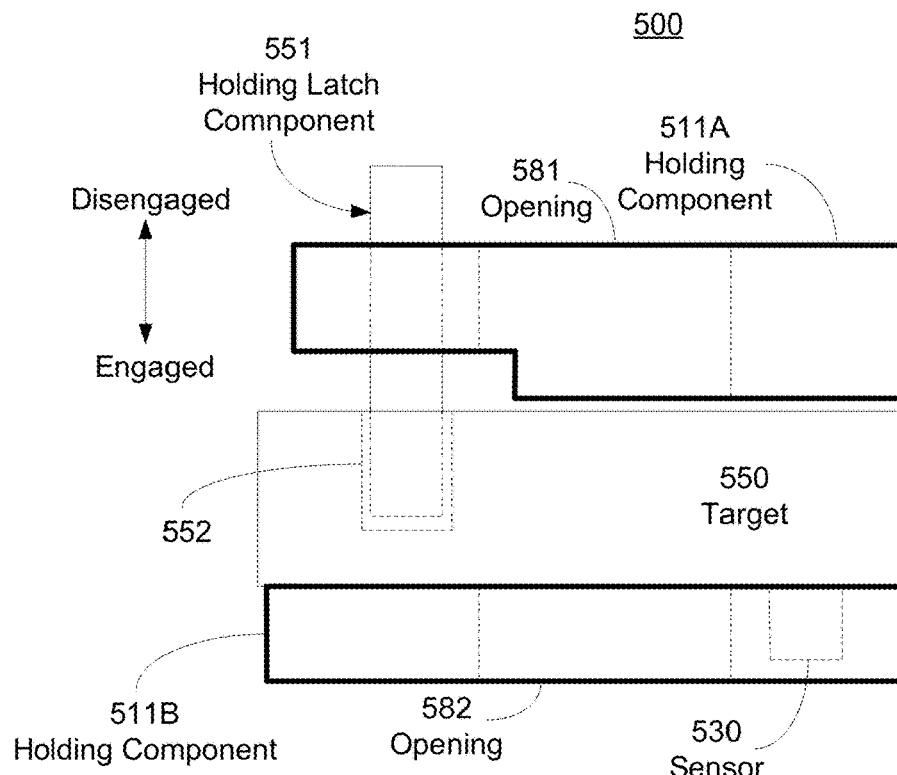
FIG. 22A is a block diagram of an exemplary holding system in accordance with one embodiment.

FIG. 22A is a block diagram of an exemplary holding system 500 in accordance with one embodiment. The holding system 500 includes holding component 511 (shown as portions 511A and 511B), holding latch component 551, and sensor 530. Additional explanation of holding system 500 is presented in other portions of the detailed description.

Figure 22B:
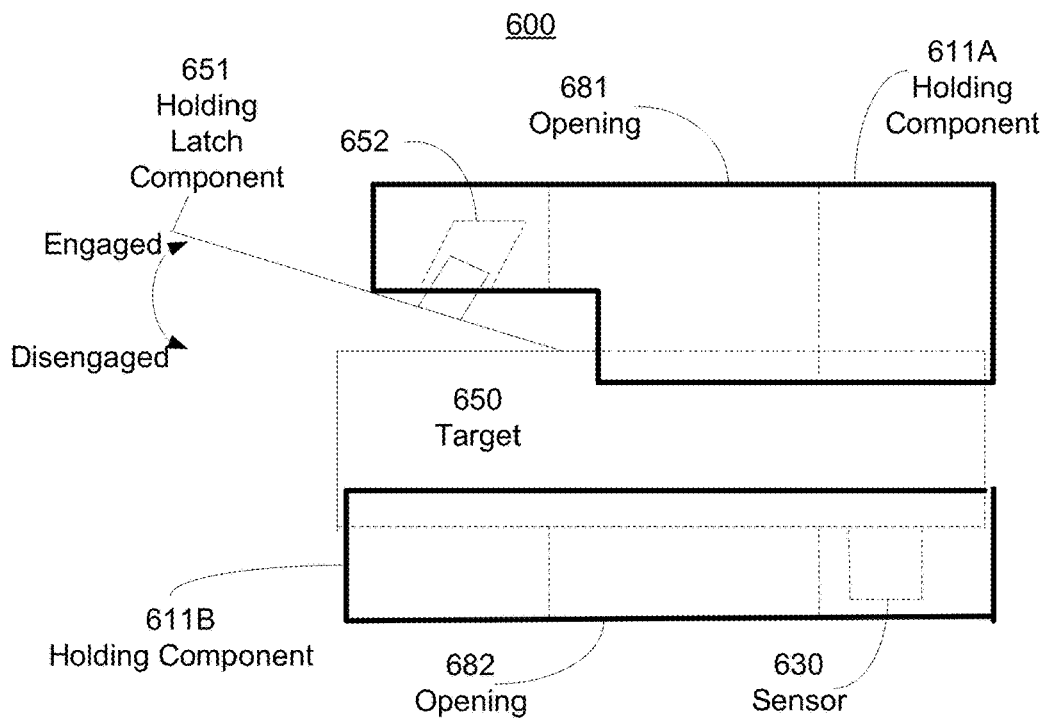
FIG. 22B is a block diagram of an exemplary holding system in accordance with one embodiment.

FIG. 22B is a block diagram of an exemplary holding system 600 in accordance with one embodiment. The holding system 600 includes holding component 611 (shown as portions 611A and 611B), holding latch component 651, and sensor 630. Additional explanation of holding system 600 is presented in other portions of the detailed description.

In one embodiment, a holding system include a holding component (e.g., 310, 910,411, 511, 611, etc.) that can be placed in and out of an operational location and hold or restrict a high intensity target (e.g., 350, 950, 450, 550, 650, etc.) from un-intended movement. In one exemplary implementation, a holding component can include features (e.g., a guard/rail configuration such as 311, a cavity configuration such as 911, support lip 912, a slot configuration such as 480, etc.) that help hold the high intensity target. Holding system loading and unloading activities (inserting, ejecting, etc.) can be effectively and efficiently executed (e.g., simple, quick, etc.). A high intensity target can easily be put in (e.g., slid in, dropped in, pushed in, etc.) and removed (e.g., lifted out, slid out, pulled out, etc.) out of a high intensity target holding component (e.g., 310, 910, 411, 511, 611, etc.). In one exemplary implementation, a high intensity target is inserted/ejected quickly (e.g., under 30 minutes, under 5 minutes, under 1 minute, under 10 seconds, etc.). It is appreciated that insertion/ejection time durations do not include time expended on other activities (e.g., performing radiation treatment, calibrating the radiation system, etc.). In one exemplary implementation with insertion/ejection times of under a minute, a high intensity target is inserted in an operational location in under a minute, patient radiation treatment lasts 1 hour, and the high intensity target is ejected from the operational location in under a minute.

Holding components/systems can be configured not to interfere with radiation generation. In one embodiment, holding components (e.g., 310, 910, 411, 511, 611, etc.) can include openings/spaces that enable the holding components to avoid undesirable impacts on radiation generation. In one embodiment, a hole/space/opening (e.g., 381, 481, 581, 681, etc.) can be configured to permit charged particle beams to hit a high intensity target and another hole/space (e.g., 382, 988, 482, 582, 682, etc.) can be configured to permit radiation beams to be emitted by the high intensity target (e.g., 350, 950, 450, 550, 650, etc.) without interference from/by holding component (e.g., 310, 910, 411, 511, 611, etc.).

Some portions of this specification describe high intensity target loading systems and methods without explicitly reciting some aspects of the loading/unloading so as to avoid unnecessarily obfuscating the invention. As previously indicated, various aspects of high intensity target loading systems and methods can be manual, automatic, or combinations of manual and automatic. In one embodiment, a high intensity target (e.g., 350, 950, 450, 550, 650, etc.) is inserted to and ejected from a holding component e.g., 310, 910, 411, 511, 611, etc.) manually. In one embodiment, a high intensity target (e.g., 350, 950, 450, 550, 650, etc.) is inserted to and ejected from a holding component (e.g., 310, 910, 411, 511, 611, etc.) automatically.

A holding component can include holding latch components (e.g., 917, 451, 452, 551, etc.) that help secure a target in the holding component. The latch components can be put in an engaged position and a disengaged position. In one embodiment, holding latch 917 can rotate to a disengaged position to allow replacement target 950 to be inserted (e.g., placed, dropped, etc.) into the target cavity 911 included in holding component 910 (e.g., see FIG. 20 top illustration, etc.) and holding latch 917 can rotate to an engaged position to hold replacement target 950 in place (e.g., see FIG. 20 top illustration, etc.). In one embodiment, a holding latch (e.g., 451, 551, etc.) can be put in a disengaged position to allow a replacement target to be inserted (e.g., placed, dropped, etc.) into the holding component (e.g., see FIG. 21 top illustration, etc.) and can be put in an engaged position to hold replacement target in place (e.g., see FIG. 21 bottom illustration, etc.). It is appreciated that a portion of a holding latch component (e.g., 551, 652, etc.) can be included in the holding component and a portion of a holding latch component (e.g., 562, 651, etc.) can be included in the high intensity target.

In one embodiment, a holding system can include a sensor (e.g., 370, 430, 530, 630, etc.) that senses the location of high intensity target 350. A sensor can have various configurations. In one exemplary implementation, a high intensity target collides with a sensor and a sensor senses forces/pressures from the collision. A sensor can be a light/laser sensor that senses the location of a high intensity target.

With reference back to FIG. 20, in one embodiment support lip 912 can act as a support/brace to support high intensity target 950 while still forming an opening/window 988. In one embodiment, support lip 912 can be moved/retracted allowing the high intensity target 950 to fall through. Alternatively, instead of support lip 912, the holding component 910 can include another or second holding latch (not shown) similar to holding latch 917 but on the opposite side of holding component. The second holding latch can be rotated to a first position that provides support for or holds the high intensity target 950 or second position that allows high intensity target 950 to fall through target cavity 911. In one embodiment, high intensity target 950 includes a handling aid (e.g., handle, tab, etc.) that aids insertion/ejection of high intensity target 950 to and from the holding system 900.

In one exemplary implementation, portions of holding latch component 551 and sensor 530 are incorporated in holding component 511. It is appreciated a high intensity target can include features that assist a holding latch component. In one embodiment, high intensity target 550 includes a cavity 552 to receive the pin or bolt portion of holding latch component 551. Holding system 500 loading and unloading activities can be effectively and efficiently executed. In one exemplary implementation, high intensity target 550 is inserted/ejected quickly (e.g., under 30 minutes, under 5 minutes, under 1 minute, etc.).

In one embodiment, a target loading system can include an operational location access system. The operational location access system can allow access to the accelerator system to insert/eject a high intensity target. There can be various access component configurations (e.g., a door, a drawer, etc.). In one exemplary implementation, accessing an operational location involves a simple motion (e.g., opening a door, opening a drawer, etc.). In one embodiment, completing access activities can also include an opposite motion (e.g., closing/shutting a door, closing a drawer, etc.). Access systems can include various access components and access latches. The access components can allow and restrict high intensity target entrance to and egress from an accelerator enclosure via an access portal (e.g., opening, slot, gap, etc.). The access latches can assist preventing un-intended access and/or entrance/egress. The access latches can include a quick release type component or action to engage/release the access component (e.g., a clasp, clip, snap, latch, bolt, hook and loop fabric strip, door knob, handle, magnetic, hook/loop, lever action, tensioner, detent, etc.). An access system loading and unloading activities can be effectively and efficiently executed. In one exemplary implementation, an access system can enable a high intensity target to be loaded or unloaded quickly (e.g., under 30 minutes, under 5 minutes, under 1 minute, etc.).

In one embodiment, a loading system has both an access system and a holding system. The access system allows access to a high intensity target operational location (e.g., within an accelerator system, etc.) to insert/eject a high intensity target and the holding system prevents un-intended movement of the high intensity target while in the operational location. In one exemplary implementation, the holding system can allow high intensity target movement to different positions within the target operational location (e.g., to change/move the electron beam impact location, etc.).

In one embodiment, an accelerator enclosure includes different types of access components. In one exemplary implementation, an accelerator enclosure includes an operational access component and an assembly access component. The operational access component is primarily intended for utilization in normal operation activities, including the normal replacement of a high intensity target. The assembly access component is primarily intended for utilization in general non-normal operations (e.g., general repair, maintenance, etc.). The general non-normal operations can include relatively rare/infrequent disassembly/assembly operations compared to operational access associated with normal high intensity target injection/ejection. In one embodiment, while a target could be loaded/unloaded via an assembly access component, the assembly access component is primarily intended for repairing/maintaining components (e.g., charged particle generation component, charged particle acceleration component, etc.) other than a high intensity target itself. While the assembly access component is not used primarily for allowing access to a target itself, an assembly access component can be the primary access to loading system components in an accelerator enclosure (e.g., for repair/maintenance of the loading component rather than injection/ejection of a target, etc.). In one exemplary implementation, an accelerator enclosure assembly access component can be utilized to clear a jammed/stuck high intensity target (e.g., a high intensity target that an operational access component cannot inject/eject, etc.).

In one embodiment, an operational access component enables access to an accelerator enclosure faster than an assembly access component. The operational access component can allow injection/ejection of a high intensity target in an accelerator enclosure faster than an assembly access component can place/remove a high intensity target in the accelerator enclosure. It is appreciated this detailed description refers to an access component as a shortened version of referencing an operational access component.

FIG. 23 is block diagram of an exemplary multiple access system 2000 in accordance with one embodiment. The illustrations in the upper portion of FIG. 23 show the exemplary accelerator enclosure access system 2020 in general. Accelerator enclosure access system 2020 includes access component 2022, access portal 2023, and access latching component 2024. In one embodiment, the insertion and ejection of a high intensity target via access system 2020 involves simple/quick activities. The access component 2022 is operated (e.g., opened, slid, pulled, activated, engaged, etc.) to allow access to the accelerator enclosure 2010 via access portal 783. In one embodiment, access component 2010 is a door slid in a first direction on door rail 784.

The illustration in the lower portion of FIG. 23 shows the exemplary accelerator enclosure access system 2020 included in a multiple access system 2000 in accordance with one embodiment. High intensity target 2090 is injected/inserted into accelerator enclosure 2010 via the access portal 2023 (e.g., slot, opening, etc.). In one exemplary implementation, high intensity target 2090 is injected/inserted into a target holding system 2033. When high intensity target 2090 is inserted to the proper operational location, the access component 2022 door is slid in a second direction to close the access component 2022. When the access component 2022 is in the proper access denial position, the access latching component 2024 is operated (e.g., engaged, activated, etc.). The access latch 2024 can assist preventing un-intended operation of the access component 2024. In one exemplary implementation, an accelerator enclosure access system can enable access to an accelerator enclosure in under 30 minutes. When the replacement high intensity target 2090 is in the proper operational location, the particle source 2031 can generate charged particles that are accelerated by acceleration portion 2032 towards the high intensity target 2090. When the radiation generation is finished, the access component 2022 can be opened and the high intensity target 2090 is removed/ejected from the accelerator enclosure. An accelerator enclosure access system loading and unloading activities can be effectively and efficiently executed. In one exemplary implementation, high intensity target 2090 is inserted/ejected quickly (e.g., under 30 minutes, under 5 minutes, under 1 minute, etc.).

With reference still to FIG. 23, accelerator enclosure 2010 also includes assembly plate 2015 in addition to access component 2022. Accelerator enclosure 2010 includes particle source 2031, acceleration portion 2032, and holding component 2033. Access component 2022 is part of an effective and efficient access system that allows quick and convenient injection and ejection of removable high intensive target 2090 to and from accelerator enclosure 2010. Assembly plate 2015 involves significantly more effort to gain access including loosening multiple screws/bots 2017. Assembly plate 2015 allows general access to multiple components (e.g., particle source 2031, acceleration portion 2032, holding component 2033, etc.) in the accelerator enclosure 2010.

In one embodiment, normal replacement high intensity target loading system activities are conducted via access component 2022 and assembly plate 2015 is utilized primarily as a backup access in special situations (e.g., emergency requiring more access then access component, access component 2012 is broken, etc.) or for general maintenance. In one embodiment, assembly plate 2015 can also allow emergency or maintenance access to inject and eject high intensity target 2090. In one exemplary implementation, assembly plate 2015 can be utilized to inject and eject high intensity target 2090 if something goes wrong with the loading system (e.g., access component 2022, holding component 2033, etc.).

Figure 24:
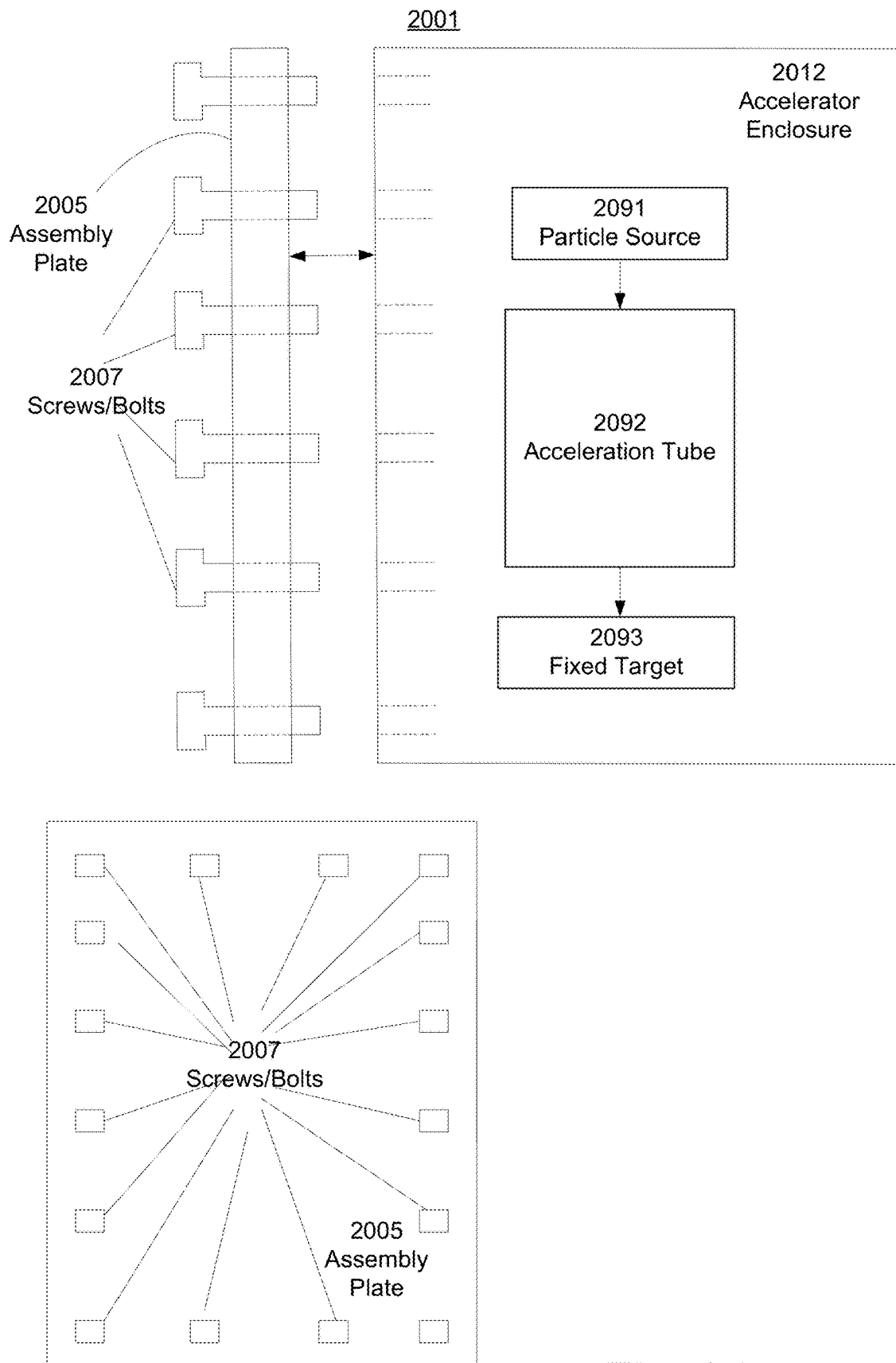
FIG. 24 is block diagram of an exemplary traditional system in accordance with one embodiment.

FIG. 24 is block diagram of an exemplary traditional system 2001 in accordance with one embodiment. Traditional system 2001 is limited to a single access via assembly plate 2005. Traditional system 2010 includes accelerator enclosure 2002 and assembly plate 2005. Accelerator enclosure 2002 includes particle source 2091, acceleration tube 2092, and fixed target 2093. The access to accelerator enclosure 2002 is complicated and ridged access. Assembly plate 2005 involves significantly more effort to gain access to the fixed target 2093 including loosening multiple screws/bolts 2007.

Assembling and disassembling fixed target 2093 also involves significant effort and energy. A traditional fixed target is typically configured to resist movement and separation and therefore disassembling/removing an old traditional target and assembling/attaching a different traditional target can be the opposite of easy and simple. In one embodiment, fixed target 2093 is attached in the accelerator enclosure 2011 with multiple screws/bolts (not shown). In one embodiment, the restricted space and limited operating area within accelerator enclosure 2002 makes manipulating multiple fixed fastener screws very difficult. Given that removal of assembly plate 2015 enables access to more (e.g., particle source 2091, acceleration tube 2092, etc.) than just fixed target 2093, actions to remove fixed target 2093 from within the acceleration enclosure are much more complex with potential for much greater problems/accidents than the easy and convenient access component.

Figure 25:
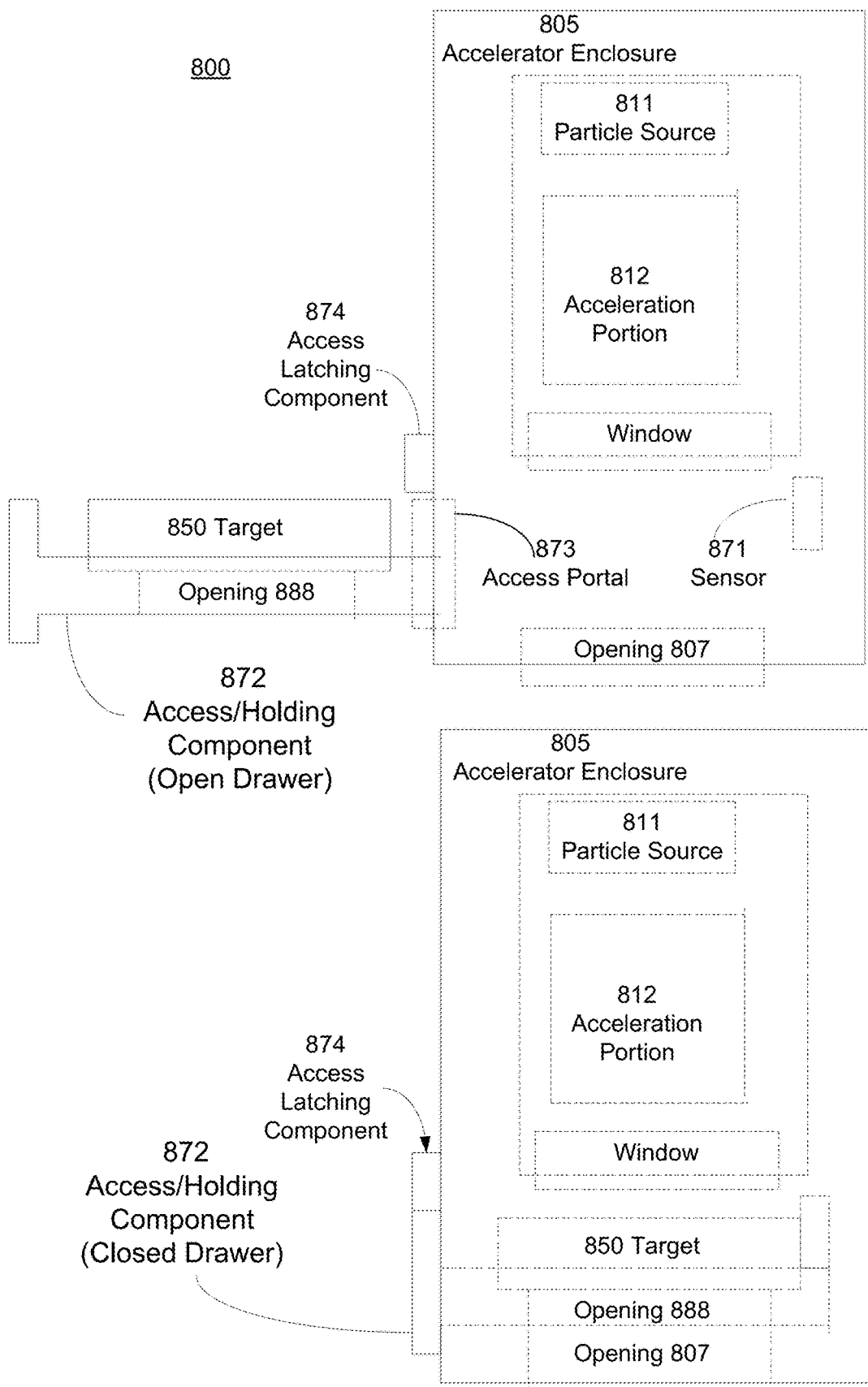
FIG. 25 is a block diagram of an exemplary accelerator enclosure access system in accordance with one embodiment.

FIG. 25 is a block diagram of an exemplary accelerator enclosure access system 800 in accordance with one embodiment. Accelerator enclosure access system 800 includes an access/holding component 872, access portal 873, and access latching component 874. In one embodiment, the insertion and ejection of a high intensity target 850 via access system 800 involves simple/quick activities. The access/holding component 872 is operated (e.g., opened, slid, pulled, activated, engaged, etc.) to allows access to the accelerator enclosure 805 system via access portal 873. The access/holding component 872 can also act as a holding component that holds or restricts high intensity target 850 from un-intended movement. In one embodiment, access component/holding component 872 is a drawer that is slid in a first direction to be exposed outside the accelerator enclosure 805. Removable high intensity target 850 is injected/inserted into access/holding component 872. Then the access/holding component 872 is slid in a second direction to be injected inside the accelerator enclosure 805. When the access component 872 is in the proper closed position, the access latching component 874 can be operated (e.g., engaged, activated, etc.). The access latching component 874 can assist in securing the access access/holding component 872. The access latching component 874 can include a simple/quick release type component or action to engage/release the access component.

When the replacement high intensity target 850 is in the proper position, the particle source 811 can generate charged particles that are accelerated by acceleration portion 812 towards the high intensity target 850. The high intensity target 850 can generate Bremsstrahlung radiation in response to impacts by the charged particles. In one embodiment, the access/holding component 872 can include opening 888/(e.g., similar to opening 381,382 in FIG. 19, etc.). The radiation (e.g., x-rays, photons, etc.) provided by high intensity target 850 can leave the access/holding component 872 via the opening/window 888 and proceed towards leaving the accelerator enclosure 805. In one exemplary implementation, the accelerator enclosure can also include an accelerator enclosure opening 807 which the radiation travels through when leaving the accelerator enclosure 805. When the radiation generation is finished, the access/holding component 872 can be opened/withdrawn from the accelerator enclosure 805 and the replacement high intensity target 850 removed/ejected from the accelerator enclosure. Accelerator enclosure access system 800 loading and unloading activities can be effectively and efficiently executed. In one exemplary implementation, high intensity target 850 is inserted/ejected quickly (e.g., under 30 minutes, under 5 minutes, under 1 minute, etc.). In one embodiment, the loading and unloading activities time duration does not include the time duration of generating Bremsstrahlung radiation.

Figure 26A:
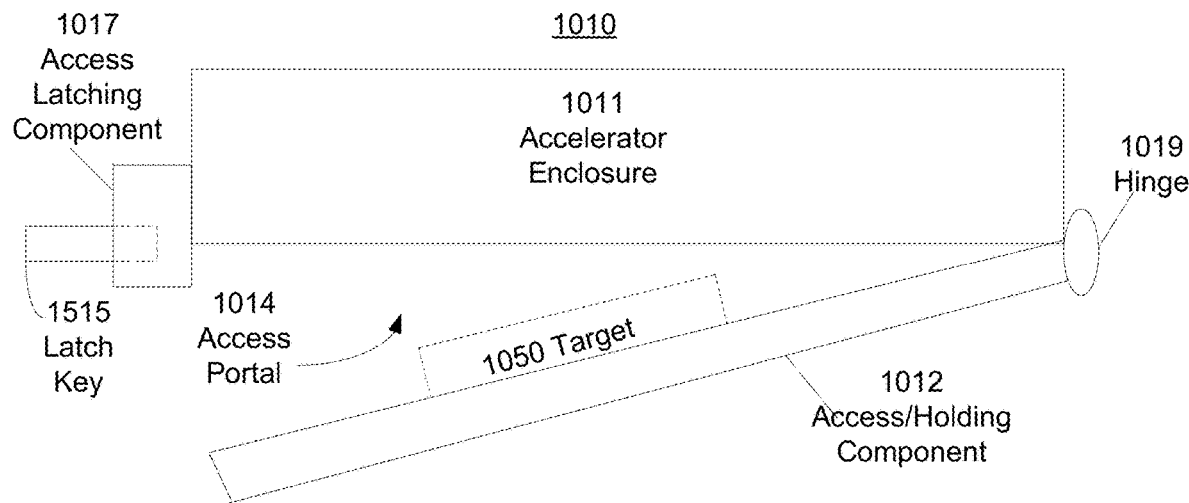
FIG. 26A includes a block diagram of an exemplary door type configuration access/holding system and method in accordance with one embodiment.
Figure 26B:
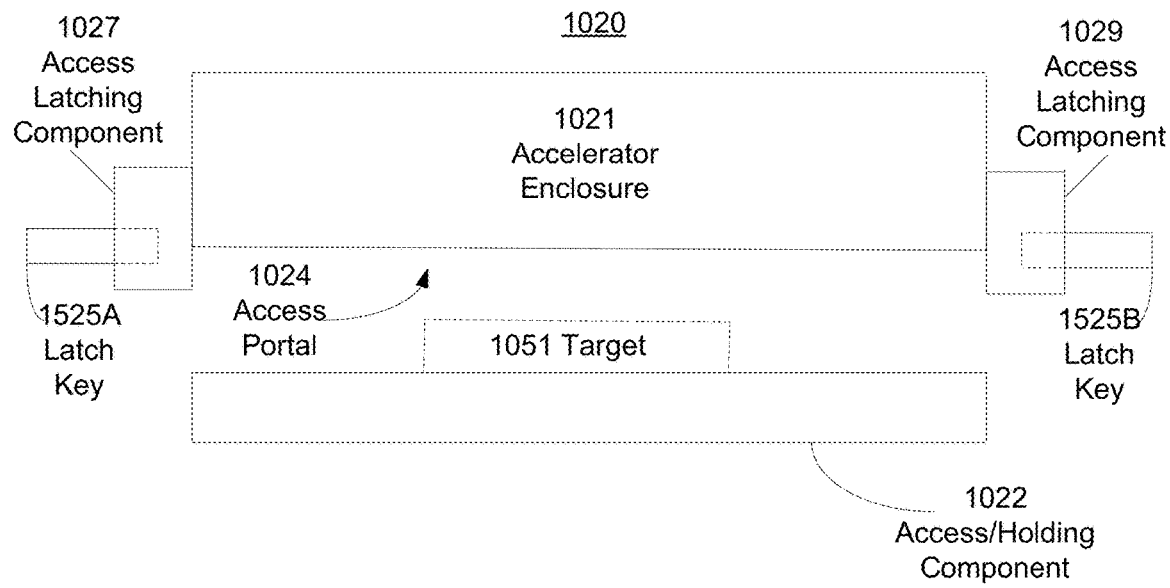
FIG. 26B includes a block diagram of another exemplary door type configuration access/holding system and method in accordance with one embodiment.

It is appreciated that holding systems, access systems, and combinations of both can be implemented in various configurations with various components. FIG. 26A includes a block diagram of an exemplary door type configuration access/holding system and method in accordance with one embodiment. Door type configuration 1010 includes acceleration enclosure 1011, access portal 1014, access component/holding component 1012 (e.g., a door, etc.), access component hinge 1019, and access latch component 1017. FIG. 26B includes a block diagram of another exemplary door type configuration access/holding system and method in accordance with one embodiment. Door type configuration 1020 includes accelerator enclosure 1021, access portal 1024, access/holding component 1022 (e.g., a door), and access latch components 1027 and 1029. A door type access can be implemented on a top, bottom, or other side of a radiation chamber.

In one embodiment, the insertion and ejection of a high intensity target via access systems 1010 and 1020 involves simple/quick activities. In one exemplary implementation, an access latching component (e.g., 1017, 1027, etc.) can be put in a first configuration (disengaged, opened, etc.) that allows the access/holding component (1012, 1022) to open and allow access to accelerator component (e.g., 1011, 1021, etc.) via an access portal (e.g., 1014, 1024, etc.) Access/holding component 1012 can rotate on hinge 1016 and access component 10122 to be moved away. In one embodiment, a removable high intensity target can be inserted into/ejected from an operational location (e.g., within an accelerator enclosure 1011, 1021, etc.). In one exemplary implementation, a high intensity target can be directly inserted into the operational location. In another exemplary implementation, a removable high intensity target 1050 can be placed on an access/holding component (e.g., 1012, 1022, etc.) and then inserted into the operational location (e.g., within accelerator enclosure 1011, etc.). The access/holding component (e.g., 1012, 1022, etc.) can be put in a closed position denying/restricting access to an operational location and an access latching component (e.g., 1017, 1525A, 1525B, etc.) can be put in a second configuration (e.g., engaged, close, etc.) that restricts the access component (e.g., 1012, 1022, etc.) from unintended opening.

Access system (e.g., 1010, 1020, etc.) loading and unloading activities can be effectively and efficiently executed. In one exemplary implementation, a high intensity target is inserted/ejected quickly via configurations 1010 and 1020 (e.g., under 30 minutes, under 5 minutes, under 1 minute, etc.). In one embodiment, latch lock systems can be included in systems similar to the door type configurations in FIGS. 26A and B. A latch key component (e.g., 1015, 1025A, 1025B, etc.) can be used to lock and restrict/prevent a latch component (e.g., 1017, 1027, 1029, etc.) from being opened, and can be used to unlock and allow the lock latch component to be open.

It is appreciated that hold latches and access latches can be compatible with various types of latching approaches. The latch activities can be effectively and efficiently executed. The latching activities can include simple/quick activity/action. In one embodiment, a latch can be configured as a clasp latch, draw latch, cam latch, draw or toggle latch, spring latch, Norfolk latch, Suffolk latch, crossbar latch, and so on. In one embodiment, the hold latches and access latches can latch/unlatch (e.g., close, open, engage/disengage, etc.) in response to a single action/motion. In one embodiment, the hold latches and access latches can latch/unlatch (engage/disengage) in response to two actions/motions. In one exemplary implementation, a latch/unlatch (engage/disengage) takes less than 5 minutes. In one exemplary implementation, a latch/unlatch (engage/disengage) takes less than 15 seconds. In one embodiment, the durations are indicative of times of activities directly associated with executing latch activity (e.g., closing/engaging, opening/disengaging the latch, etc.). In one exemplary implementation, the durations do not include additional time for other activities (e.g., transporting/bringing the cartridge from a remote location, another room, storage location, another facility, etc.) to the radiation system.

Figure 27A:
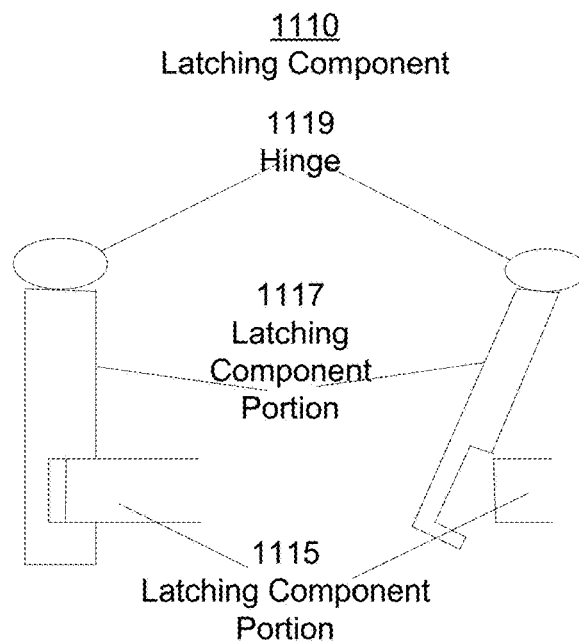
FIG. 27A is a block diagram of an exemplary latching component in accordance with one embodiment

FIG. 27A is a block diagram of an exemplary latching component 1110 in accordance with one embodiment. Latching component 1110 includes latching component portions 1117 and 1115. Latching component portion 1117 can include a hinge 1119. In one exemplary implementation, the latching component 1110 is considered similar to a cabin latch. The illustration on the left in FIG. 27A shows latching component 1110 engaged and illustration on the right shows latching component 1110 disengaged.

Figure 27B:
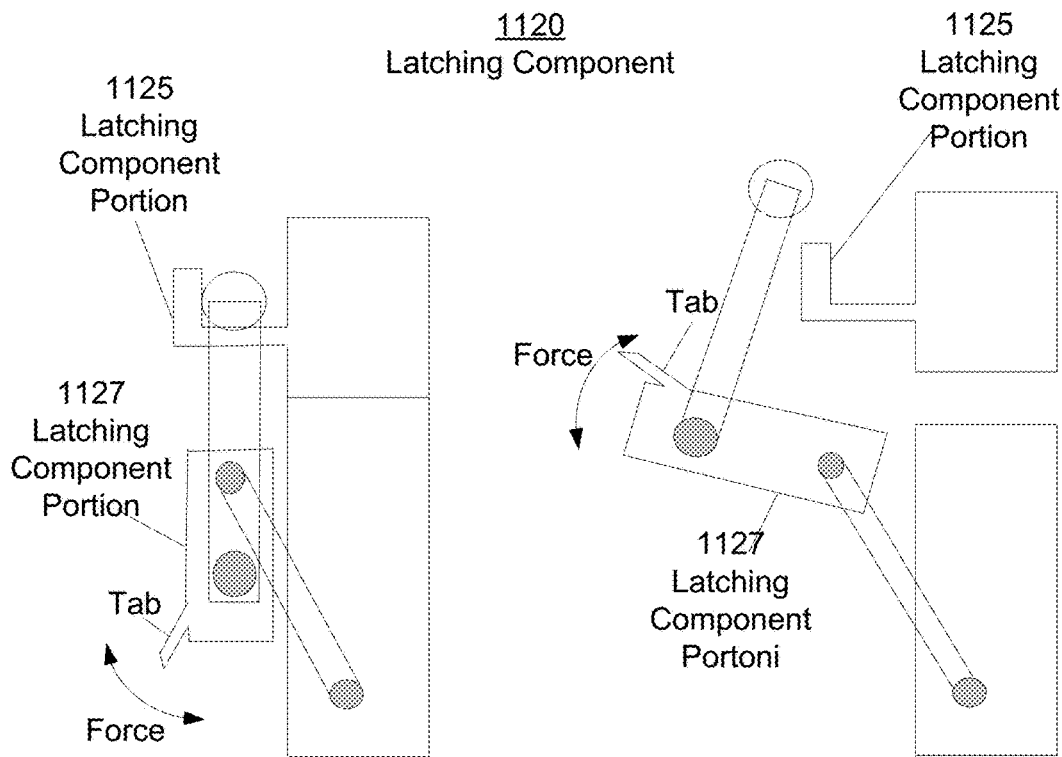
FIG. 27B is a block diagram of an exemplary latching component in accordance with one embodiment.

FIG. 27B is a block diagram of an exemplary latching component 1120 in accordance with one embodiment. Latching component 1120 includes latching component portions 1127 and 1125. In one exemplary implementation, the latching component 1120 can be considered similar to a clasp latch, draw latch, toggle latch, and so on. Latching component portion 1127 can include a tap or handle. The illustration on the left in FIG. 27B shows latching component 1120 engaged and illustration on the right shows latching component 1120 disengaged.

Figure 28:
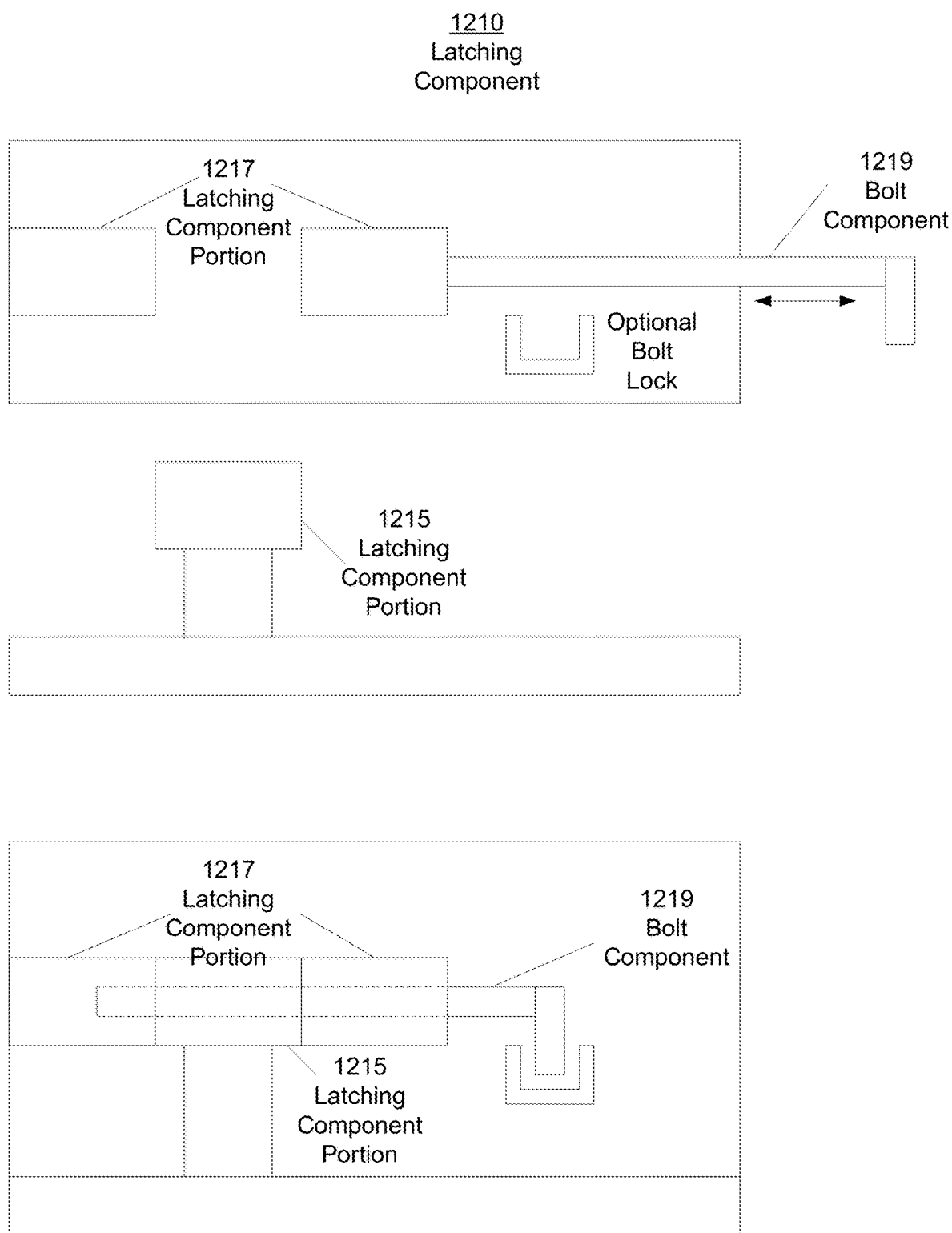
FIG. 28 is a block diagram of an exemplary latching component in accordance with one embodiment.

FIG. 28 is a block diagram of an exemplary latching component 1210 in accordance with one embodiment. The latching component 1210 includes latching component portion 1217, latching component portion 1215, and bolt component 1219. In one embodiment, latching component 1210 is considered a bolt latch. Bolt component 1219 can be slid in a first direction to be disengaged (top illustration of FIG. 28) with latching component 1215 and latching component 1217 and in the opposite direction to be engaged (bottom illustration of FIG. 28. When engaged latching component portion 1215 is effectively secured to latching component 1217 and when disengaged latching component portion 1215 can be separated from the latching component portion 1217. In one exemplary implementation, latch component 1210 can include an optional bolt lock portion that prevents unintended movement of the bolt (bottom illustration) or allows movement of the bolt (top illustration).

Figure 29:
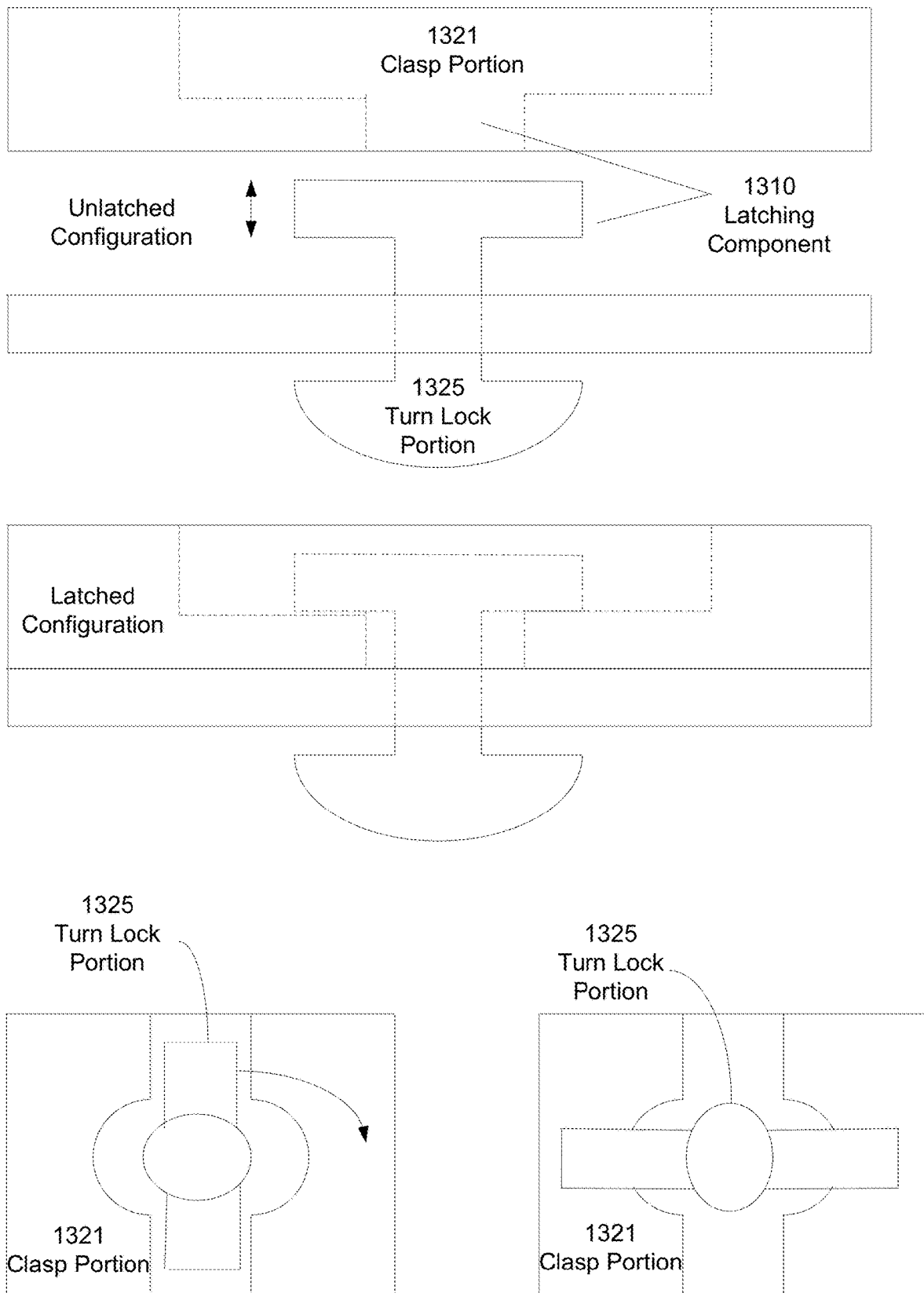
FIG. 29 is a block diagram of an exemplary latching component in accordance with one embodiment.

FIG. 29 is a block diagram of an exemplary latching component 1310 in accordance with one embodiment. The latching component 1310 includes latching component portion 1325 and latching component portion 1321. The top illustration is a side view showing an unlatched or open configuration in which latching component portion 1325 and latching component portion 1321 are disengaged and separated. The middle illustration is a side view showing a latched or closed configuration in which latching component portion 1325 and latching component portion 1321 are engaged and coupled together. The bottom left illustration is a top view showing the latching component portion 1325 inserted into the opening/slot of latching component portion 1321. The bottom right illustration is a top view showing the latching component portion 1325 rotated (e.g., 90 degrees, 45 degrees, etc.) to engage/couple with the latching component portion 1321 in an engaged/closed configuration. In one embodiment, latch component 1310 is considered a turn lock clasp latch. In one exemplary implementation, latching component portion 1325 is the turn latch portion and latching component portion 1321 is the clasp portion. In one exemplary implementation, a turn lock latch is slid in one direction and then rotated to complete the latching/unlatching in a single action.

In one embodiment, a tool can be utilized to perform various activities associated with loading and unloading a high intensity target to/from an accelerator system. In one exemplary embodiment, a tool is considered a special tool and intended to be unique or dedicated to those activities and not intended for general or other use. In one exemplary implementation, a tool is associated with/utilized for latch operations (e.g., engage/close, disengage/open, etc.). In one embodiment, the tool can act as a key that locks/unlocks a latch.

In one embodiment a special tool can be utilized in latching activities (e.g., opening a latch, closing a latch, etc.). In one exemplary implementation, a special tool has a particular configuration. It is appreciated various special tools and approaches are compatible with loading and unloading activities associated with a high intensity target. The special tool can be considered dedicated primarily for use with a latching component, as opposed to a general tool than can have multiple general uses. Additional discussion on use of a general tool configuration is set forth in other portions of this specification. Utilizing a special tool for latching can involve simple/quick activities. In one exemplary implementation, the special tool has an uncommon/distinctive configuration that engages with (e.g., matches, mates, selectively couples to, activates, etc.) a latching component. Operation of the latch can be limited to coordination with and use of the special tool. In one embodiment, a latch can be located in a cordoned off area/location and operation of the latch can be limited to coordination with and use of the special tool. Possession/use of the special tool can be restricted to particular users (e.g., qualified users, authorized users, etc.). Special tool user restrictions can promote considerations beyond (e.g., proper use, operational reliability, regulations compliance, etc.) direct latching functions.

Figure 30:
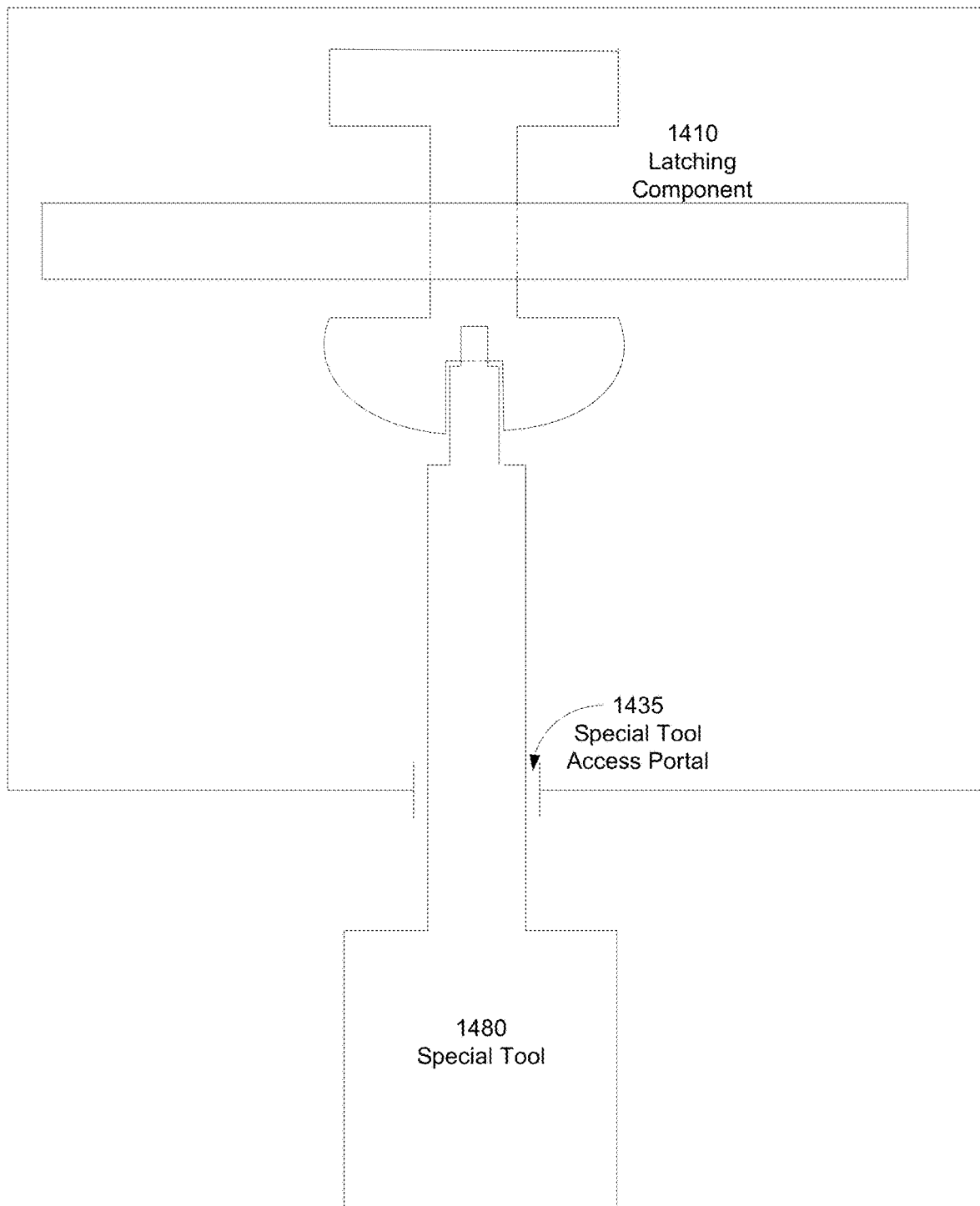
FIG. 30 is a block diagram of a loading system tool system in accordance with an embodiment.

FIG. 30 is a block diagram of a loading system tool system 1420 in accordance with an embodiment. In one exemplary implementation, the loading system tool 1480 has a head configuration that matches/mates with a latching component 1410. In one exemplary implementation, the latching component 1410 is similar to a turn lock clasp or latching component 1310. Latching component 1410 can be enclosed with just a tool access portal 1435 that allows for coordination and use of the tool 1480 to operate the latching component 1410.

In one embodiment, a latch can include a lock feature that allows/prevents engagement and disengagement of the latch component. In one exemplary implementation, a key can be used to lock/unlock the latch component. The lock and key can be used to (e.g., provide security, restrict unauthorized activity, reduce improper replacement of a high intensity target, etc.). Utilizing a latch lock and key can involve simple/quick activities. It is appreciated various lock components and approaches are compatible with loading and unloading activities associated with a high intensity target. The key can be a mechanical key, a digital key, biometric key, and so on. The lock can include status indication features that indicate the status of the lock (e.g., locked, unlocked, attempted locking/unlocking action, tampering, etc.). The status can be indicated locally and remotely. The status can trigger alarms/warmings local and remotely. A key can be unique to a particular radiation system or group of radiation systems (e.g., model/models of radiation system, an organization, a medical treatment facility, etc.).

In one embodiment, a latching component and latch lock can be effectively and efficiently used. In one exemplary implementation, a latching component and latch lock can be used to latch/unlatch a latching component quickly and easily (e.g., under 30 minutes, under 5 minutes, under 1 minute, etc.).

It is appreciated that features and components of high intensity target systems and methods may be shown in a particular orientation, the features and components can also be implemented in other configurations. In one embodiment, access, holding, and latching components may be shown (e.g., FIGS. 19-34, etc.) in a first orientation (e.g., vertical etc.), and the access, holding, and latching components can also be implemented in a second orientation (e.g., horizontal, etc.).

Operational location access components and target holding components can include components/features that assist with a high intensity target inserting and ejecting activity. In one exemplary implementation, assisting with an inserting and ejecting activity of a high intensity target includes supplying assistance (e.g., force, energy, power etc.) to accomplish the insertion or ejection of a high intensity target to/from an operational location.

Figure 31:
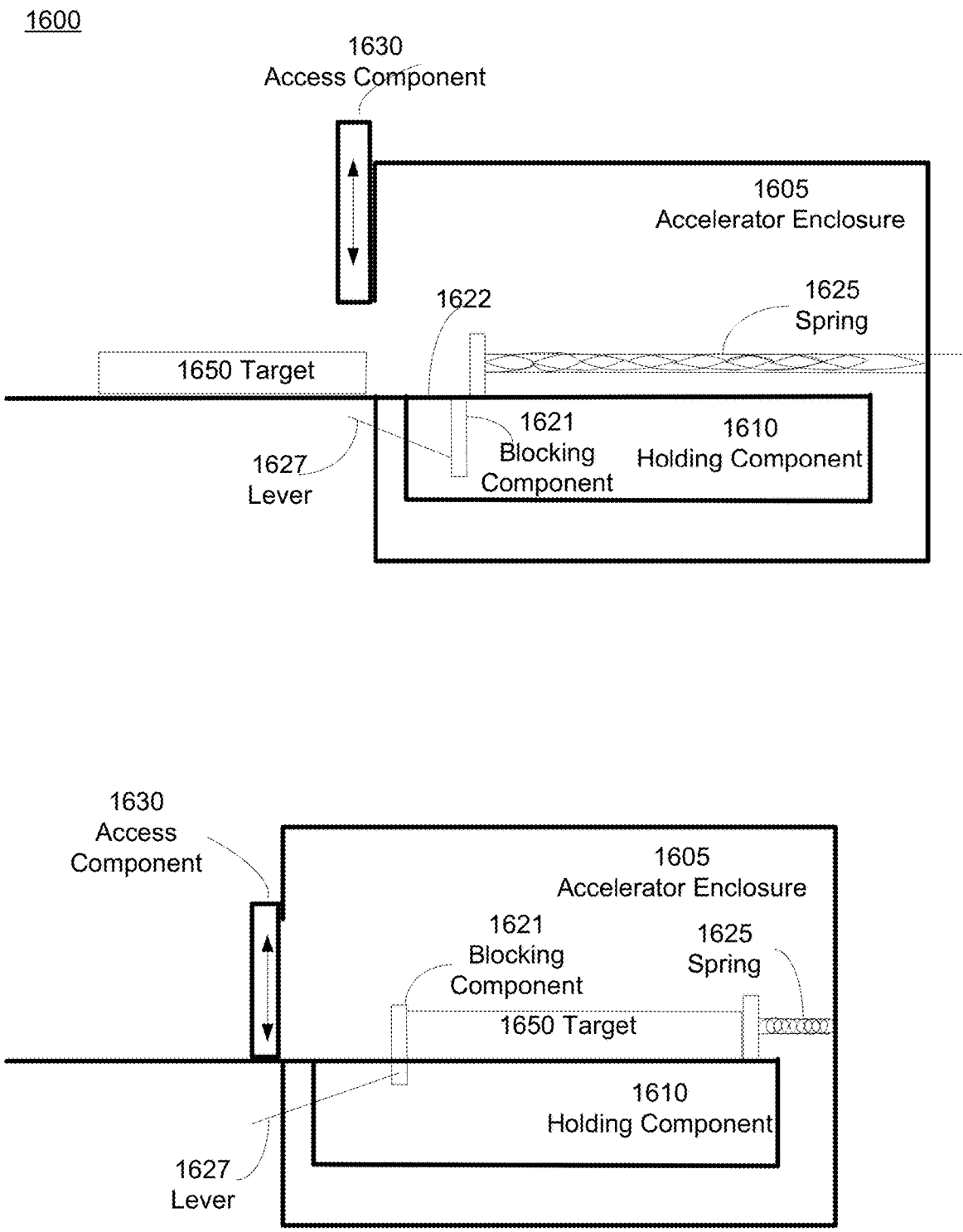
FIG. 31 is a block diagram of an exemplary target injection/ejection system in accordance with one embodiment.

FIG. 31 is a block diagram of an exemplary target injection/ejection system 1600 in accordance with one embodiment. Target injection/ejection system 1600 includes holding component 1610 and access component 1630. Access component 1630 is configured to allow/restrict access to accelerator enclosure 1605. In one embodiment, access component 1630 is in a horizontal orientation and operates similar to access component 2020 in FIG. 23. In one embodiment, blocking component 1621, and spring plate 1625 are considered part of holding component 1610. When the access component 1630 is open a high intensity target 1650 can be inserted to/ejected from holding component 1610. The top illustration shows the target 1650 outside of and ejected from the accelerator enclosure 1605. When the blocking component 1621 is engaged/activated (e.g., by lever 1627, etc.) it prevents/restricts the target 1650 movement (e.g., insertion, ejection, unintended movement) and when the blocking component 1621 is disengaged/deactivated it allows the target 1650 movement. Blocking component 1621 can be engaged/disengaged by various mechanisms (e.g., a lever, a button, a special tool, key, etc.). To insert the target 1650, the access component 1630 is engaged/opened, the blocking component 1621 is disengaged, target 1650 is pressed up against the spring plate 1623, which in turn allows the target to move over the floor 1622 while compressing the spring 1625 at the same time. The floor 1622 can have a window/opening similar to the window/opening 911 in holding component 910 (shown in FIG. 20). When the target 1650 is in the proper location blocking component 1621 is engaged preventing/restricting improper movement of target 1650 and the access component 1630 is shut. The bottom illustration in FIG. 31 shows the target in a proper position inside the accelerator enclosure for radiation generation. To eject the target 1650, the access component 1630 is opened, the blocking component is disengaged/released and the spring associated with spring plate 1625 expands forcing the target 1650 out through the access component 1630. In one exemplary implementation, spring plate 1625 assists with an ejection, including supplying assistance (e.g., force, energy, power etc.) to accomplish the ejection of high intensity target 1625 from accelerator enclosure 1605.

In one embodiment, a tool can be used to assist with an inserting and ejecting action of a high intensity target. In one exemplary implementation, assisting with an inserting and ejecting action of a high intensity target includes supplying assistance (e.g., force, energy, power etc.) to accomplish the insertion or ejection of a target from a radiation system/chamber.

Figure 32:
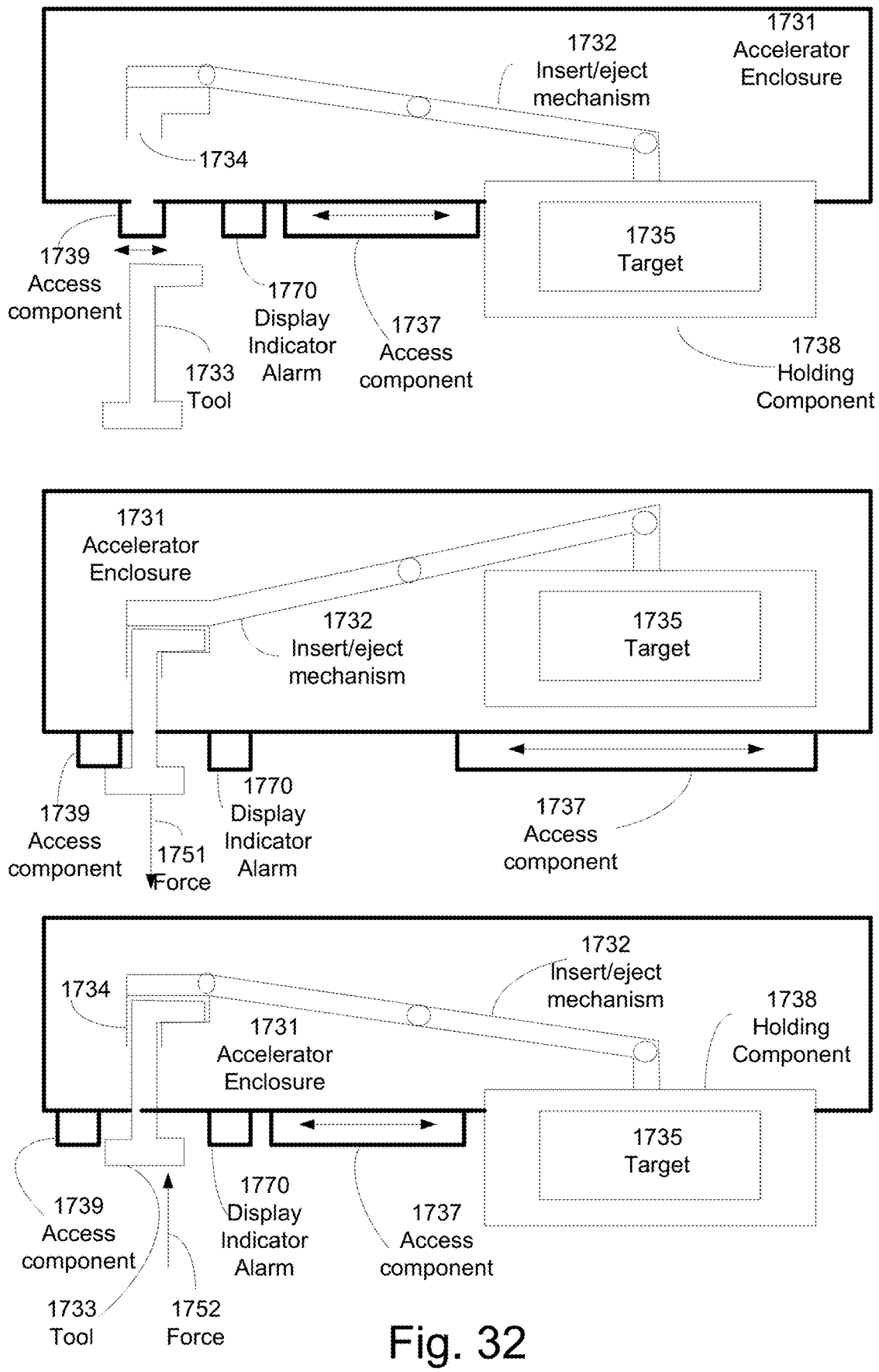
FIG. 32 is a block diagram of an exemplary loading system in accordance with an embodiment.

FIG. 32 is a block diagram of an exemplary loading system in accordance with an embodiment. The loading system includes access component 1737, access component 1739, holding component 1738, inert/eject mechanism 1732, tool 1733, and display indicator/alarm 1770. The loading system features help/assist with injecting and ejecting a high intensity target 1735 in and out of accelerator chamber 1731. In the top illustration, the tool 1733 and holding component 1738 are shown outside the accelerator enclosure 1731. High intensity target 1735 is put in holding component 1738. In the middle illustration, access component 1739 is opened and the tool 1733 is manipulated to engage the inert/eject mechanism 1732. A force 1751 is applied to the tool 1733 causing high intensity target 1735 to be inserted in the accelerator enclosure 1731 and placed in an operational location. Tool 1733 can be removed from accelerator enclosure 1731, access component 1737 closed, and a radiation treatment operation performed. In one embodiment, there is also a target control/movement system (e.g., similar to 119, 3100, etc.) configured to change positions of high intensity target 1735 within the operational location (e.g., causing an electron beam impact location on high intensity target 1735 to change, etc.). Insert/eject mechanism 1732 can be part of the target control/movement system. In the bottom illustration, access component 1737 is opened and another force 1752 is applied to the tool 1733 resulting in high intensity target 1735 being ejected from the accelerator enclosure 1731. Display indicator/alarm 1770 can convey information regarding the loading system status and operations, including indicating if there are issues. It is appreciated various different tools can be utilized (e.g., general/standard tool, special tool, a key, etc.).

Figure 33:
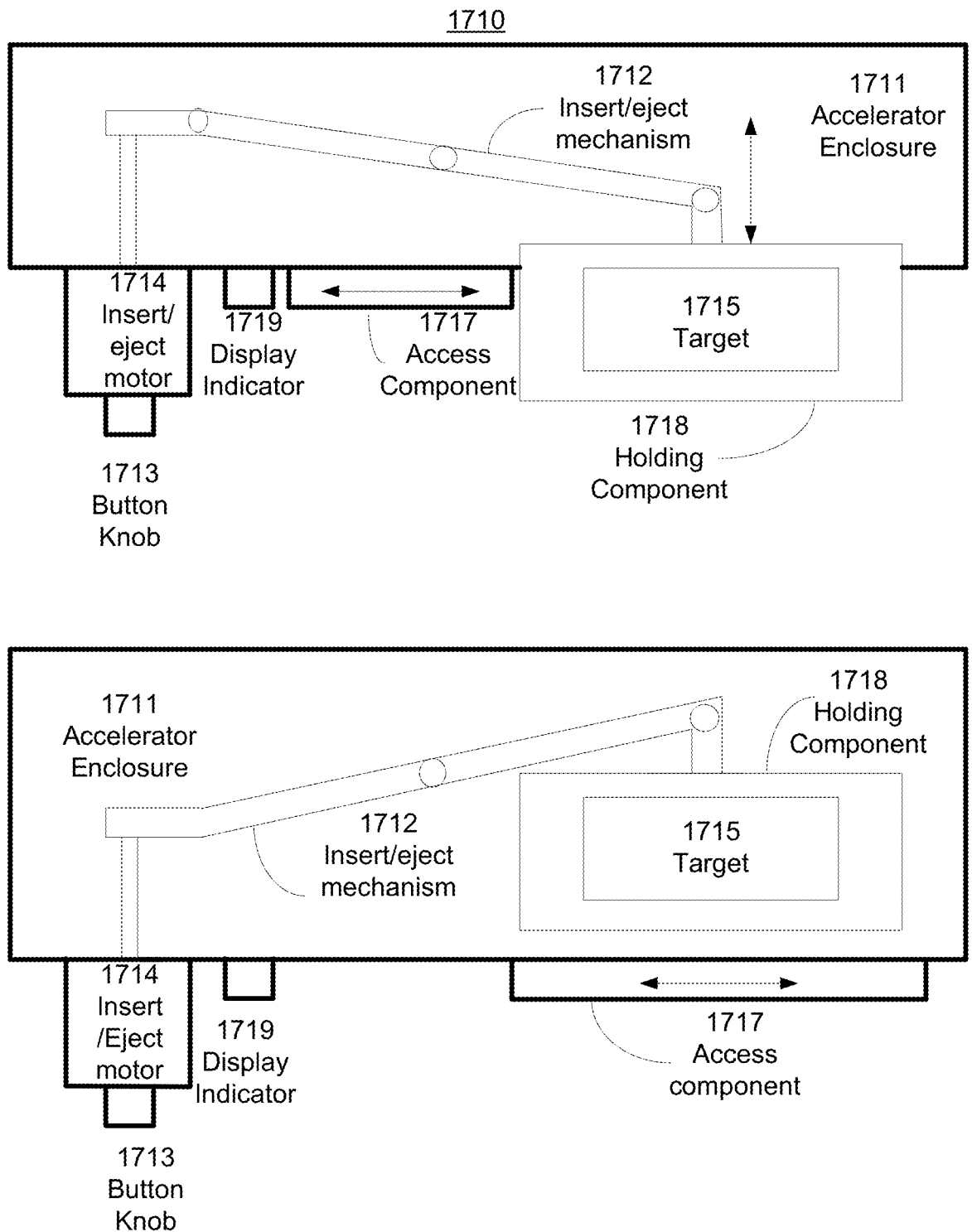
FIG. 33 is a block diagram of an exemplary loading system in accordance with an embodiment.

FIG. 33 is a block diagram of an exemplary loading system in accordance with an embodiment. The target loading system includes access component 1717, holding component 1718, inert/eject mechanism 1712, insert/eject motor 1714 with activation button 1713, and display indicator 1719. The loading system features help/assist with injecting and ejecting a high intensity target 1725. In the top illustration, access component 1717 is opened and high intensity target 1715 is put in holding component 1718. Activation button 1713 is manipulated (e.g., pushed, rotated, etc.) and insert/eject motor 1714 is activated. In one embodiment, activation button 1713 acts as a lock and a key is required to manipulate button 1713. Insert/eject motor 1714 applies forces to insert/eject mechanism 1712 which moves high intensity target 1715 into/out of an operational location within accelerator enclosure 1711. In one embodiment, insert/eject mechanism 1712 can also be a part of a target control/movement system (e.g., similar to 119, 3100, etc.) configured to change positions of high intensity target 1715 within the operational location (e.g., causing an electron beam impact location on high intensity target 1715 to change, etc.). Display indicator/alarm 1770 can convey information regarding the loading system status and operations, including indicating if there are issues (e.g., initiating an alarm, etc.).

In one embodiment, a loading system can be used to load/unload a high intensity target (e.g., 1715, 1735, etc.) into/out of an accelerator enclosure (e.g., 1711, 1731, etc.) quickly and easily (e.g., under 30 minutes, under 5 minutes, under 1 minute, etc.).

In one embodiment, a loading system includes features to avoid/prevent unintended radiation leakage. In one exemplary implementation, an access component includes features that mitigate unintended radiation leakage. In one embodiment, a various sealing configurations help prevent unintended radiation leakage.

Figure 34:
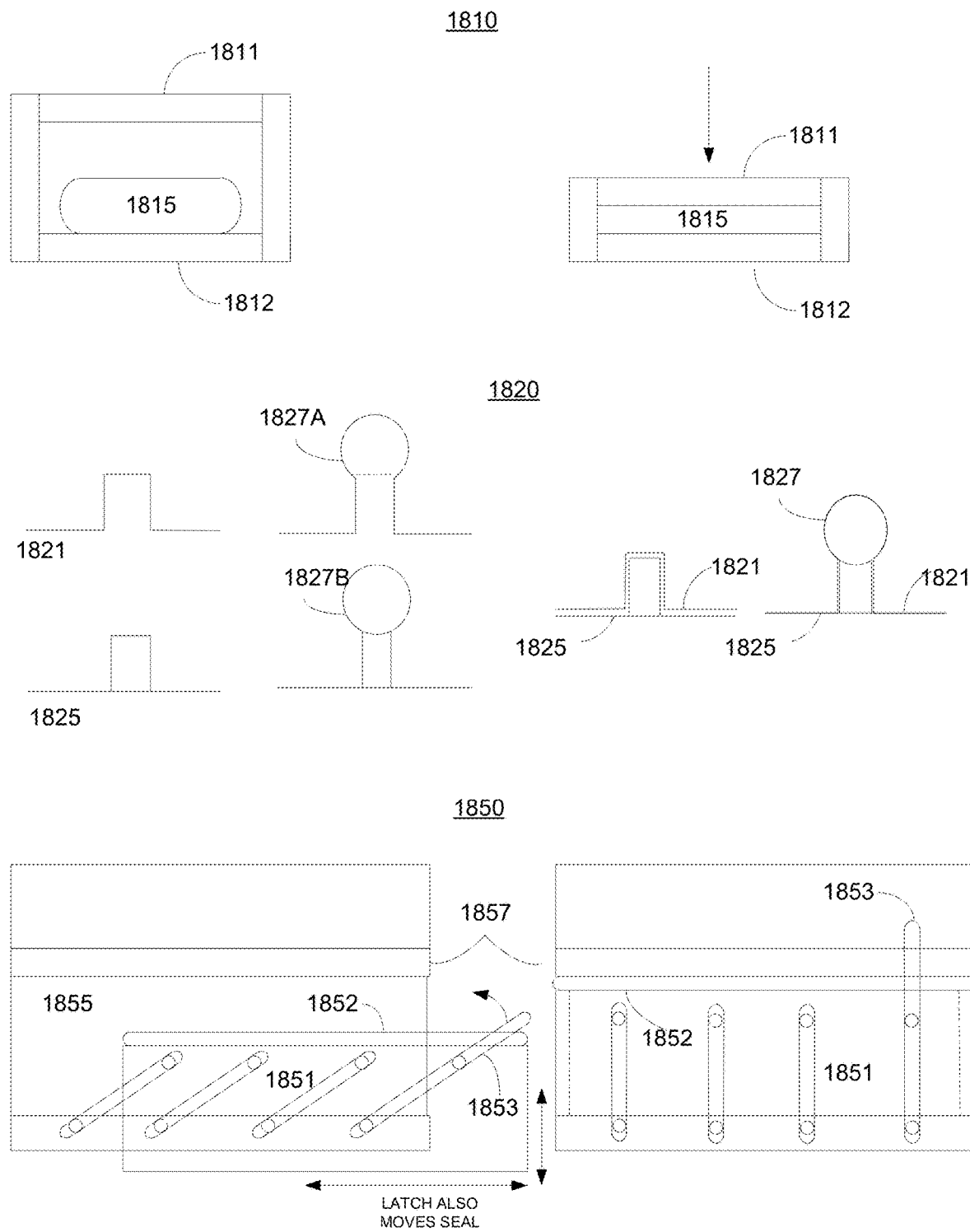
FIG. 34 is block diagram of access component sealing systems in accordance with one embodiment.

FIG. 34 is block diagram of access component sealing systems in accordance with one embodiment. Sealing system 1810 includes a seal component 1815 that gets compressed (shown in illustration on the right) by side walls 1811 and 1812. Sealing system 1820 includes a configuration in which seal component 1825 fits in (shown on illustrations on the right) seal component 1821. In one embodiment, a special configuration feature 1827 (shown as 1827A and 1727B) can be included in the seal components to enhance sealing characteristics. Sealing system 1850 can be integrated into an access component. Access component 1851 moves up and down by applying force to lever 1853 to open/close accelerator enclosure portal 1855. When in the up position, seal component 1852 engages with seal component 1857 (shown in illustration on the right). In one embodiment, the system includes a safety feature alarm that indicates if the accelerator enclosure is sealed properly.

It is appreciated that a proper position for a high intensity target can be relative to radiation activities. In one embodiment a proper position is in an operational location during radiation generation and an improper position is out an operational location (e.g., if a user forgot to insert a high intensity target, etc.). In one exemplary implementation, a proper position can be outside the operational location before and after radiation generation.

In one embodiment, a multi-access radiation camber has more than one access portal. In one exemplary implementation, there are more than one type of access portals. In one exemplary implementation, there can be multiple access components/approaches. In one embodiment, one of the access components can be considered an operational access versus a disassembling access. In one exemplary implementation, there can be multiple operational access components/portals and one disassembling access. In one embodiment, operational location access is created without separating/decoupling components that form the accelerator enclosure. In one exemplary implementation, operational location access is achieved without separating/decoupling components other than a high intensity target (e.g., there is no contiguous coupling/connection between one part of an accelerator enclosure and another part that is loose/removed to gain access as in a disassembly access).

Figure 35:
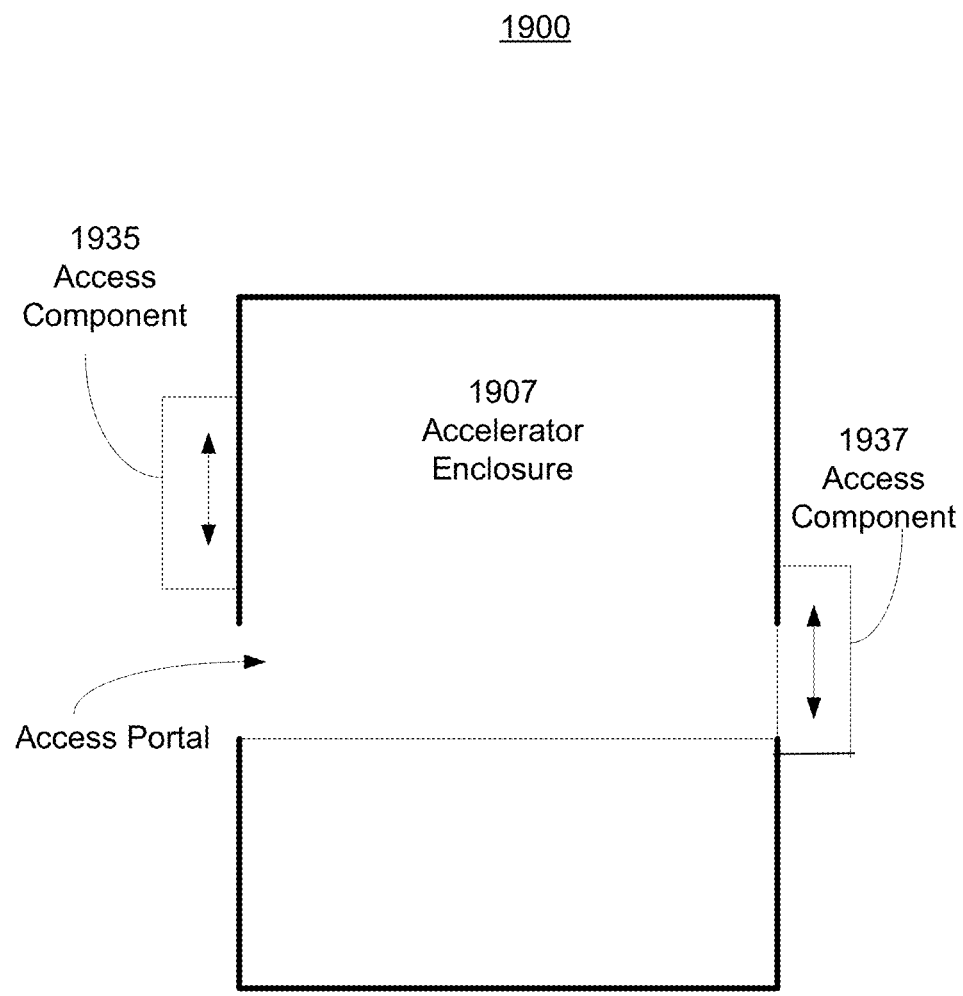
FIG. 35 is a block diagram of an exemplary multiple access radiation system in accordance with one embodiment.

FIG. 35 is a block diagram of an exemplary multiple access radiation system 1900 in accordance with one embodiment. Multiple access radiation system 1900 includes accelerator enclosure 1907, access component 1935, and access component 1937. In one embodiment, a high intensity target can be inserted when component 1935 is open and ejected when access component 1937 is open or vice versa.

Consumable High Intensity Target and Cartridge

In one embodiment, multiple high intensity targets are loaded in the radiation system at the same time. In one exemplary implementation, the multiple high intensity targets are loaded in a magazine/cartridge. The multiple high intensity targets can be loaded in the magazine/cartridge while the magazine/cartridge is coupled/attached to the radiation system. The multiple high intensity targets can be loaded in the magazine/cartridge while the magazine/cartridge is decoupled/detached from the radiation system and then the loaded magazine/cartridge is coupled to the radiation system. The multiple high intensity targets can be individually fed into an operational location. In one embodiment, the multiple high intensity targets can be individually inserted/ejected to and from an operational location.

Figure 36:
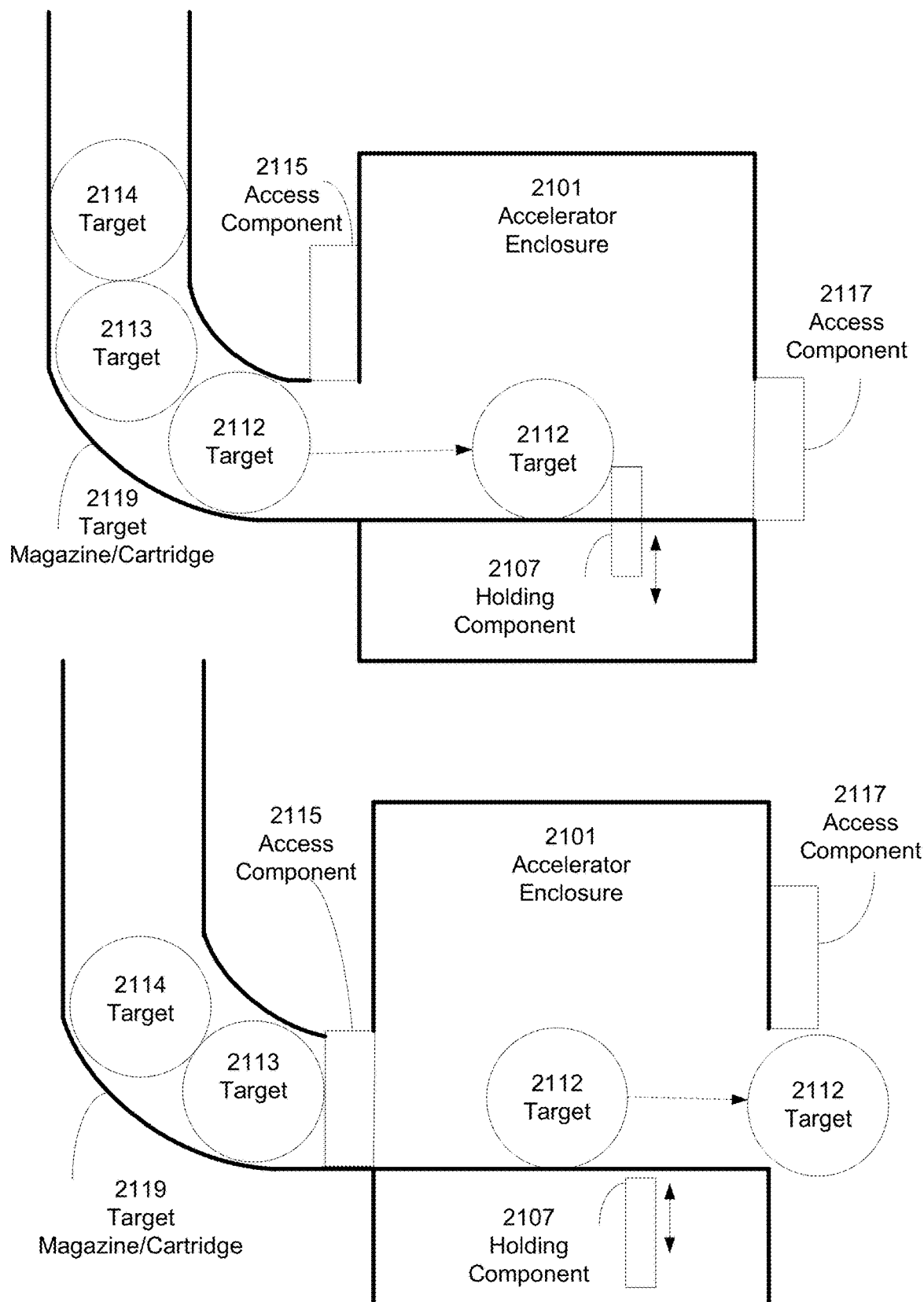
FIG. 36 is a block diagram of exemplary magazine/cartridge loading systems in accordance with an embodiment.

FIG. 36 is a block diagram of exemplary magazine/cartridge loading systems in accordance with an embodiment. The top illustration shows a magazine/cartridge loading system where the target magazine 2119 is coupled to the accelerator enclosure 2101. In one embodiment, target magazine 2119 is permanently coupled to accelerator enclosure 2101. In one embodiment, target magazine 2119 is removably coupled to accelerator enclosure 2101. Multiple high intensity targets 2112, 2113, and 2114 can be put in target magazine 2119 substantially at the same time (e.g., loaded/dropped in the magazine one after another, etc.). Then access component 2115 can be engaged/opened to allow the high intensity target 2112 to be inserted in the accelerator enclosure 2101 and held in a proper position (e.g., radiation generation) by holding component 2107. Access component 2115 can be disengaged/closed and the radiation generation begun. When the radiation generation is complete, access component 2117 is engaged/opened, holding component 2107 can be released and the high intensity target 2155 is then ejected via the portal of access component 2117.

In one embodiment, a magazine/cartridge can be replaceable in the radiation system. In one exemplary implementation, a magazine/cartridge is loaded with high intensity targets before the magazine/cartridge is coupled to the radiation system.

Figure 37:
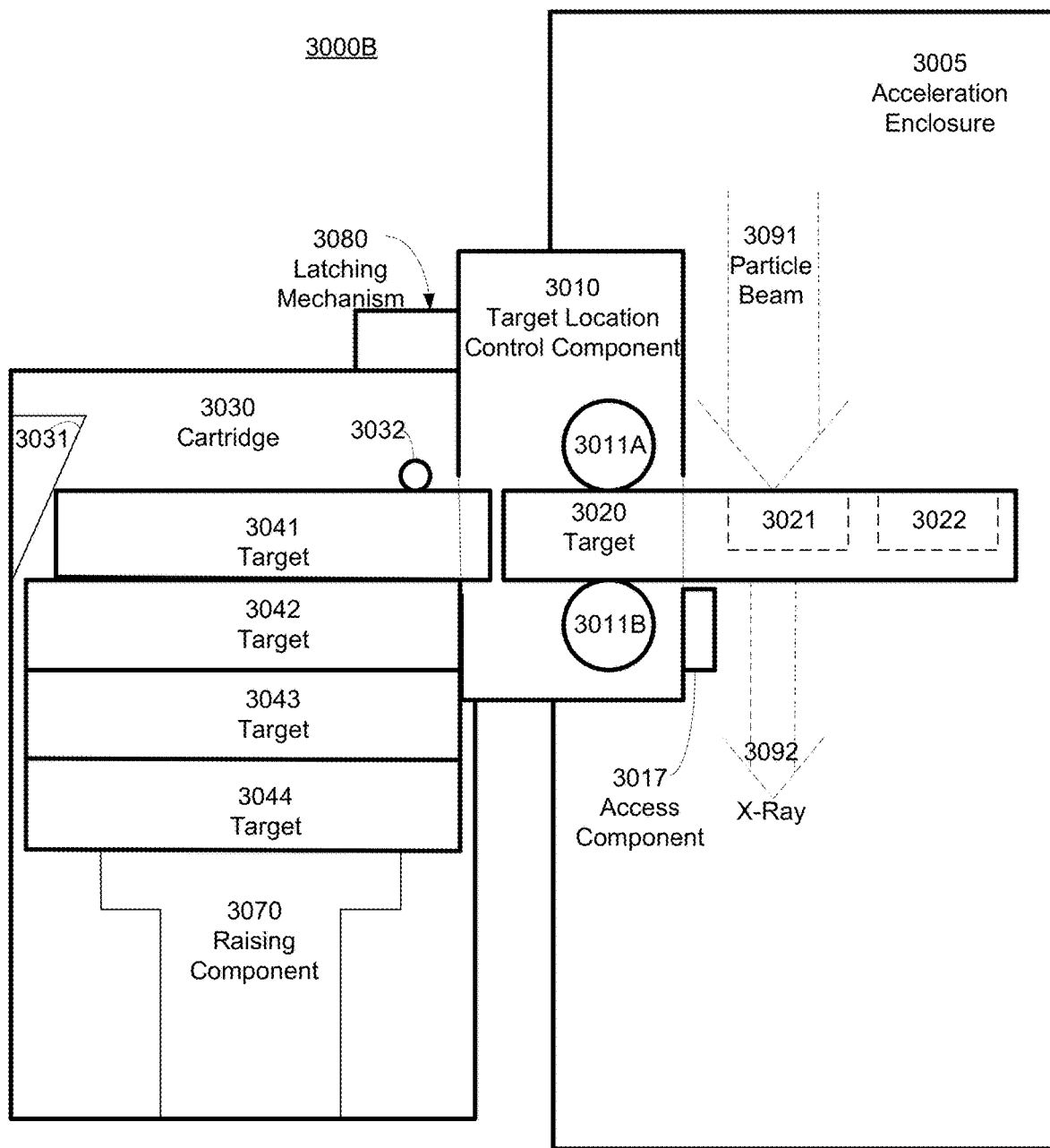
FIG. 37 is a block diagram of high intensity target system in accordance with one embodiment.

FIG. 37 is a block diagram of high intensity target system 3000B in accordance with one embodiment. High intensity target system 3000B is similar to high intensity target system 3000A in FIG. 15, except the high intensity targets are fed into the accelerator system from a target cartridge 3030. In one embodiment, target cartridge 3030 is removably couped to acceleration enclosure 3005. In one exemplary implementation, latching component 3080 is utilized to hold or release the coupling of target cartridge 3030 to/from acceleration enclosure 3005. In one embodiment, high intensity target system 3000B can include a high intensity target cartridge 3030 for storing and loading high intensity targets 3041, 3042, 3043 and 3044. In one exemplary implementation, the loading from high intensity target cartridge 3030 to target location control component 3010 is automatic. High intensity target system 3000B can include various configurations that assist the loading process. In one exemplary implementation, high intensity target cartridge 3030 includes raising component 3070 (e.g., spring, pneumatic, etc.) for forcing high intensity targets up. Structural portions of cartridge component 3030 can be configured (e.g., configuration 3031, etc.) for forcing the high intensity targets out of the cartridge component 3030 as the high intensity target is raised. High intensity target cartridge 3030 can also include a mechanism 3032 that forces the high intensity targets out. In one exemplary implementation, the cartridge utilizes a radiation shielded configuration for storing the used disposable Xray targets.

Figure 38:
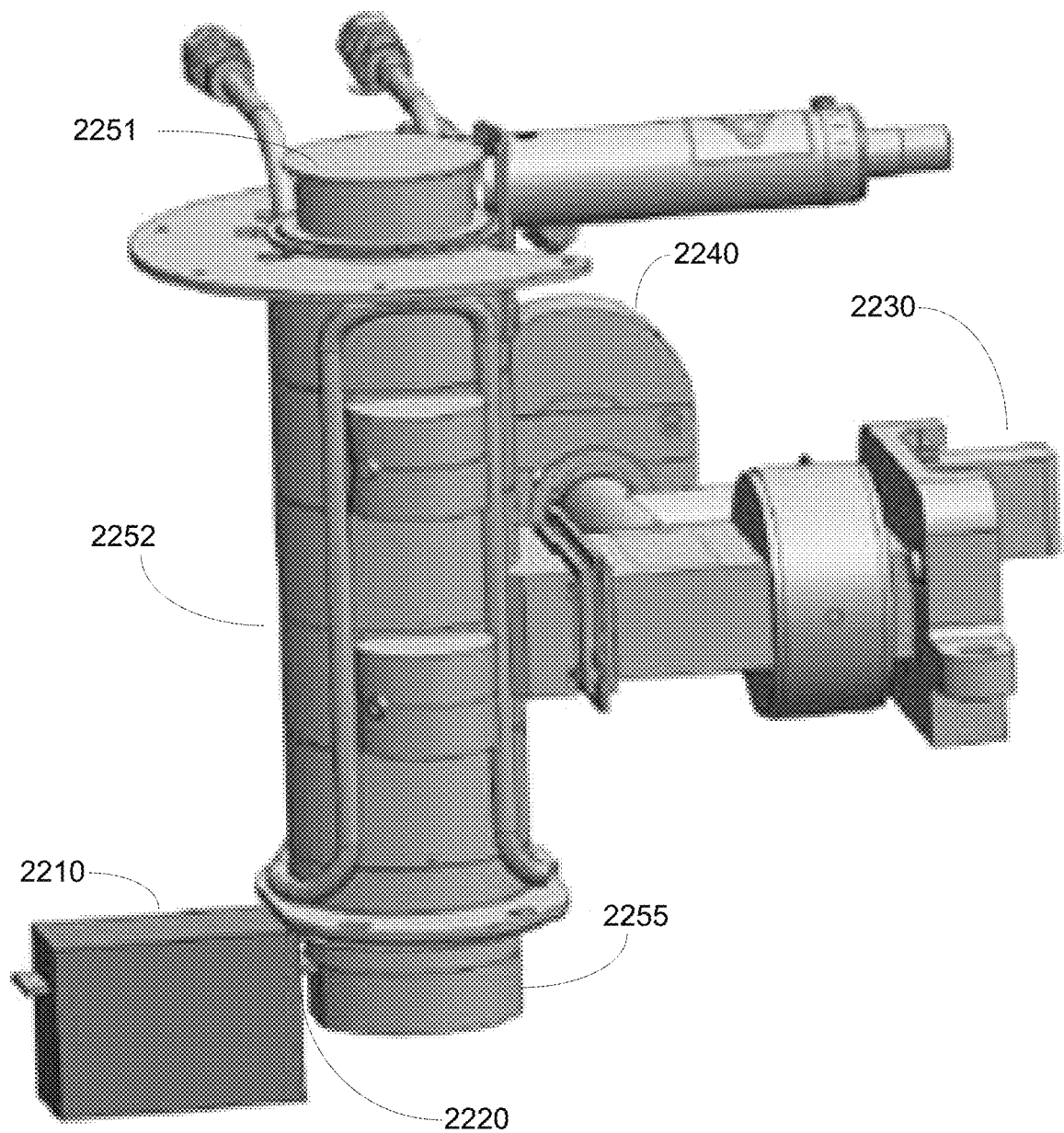
FIG. 38 is a block diagram of an exemplary accelerator system in accordance with one embodiment.

FIG. 38 is a block diagram of an exemplary accelerator system 2200 in accordance with one embodiment. In one exemplary implementation, accelerator system 2200 is similar to accelerator system 110. Access system 2200 includes target location control component 2210, high intensity target 2220, particle source 2251, acceleration portion 2252 (e.g., drift tube, etc.), collimator 2255, waveguide 2230, and high intensity target accelerator system movement component 2240. Target location control component 2210 controls adjustments/movements of high intensity target 2220. In one embodiment, target location control component 2210 can be considered a cartridge configuration including multiple high intensity targets that can be considered loaded/unloaded to the accelerator system as a group and inserted/ejected to and from an operational location individually. Particle source 2251 generates particles that are accelerated in acceleration portion 2252 and directed to impact high intensity target 2220. The impact results in radiation rays that are directed to collimator 2255, which controls the configuration of the radiation rays that leave high intensity target system 2200. Waveguide 2230 directs electromagnetic waves (e.g., radio frequency waves, microwaves, etc.) into the high intensity target system 2200. High intensity target accelerator system movement component 2240 adjusts the orientation of the high intensity target system 2200. Target location control component 2210 can direct movement of high intensity target 2220 in a linearly reciprocating motion and high intensity target 2220 can be a disposable X-ray generating high intensity target.

Figure 39:
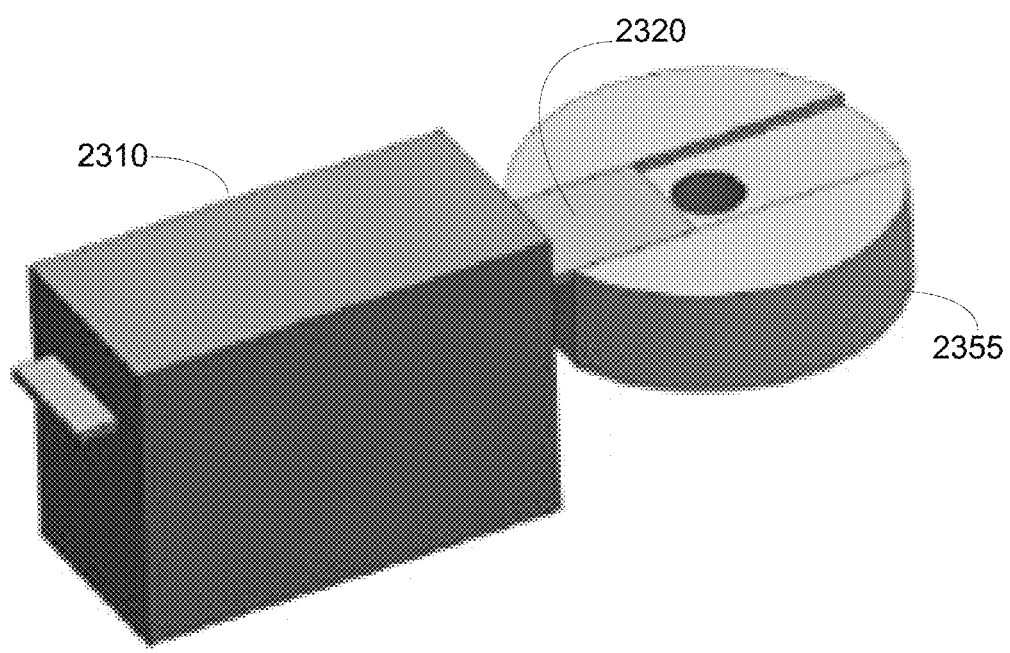
FIG. 39 is a block diagram of an exemplary high intensity target interaction with a collimator in accordance with one embodiment.

FIG. 39 is a block diagram of an exemplary high intensity target interaction with a collimator in accordance with one embodiment. Target location control component 2310 controls adjustments/movements of high intensity target 2320. Particles are directed to impact high intensity target 2320 and the impact results in radiation rays that are directed to collimator 2355. Collimator 2355 controls the configuration of the radiation rays. In one exemplary implementation, target location control component 2310, high intensity target 2320, and collimator 2355 are similar to the target location control component 2210, high intensity target 2220, and collimator 2255. Collimator 2355 can include configurations and mechanisms to help guide and support high intensity target 2320. In one embodiment, high intensity target 2320 includes a groove for the high intensity target 2320 to slide in.

FIG. 40 is a block diagram of an exemplary multiple cartridge system 2400 in accordance with one embodiment. The multiple cartridge system of 2400 includes an accelerator enclosure 2405 and multiple cartridges 2420 and 2430. Cartridge 2420 includes high intensity targets 2422 through 2424 and cartridge 2430 includes high intensity targets 2431 through 2433. High intensity targets from cartridge 2420 (e.g., high intensity target 2421, etc.) can be inserted/ejected to/from accelerator enclosure 2405 and the targets from cartridge 2430 (e.g., high intensity target 2431, etc.) can be inserted/ejected to/from accelerator enclosure 2405. In one embodiment, the high intensity targets can be sequentially inserted/ejected in the same holding component and in another embodiment sequentially injected/ejected in different holding components.

With reference still to FIG. 40, the top illustration shows one target from one of the cartridges (2420, 2430, etc.) in an operational location (e.g., within accelerator enclosure 2405, etc.). The second illustration shows a high intensity target from another one of the cartridges (e.g., 2420, 2430, etc.) in an operational location. The third illustration shows multiple targets from multiple cartridges in the in operational locations at the same time. Different configurations of high intensity targets can be added/removed to change thickness/ various configurations. The different high intensity target insertion/ejection configurations can be utilized to achieve different radiation output. The different radiation outputs can be utilized to realize/achieve different treatment (e.g., doses/, effects, results, etc.). In some embodiments, multiple different high intensity targets with different configurations enables increased controllability and performance of radiation generation over conventional target applications (that are typically limited to one single target with a static configuration).

In one embodiment, a loading system includes an ejection container for collecting the ejected high intensity targets. The container can be coupled to the accelerator enclosure. The ejection container can be releasably coupled to the accelerator enclosure. The releasably coupled container can utilize various latching mechanisms to couple the container to the accelerator enclosure. The latching mechanism can be quick attach/release mechanism. The ejection container can be similarly releasably coupled to the accelerator enclosure.

The ejection container can include a variety of safety measures. In one embodiment, the ejection container includes sealing mechanisms (e.g., prevent radiation leaks/ contamination, medical related dangers (e.g., including spread of infections, germs, virus, bacteria, etc.)

In one embodiment, the ejection container with the ejected targets is compatible with coupling to a post radiation processing system (e.g., recycling equipment, target health checking/quality control equipment, etc.). In one exemplary implementation, the ejection container is releasably coupled to the post processing equipment and used high intensity targets can be automatically fed into the post processing equipment.

With reference still to FIG. 40, the bottom illustration shows an ejection container 2470 coupled to the accelerator system instead of Cartridge 2430. High intensity targets from cartridge 2420 (e.g., replaceable high intensity target 2422, etc.) can be inserted to accelerator enclosure 2405. The replaceable high intensity targets can be ejected from accelerator enclosure 2405 into ejection container 2470 (e.g., high intensity target 2421, etc.). In one embodiment, after the used high intensity targets are fed into ejection container 2470, the ejection container 2470 can be easily decoupled from accelerator system 2405. In one exemplary implementation, after the used high intensity targets are fed into ejection container 2470 the ejection chamber 2470 can be disposed of.

The cartridge can be one of a plurality of cartridges coupled to a radiation/accelerator system. FIG. 41 is a block diagram of another exemplary multiple cartridge system 2500 in accordance with one embodiment. The multiple cartridge system of 2500 includes an accelerator enclosure 2505, a cartridge selector 2531, and multiple cartridges 2512 and 2515, and eject container 2517, all of which can be coupled/decoupled to the cartridge selector 2531. In one embodiment, the cartridge selector 2531 moves a cartridge into a position coupling with access component 2541. In one embodiment, the access component 2541 is engaged/opened and a high intensity target (e.g., 2551,2552, etc.) is inserted into the accelerator enclosure 2505.

The top illustration shows the cartridge selector 2531 moved into a position in which cartridge 2512 is coupling with access component 2541 and high intensity target 2551 inserted into an operational position (e.g., within accelerator enclosure 2505, etc.). The middle illustration shows the cartridge selector 2531 moved into a position in which cartridge 2515 is coupling with access component 2541 and high intensity target 2552 is inserted into an operational position (e.g., within accelerator enclosure 2505, etc.). The lower illustration shows the cartridge selector 2531 moved into a position in which ejection container 2517 is coupling with access component 2541 and high intensity target 2552 is ejected out of the operational position (e.g., within accelerator enclosure 2505, etc.) and into ejection container 2517.

In one embodiment, another access component can be used in addition to/instead of an assembly component to clear a jam. In one embodiment, an operational access component allows enough access room/space to reach a jammed high intensity target. In one embodiment, an additional separate jam release access component can be included and allow enough access room/space to reach a jammed high intensity target. In one embodiment, in addition to the normal operational access component an additional smaller access component can be added to allow a jam clearing tool to be used. In one embodiment, the jam clearing access component can similar to a normal operation access component allowing quick/convenient/safe access to the operational location. In one embodiment, a regular tool that has a primary function other than clearing a jam can be utilized to clear the jam. In one exemplary implementation, a screw driver with a primary function of tightening and loosing screws can be utilized to put a misaligned high intensity target back on a proper insert/ejection path.

In one embodiment, a loading/unloading system can include a jam clearing mechanism. The jam clearing mechanism can be utilized to inject/eject a high intensity target through a normal operational access when a regular injection/ejection mechanism fails. In one embodiment, the regular injection/ejection mechanism is automatic and the jam clearing mechanism is manual.

FIG. 42 is a flow chart of a high intensity target loading/ unloading method/process 2900 in accordance with one embodiment. It is appreciated that the operations of high intensity target loading/unloading process can be manual or automatic.

In block 2910, a magazine/cartridge is loaded with multiple high intensity targets. The magazine/cartridge can be loaded manually. The magazine/cartridge can be loaded automatically.

In block 2920, the cartridge, including the multiple high intensity targets, is loaded in/coupled with an is coupled to the accelerator system before the targets are loaded.

In block 2930, a cartridge selection process is performed. In one embodiment, the cartridge is included in a plurality of cartridges coupled to the accelerator system.

In block 2940, access to an operational location (e.g., within an accelerator enclosure, etc.) is obtained. In one embodiment, the access is obtained by engaging opening an access component. In one exemplary implementation the access is obtained automatically.

In bock 2950 a high intensity target is inserted in the operational location (e.g., within an accelerator enclosure, etc.). In one embodiment, the high intensity target is inserted into a holding component. The high intensity target can be inserted automatically. In one exemplary implementation, a high intensity target is inserted from a magazine/cartridge is inserted into the operational position (e.g., within an accelerator enclosure, etc.). The cartridge can be a cartridge selected in cartridge selection process (e.g., in block 1030, etc.)

In block 2960, after a radiation operation is performed access to the operational position (e.g., within an accelerator enclosure, etc.) is obtained again. In one embodiment, an access component is engaged/opened. The access component can be the same as the access component utilized in block 2940 or the access component can be a different access component.

In block 2970, the high intensity target is ejected from the operational location. The high intensity target can be ejected automatically. In one embodiment, the high intensity target is ejected into a container. The container can be a cartridge or a different type of container. The container can be the same as the cartage the high intensity target was loaded from.

In block 2980 the ejected high intensity target is removed from the radiation/accelerator system.

The high intensity target produces radiation in response to impact and collision with charged particles. In one exemplary implementation of method 2900, a particle impact location on the high intensity target is adjusted based in part upon heat generation resulting from the impact of a charged particle on the high intensity target and generation of the radiation rays. Adjustments to particle impact locations on the high intensity target assist in mitigating detrimental heat conditions.

Consumables are relatively common in the medical device industry and well accepted by customers. The target can be easily swappable, or alternatively, an automated target replacement mechanism can be implemented. Automated quality assurance tools similar to those implemented on Varian's Machine Performance Check (MPC) can be used to streamline rapid QA after target swaps. For safety, methods like radiofrequency identification or QR-based activation codes can be used to ensure that only particular vendor supplied targets are used. In one embodiment, an accelerator system includes a quality check system that checks proper performance of the replaceable high intensity target. The accelerator system can be configured to automatically monitor the condition of the replaceable high intensity target. A replaceable high intensity target can include an identification feature. The same technology can be used to track usage and ensure that targets are not used past their rated exposure limit.

A high intensity target can be configured for efficiently and effectively dissipating heat. In some embodiments, the location of heat generation from particle collisions and the transfer of heat from the location of generation can impact the configuration of the high intensity target. A high intensity target can have different configurations (e.g., material, shape, contours, etc.) based upon varying characteristics. Some portions (e.g., exterior surface, side wall, interior layer, portion in/not in the electron beam path, etc.) of a high intensity target can be selected/configured based on differing characteristics (e.g., radioactive emission characteristics, mitigating heat conductivity characteristics, radiation resistance or blocking ability to facilitate containment of radiation from undesirable emission, etc.). The differences in portion characteristics can be achieved by various approaches (e.g., different materials/substance in different portions of a high intensity target, different contours/shapes in different portions of a high intensity target, etc.). The portions or different regions of particle impact locations can produce different radiation/heat results based on the different configuration, composition, and characteristics of the respective regions/location. A high intensity target can be moved to the different regions/positions at different times to achieve different affects. The movement to the different regions can be coordinated with desired results according to a treatment plan.

Additional Temperature Control Features

Variations of the high intensity target systems and methods can include an additional way to increase the peak current that can be delivered during each individual beam pulse. One way is to increase the spot size of the electron beam. Since the target operates mainly in the transient regime, active cooling is theoretically not necessary since most of the thermal energy from the beam is absorbed by the thermal capacity of the target rather than carried away as would be necessary for a target operating in steady state. In one embodiment, elimination of water cooling on the disposable part of the target enables significant cost reduction of the consumable part.

In one embodiment, a high intensity target system and method can include active cooling features. The active cooling features (e.g., temperature control, air flow control, etc.) can be directed to assisting mitigation of heat dissipation issues. In one exemplary implementation, a high intensity target accelerator system can include air temperature/flow control mechanisms (e.g., fan, cooling compressor, etc.) that control/regulate ambient air in the area of a high intensity target. The active cooling features can be included in various parts of the high intensity target accelerator system (e.g., a high intensity target control component, cartridge component, collimator, etc.). In one exemplary implementation, a high intensity target is pre-cooled before particle collisions occur (e.g., pre-cooled in a cartridge, etc.).

Multiple Accelerator Systems and Methods

It is appreciated that the presented high intensity target systems enable implementation of efficient and effective radiation systems. One characteristic of the presented high intensity target systems is they are generally less expensive and more cost effective than conventional systems. This in turn enables presented high intensity target systems to overcome the practical limitations of traditional approaches. Given the efficiency and effectiveness of high intensity target systems and overcoming conventional system limitations, it becomes practical to utilize multiple accelerator systems to further assist in overcoming dose limitations of traditional approaches. In one exemplary implementation, combining multiple accelerator systems and applying substantially Simultaneous radiation from multiple approaches/angles enables combined greater dose rates.

In one embodiment, an average dose rate is greater than or equal to 1.0 Gy/s at one meter SAD and peak dose rates greater than or equal to 0.002 Gray per pulse (Gy/pulse). In one exemplary implementation, a high energy machine can achieve a dose rate of 4,000 MU/min at 10 MeV. The peak target current, pulse repetition rate and average beam power onto the target are 55 mA, 360 pps and 1 kW, respectively. In one exemplary implementation, a high intensity target can sustain twice the peak current, and if the target moves between pulses, the pulse repetition rate can be increased fivefold to 1,800 pps. In addition, a reduction of the source-axis-distance (SAD) from 1 m to 80 cm, can lead to twice the dose rate due to the $1/r^2$ dependency of dose rate on SAD. The combined effect of these improvements is that an accelerator system can deliver almost 14 Gy/s. Therefore, combining three or more accelerator systems enables combined dose rates above the 40 Gy/s that is generally associated with a FLASH regime. In one embodiment, an individual accelerator contributes Bremsstrahlung radiation corresponding to average dose rates greater than or equal to 2.0 greys per second (Gy/s) at isocenter to a total dose rate of Bremsstrahlung radiation from a plurality of accelerators, wherein total dose rate amount of Bremsstrahlung radiation corresponds to average dose rates greater than or equal to 40.0 greys per second (Gy/s) at isocenter.

Figure 43:
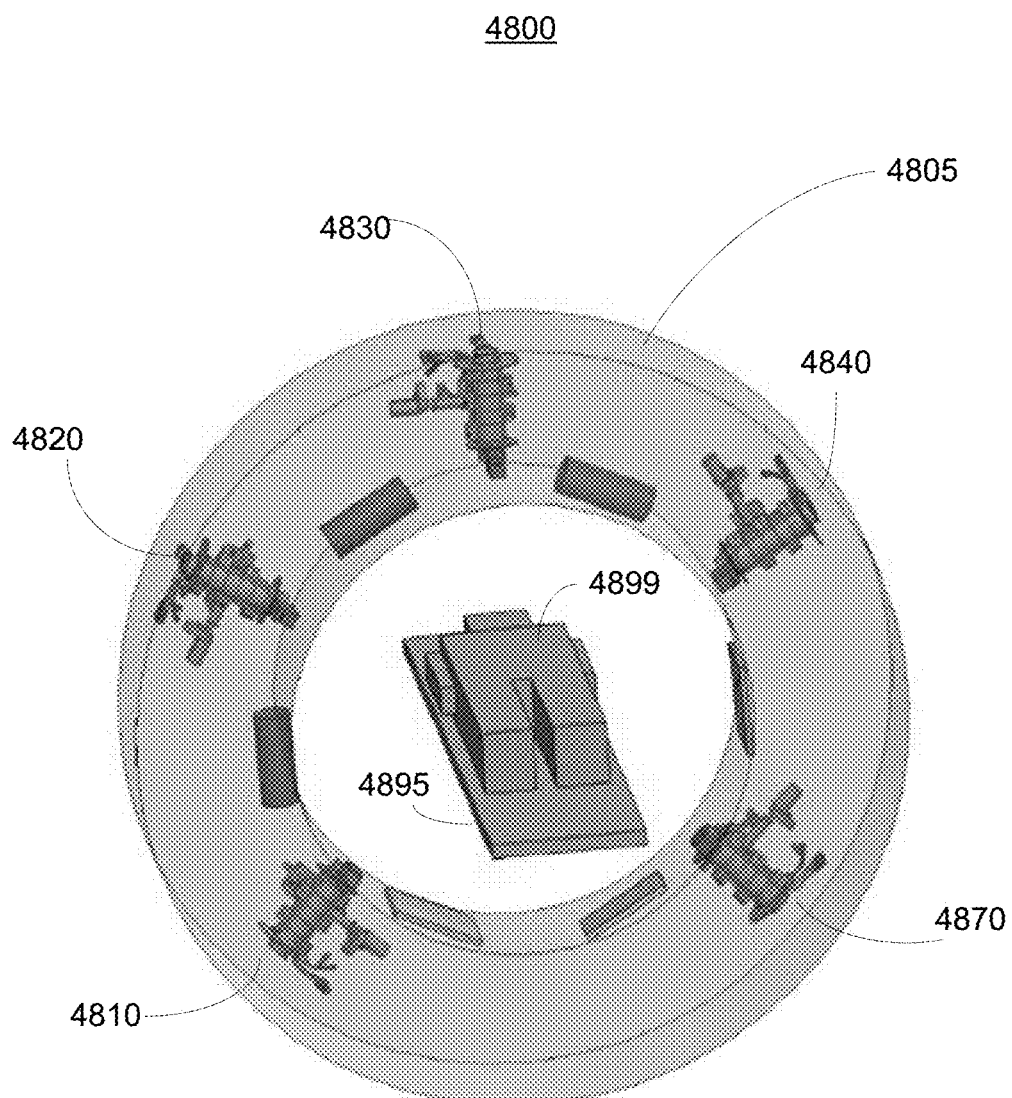
FIG. 43 shows an example of five accelerator systems in accordance with one embodiment.

Thus, to further achieve better dosimetry, additional accelerator systems can be added. FIG. 43 shows an example of five accelerator systems in accordance with one embodiment. Multiple accelerator configuration 4800 includes accelerator systems 4810, 4820, 4830, 4840, and 4870, support component 4895, and patient with target tissue 4899. In one exemplary implementation, accelerator systems 4810, 4820, 4830, 4840, and 4870 are similar to accelerator system 110 and support component 105 is similar to support component 4895. The accelerator systems 4810, 4820, 4830, 4840, and 4870 can be mounted 72 degrees apart in a circular plane (e.g., on a gantry 4805, etc.). In one exemplary implementation, better dose profiles are expected if an odd number of accelerator systems are used, as no two accelerators would be colinear to retrace the same path through healthy tissue. The accelerator systems and associated RF chains can include 10 MV energy S-Band with small bend magnets. In one embodiment, an accelerator system can deliver 18 GY in 270 ms. The use of multiple accelerator systems enables use of collimators with characteristics (e.g., speed, etc.) that can facilitate cost reductions compared to traditional approaches.

Figure 44:
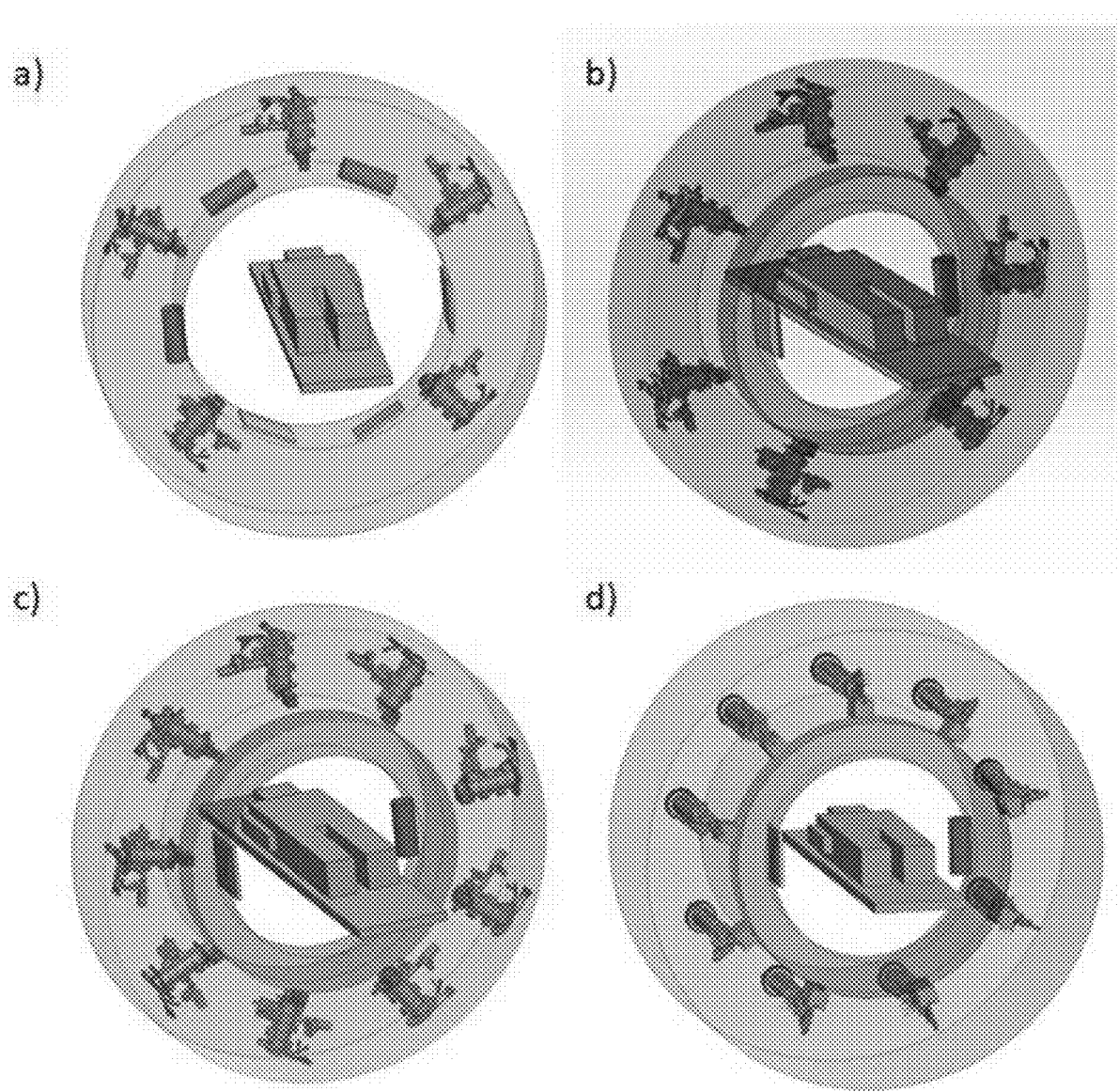
FIG. 44(A) illustrates an exemplary configuration with five accelerator systems and 3 integrated kV imaging systems in accordance with one embodiment.
FIG. 44(B) shows an exemplary configuration with seven accelerator systems, in which the kV imaging system is moved onto a separate ring to make space for additional accelerator systems.
FIG. 44(C) shows an example of nine accelerator systems in a first orientation in accordance with one embodiment.
FIG. 44(D) shows an example of nine accelerator systems in a second orientation in accordance with one embodiment.

A system can include diagnostic imaging systems. FIG. 44(A) illustrates an exemplary configuration with five accelerator systems and 3 integrated kV imaging systems in accordance with one embodiment. FIG. 44A also demonstrates one potential way to balance the described modifications in energy per pulse, repetition rate, SAD and number of accelerator systems. For example, the energy per pulse can be increased by a factor of three or the SAD can be reduced more aggressively. Being more aggressive at one step can further increase dose rate or enable treatment to be less aggressive at other steps. For example, the pulse repetition rate can be reduced to 1,000 pps by using 9 accelerator systems instead of 5.

The gantry can be stationery and couch kicks can be used to find a setup that minimizes conflict with critical organs. Alternately (or additionally), the gantry can rotate (e.g., by +/−36 degrees, etc.) to provide true 360 coverage since the configuration is angularly symmetric (e.g., at 72 degrees, etc.). In one embodiment, an optimal angle for the treatment delivery can then be chosen. Furthermore, in one embodiment the full allowed rotation (e.g., starting at −36 degrees and going to +36 degrees, etc.) enables a cone beam CT (e.g., 220 degree cone beam, etc.), if the images from the kV systems (e.g., three kV systems, etc.) are combined. The gantry can also traverse a rotational range (e.g., the full range between accelerator systems, 72 degrees, etc.) rapidly (e.g., on the order of a second. etc.) making arc therapy possible (e.g., FLASH-Arc Therapy, FLASH-VMAT, etc.). The different orientations (e.g., gantry rotation, robotic arm rotation, etc.) can provide flexibility for different radiation entrance angles in a tissue target.

FIG. 44(B) shows an exemplary configuration with seven accelerator systems, in which the kV imaging system is moved onto a separate ring to make space for additional accelerator systems. The imaging ring can be much lighter than the treatment gantry and therefore rotate independently through a full or half rotation, eliminating the need for duplicate kV imaging systems. The couch can translate axially to move the tissue target (e.g., tumor, etc.) from the imaging plane to the treatment plane or a mechanism can be implemented that moves the imaging components axially in and out of the treatment plane. In one exemplary implementation, a configuration with seven accelerator systems can include one kV imaging system on a separate gantry.

FIG. 44(C) shows an example of nine accelerator systems in a first orientation in accordance with one embodiment. In addition to allowing for lower pulse repetition rates, a larger number of accelerator systems can also allow for better treatment plans. A larger number of accelerator systems can be particularly helpful if the treatment gantry is stationary. Eliminating the need to rotate the treatment gantry can enable reductions in cost and complexity.

FIG. 44(D) shows an example of nine accelerator systems in a second orientation in accordance with one embodiment. In one embodiment, multiple accelerator systems can be included in a gantry system. The gantry can be stationery and couch kicks can be used to position a patient. FIG. 44(D) shows a configuration where the 10 MeV accelerator systems are arranged horizontally and use a bend magnet with energy slit. Horizontal placement allows for a longer accelerator system, which can reduce costs of the RF system. The bend magnet with energy slit can produce cleaner energy spectra and reduce thermal load on the x-ray target by scraping the low energy tail. In one exemplary implementation, FIG. 44D illustrates a configuration with nine accelerator systems that also use bend magnets.

Figure 45:
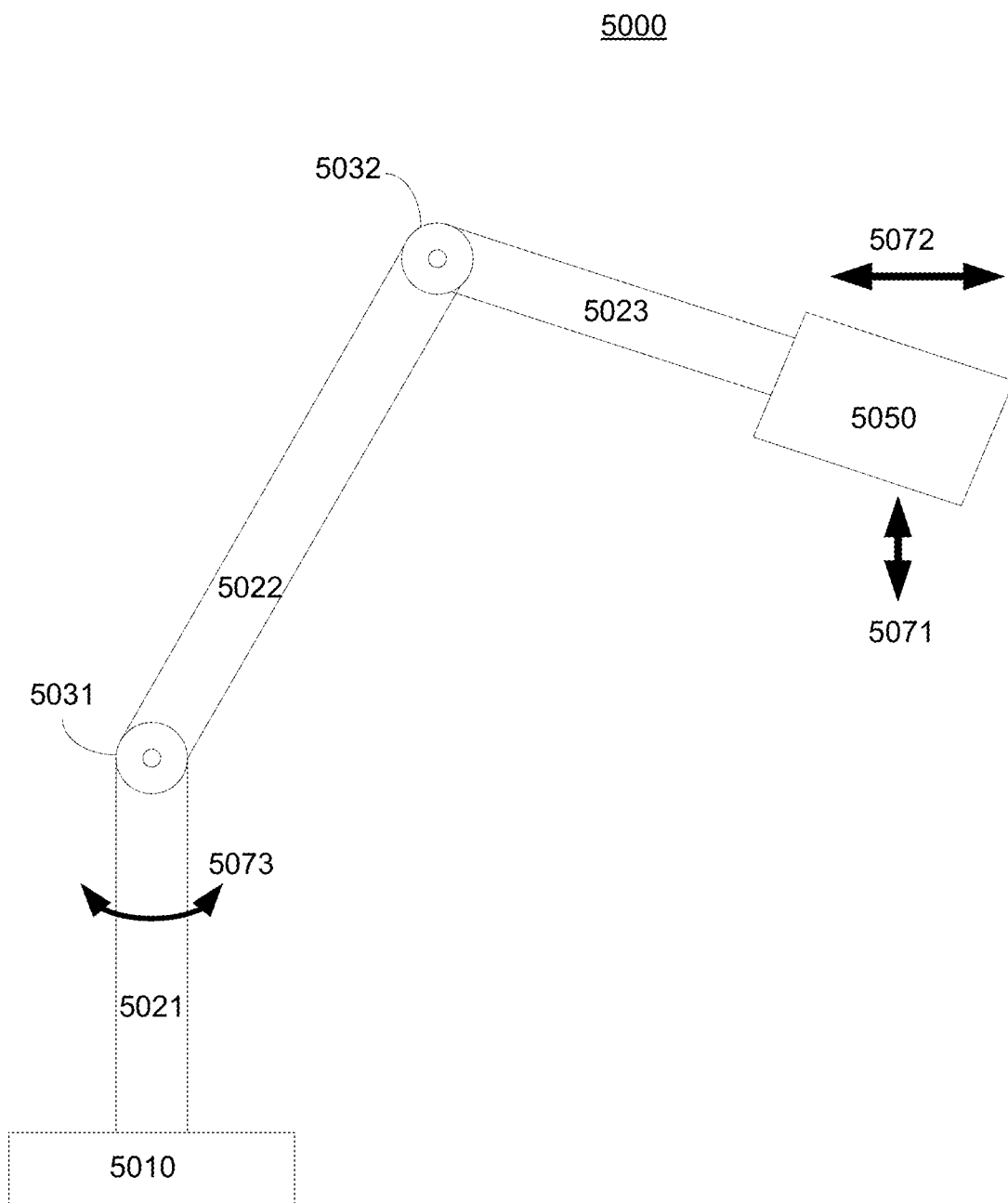
FIG. 45 is a block diagram of a high intensity target accelerator robotic arm system in accordance with one embodiment.

It is appreciated that the presented high intensity target accelerator systems and methods are compatible with various configurations. High intensity target accelerator systems and methods can be implemented with various mounting configurations (e.g., gantry, robotic arm, etc.). FIG. 45 is a block diagram of a high intensity target accelerator robotic arm system 5000 in accordance with one embodiment. In one exemplary implementation, robotic arm system 5000 is a multi-beam photon flash treatment system using robotic arms for moving accelerator systems. High intensity target accelerator robotic arm system 5000 includes a base 5010, a first arm segment 5021, second arm segment 5022, a third arm segment 5023, a first arm joint 5031, a second arm joint 5032, and accelerator system 5050. Joints 5031 and 5032 enable arms 5022, 5022, and 5013 to move in various directions. In one exemplary implementation, the high intensity target accelerator robotic arm system 5000 allows for greater flexibility in positioning and delivering the beams. The high intensity target accelerator robotic arm system 5000 can enable the accelerator system 5050 to move in an vertical motion (e.g., 5071), horizontal motion (e.g., 5072), and a rotating motion (e.g., 5073).

Figure 46:
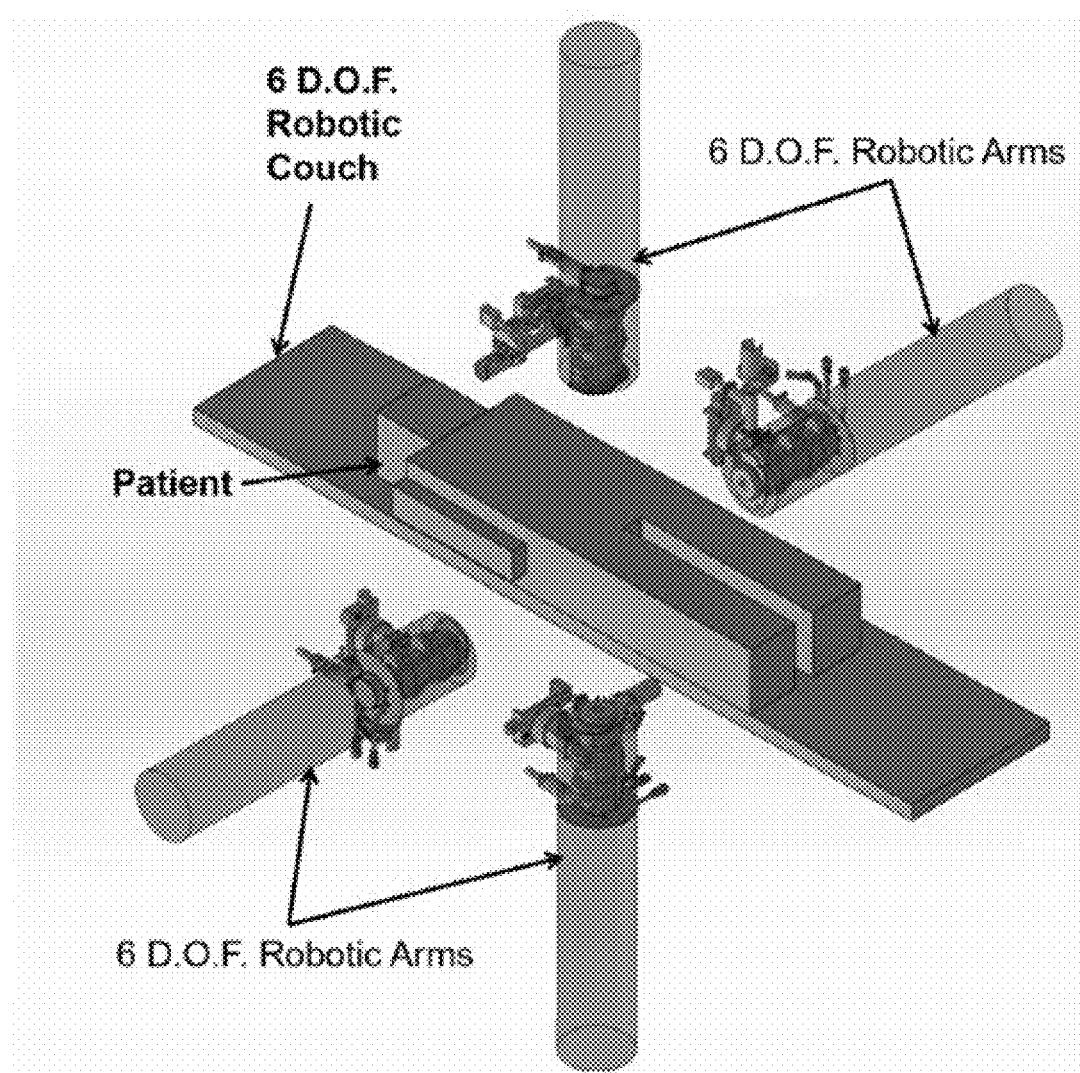
FIG. 46 is a block diagram of an example implementation with multiple accelerator systems mounted on multiple robotic arms in accordance with one embodiment.

In one embodiment, multiple robotic arms and corresponding accelerator systems can be utilized. FIG. 46 is a block diagram of an example implementation with multiple accelerator systems mounted on multiple robotic arms in accordance with one embodiment. In one exemplary implementation, the patient is resting on a 6 degree of freedom (D.O.F.) robotic couch and the accelerator systems are included in a 6 independent D.O.F. robotic arm. It is appreciated various adjustments can be made in the robotic arms (e.g., independent motions, coordinated motions, etc.). In one embodiment, the accelerator systems include high intensity targets. Mounting each accelerator on a robot arm can allow for greater flexibility in positioning and delivering the beams.

It is appreciated that high intensity target systems and methods can be compatible with a variety of radiation treatment approaches. A high intensity target can be utilized for high dose rate treatments. In one embodiment, a high intensity target is used to deliver radiation therapy capable of relatively high dose rates that are delivered during time intervals of frozen movement or no movement in a treatment target. In one exemplary implementation, a radiation treatment dose rate is compatible with delivery of radiation to a treatment target in a chest area in a time interval corresponding to no movement in the chest area due to inhaling or exhaling a breath (e.g., no movement due to a lung expanding, contracting, etc.).

Some treatment or therapy approaches include ultra-high dose rate treatment or modality referred to as FLASH radiotherapy. Therapeutic windows associated with FLASH therapy often enable reduced normal tissue toxicity while maintaining cancerous tissue tumor control. In one embodiment, a high intensity target is used to deliver FLASH radiation therapy. In one exemplary implementation, the FLASH radiotherapy dose rate can be at least 40 Gray per second (Gy/s). The radiation therapy systems and methods can also be compatible with multiple field treatment approaches in which different fields are associated with a particular treatment trajectory and a dose per field that is a portion or fraction of a total dose delivery. In one embodiment, getting above 1 Gy/s requires a radiation system capable of operating at greater than 1 MeV.

Figure 47:
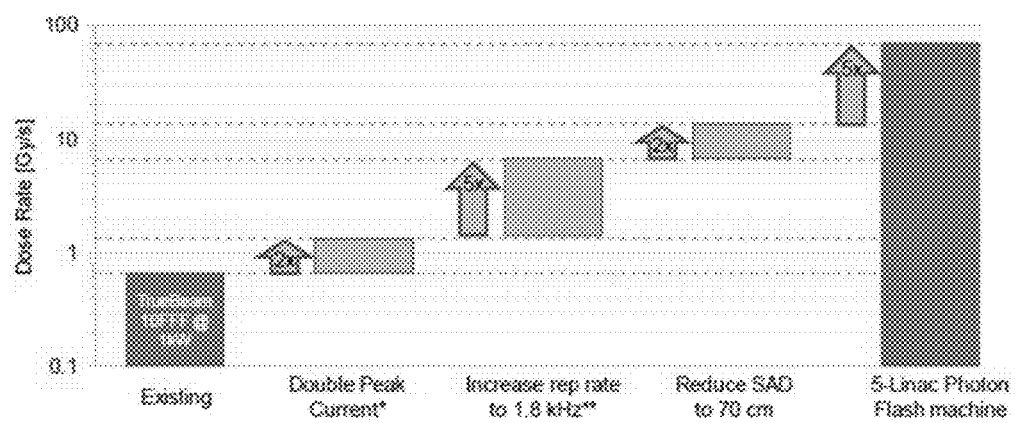
FIG. 47 is a graphical representation of some exemplary various aspects (e.g., configurations, functionalities, operations, conditions, features, characteristics, etc.) that are significantly different in the new high intensity target systems and methods.

FIG. 47 is a graphical representation of some exemplary various aspects (e.g., configurations, functionalities, operations, conditions, features, characteristics, etc.) that are significantly different in the new high intensity target systems and methods. The differences can enable high intensity target systems and methods to supply high dose rates (e.g., greater than 40 Gy/s, FLASH, etc.) The different aspects can include:
1) a replaceable/disposable target (e.g., a 2× dose rate increase, etc.);
2) a movable target—change in electron impact location (e.g., a 5× dose rate increase, etc.):
3) change SAD (e.g., a 2× dose rate increase, etc.): and
4) multiple simultaneous accelerators (e.g., a 5× dose rate increase, etc.).

The dose rates indicate exemplary high intensity target system and method dose rate increases with respect to traditional approaches (e.g., doubling, 5 times, etc.). It is appreciated that different combinations (e.g., with different modifiers, etc.) can be implemented. FIG. 47 is a graphical representation illustrating progression to achieving increases in dose rates. The dose rates are shown for existing true beam 10FFF@1KW, increases due to doubling peak current, improvements due to increasing the rep rate to 1.8 kHz, improvements due to recuing SAD to less than or equal to 80 cm, and an increase associated with using 5 high intensity target accelerator systems. In one exemplary implementation, a high intensity target accelerator system achieves a dose rate of 70 Gy/s. associated with FLASH therapy dose rates using multiple 10 MeV high intensity target accelerator systems in a multi-angle system.

In one embodiment, a radiation system can include a replaceable/disposable high intensity target. In one embodiment, a radiation system can include a movable high intensity target. A radiation system can include both high intensity a target that is both replaceable/disposable and moveable. In one embodiment, a high intensity target is replaceable/disposable first and movable second. In one embodiment, a high intensity target is moveable first and replaceable/disposable second.

In one embodiment, accelerator systems can be independently powered by their own RF chain. Each accelerator system can include its own high intensity target, ion chamber and collimator. Some of the components can be readily adapted for use with off-the shelf components.

Figure 48:
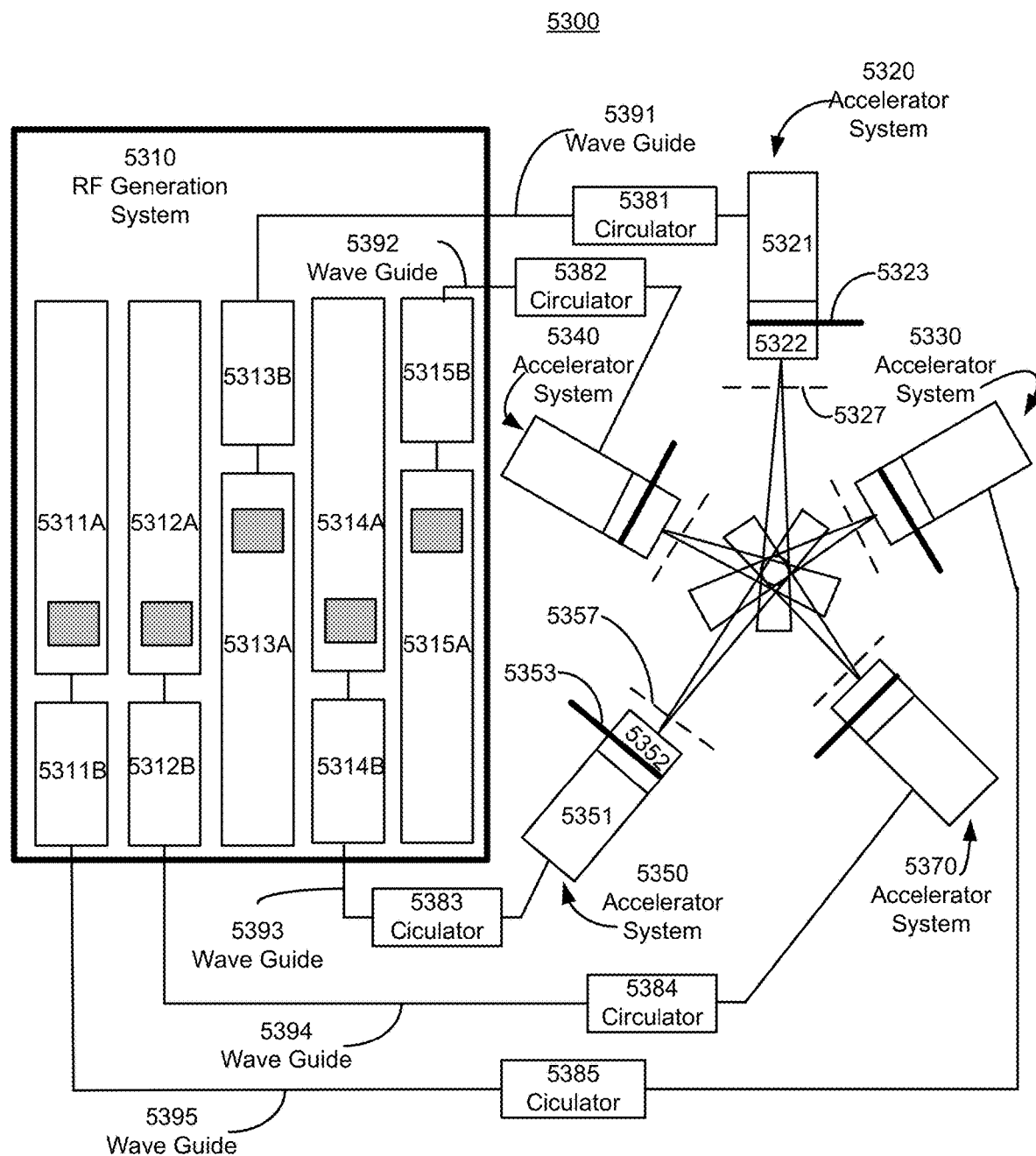
FIG. 48 is a block diagram of an exemplary radiation system with multiple accelerators in accordance with one embodiment.

FIG. 48 is a block diagram of an exemplary radiation system 5300 with multiple accelerators in accordance with one embodiment. The radiation system 5300 can be configured with separate independent RF chains fed from a bank of RF generators. The RF source and modulator can be included in a bank configuration. In one embodiment, a RF generation system bank can be utilized to supply RF signals via the RF chains. In one exemplary implementation, accelerator systems can be operated (e.g., powered, tuned, servo-controlled, intensity modulated, etc.) independently by their own RF chain. In one embodiment, independent operation of the accelerators enables different treatment results from different accelerators (e.g., different doses, different dose rates, different types of radiation, etc.).

In one embodiment, the independent operation of the accelerators can be coordinated. In one exemplary implementation, the coordination can be directed to achieving a treatment plan. In one exemplary implementation, a first accelerator provides a first portion of a treatment plan radiation and a second accelerator provides a second portion of a treatment plan radiation, and the first and second portion are coordinated so that together they satisfy the overall treatment plan radiation.

In one embodiment, an accelerator system (e.g., similar to accelerator systems 110, 1300, etc.) can receive microwave signals from a RF chain. In one embodiment, a RF chain includes a RF source and a modulator. A RF chain can also include a waveguide, a rotary joint, a circulator, coupled AFC and servos, and so on. FIG. 48 is a block diagram of an exemplary radiation system 5300 with multiple accelerator systems in accordance with one embodiment. Radiation system 5300 includes a microwave generation system 5310 and accelerator systems 5320, 5330, 5340, 5350, and 5370. In one embodiment microwave generation system 5310 is organized in a bank configuration comprising modulators 5311A, 5312A, 5313A, 5314A, and 5315A coupled to klystrons 5311B, 5312B, 5313B, 5314B, and 5315B, respectively.

The accelerator systems 5320, 5330, 5340, 5350, and 5370 can receive microwave power from microwave generation system 5310 via RF chains. Accelerator systems 5320 receives microwave signals via a RF chain comprising modulator 5313A, klystron 5313B, waveguide 5391, circulator 5381, and so on. Accelerator systems 5340 receives microwave signals via a RF chain comprising modulator 5315A, klystron 5315B, waveguide 5392, circulator 5382, and so on. Accelerator systems 5350 receives microwave signals via a RF chain comprising modulator 5314A, klystron 5314B, waveguide 5393, circulator 5381, and so on. Accelerator systems 5370 receives microwave signals via a RF chain comprising modulator 5312A, klystron 5312B, waveguide 5394, circulator 5384, and so on. Accelerator systems 5330 receives microwave signals via a RF chain comprising modulator 5311A, klystron 5311B, waveguide 5395, circulator 5385, and so on. Similar to respective RF chains having respective multi-port circulators (e.g., 5381, 5382, 5383, 5384 5385, etc.) RF chains can have respective rotary joints, couplers, automatic frequency/fine control (AFC), servos, and so on.

In one embodiment, accelerator systems (e.g., 5320, 5330, 5340, 5350, 5370, etc.) can be similar to accelerator systems 110, 1510 and so on. In one embodiment, an accelerator system (e.g., 5320, 5350, etc.) can include a linear accelerator (e.g., 5321, 5351, etc.), a high intensity target (e.g., 5323, 5353, etc.), and a primary collimator (e.g., 5322, 5352, etc.). The accelerator systems can include flattening free filter linear accelerators. In one exemplary implementation, an accelerator system (e.g., 5320, 5350, etc.) can include a secondary collimator (e.g., 5327, 5357, etc.). The secondary collimator can be a low resolution slow multi-leaf-collimator (MLC).

In one embodiment, adding an MLC to every beam line can be costly, however high intensity target systems and methods can enable opportunities for cost reduction to be implemented and leveraged. Since a FLASH system is primarily a radiosurgery system, the MLC can be smaller, or a cone-based collimation system can be used. The MLC can be further cost-reduced by accepting slow leaf speeds and only moving the leaves during setup, but not during treatment. Larger (and therefore fewer) leaves can be implemented.

It is appreciated that some of the components of a high intensity target system can be readily altered/changed for use with off-the shelf components. While some components can be implemented by altering/changing off the self components, other components (e.g., high intensity targets, high rep rate RF system bank, "fast" gantry, etc.) are not readily available by altering/changing off the self components.

The bank of RF generators can include multiple RF generation vacuum tubes. While some types of RF generation vacuum tubes (e.g., klystron, magnetron, etc.) may be better suited to different applications (e.g., traditional radiation treatment, FLASH radiation treatment, etc.), it is appreciated that presented RF generation systems/schemes are compatible with different types of RF generation. In one embodiment, a long-lasting high average power klystron can be operated at an increased pulse repetition frequency (PRF). In one exemplary implementation, the long-lasting high average power klystron can be operated at an increased PRF at the expense of pulse length. While a Klystron may have limitations on time averaged heat flux and pulsed heating of the collector (e.g., energy per pulse, etc.), trading pulse length for PRF results in similar peak power output and collector pulse heating. The table 2 below includes characteristics of different Klystrons (e.g., types A, B and C) in accordance with one embodiment.

TABLE 2

| Klystron Type | Operating Frequency (GHz) | Peak RF Power (MW) | Average RF Power (kW) | RF Pulse Length (uS) | Average Beam Power |
|---|---|---|---|---|---|
| A | 2.9985 | 5 | 16.3 | 880 | 167 |
| B | 2.856 | 5.5 | 25 | 600 | 178 |
| C | 2.856 | 5 | 18 | 667 | 163 |

In one embodiment, a modulator is capable of handling a high average power (e.g., 50-80 kW, etc.) per vacuum tube RF generator. The selection of the modulator and average power can depend upon an accelerator guide length, PRF, peak RF power chosen, and so on. In one exemplary implementation, a modulator can operate at 500 HZ and include insulated gate bipolar transistor (IGBT) switches (e.g., that operate at 4-5 kHz, etc.). In one exemplary implementation, a modulator can include IGBT switches and operate at pulse frequencies between 500 Hz and 5 KHz. The modulator or modulator bank can operate with a RF peak power of 20-50 Mw, pulse voltage of 250-360 kV, pulse current of 200-350 A, a modulator peak of 115 MW, and a modulator average of 80 kW. In one embodiment, a PRF is extended (e.g., from 1 kHz to 1.8 kHz, etc.). In one embodiment, the independent delivered photon beam lines can have large overlaps (e.g., radiation beams from different accelerators can overlap/intersect in a tissue target volume, etc.). Radiation generation by multiple accelerators can be coordinated to provide various radiation therapy and treatment effects.

While the results may be similar, it is appreciated the presented multiple accelerator system implementations (e.g., with respective high intensity targets, etc.) can be more efficient and effective than conventional approaches. It is also appreciated that multiple accelerator system implementations (e.g., similar to system 500, 2000, etc.) can be flexibly configured. In one embodiment, multiple patient stations with separate patient supports and corresponding accelerator systems can be serviced by a single microwave generation system bank.

In one embodiment, a radiation station includes multiple accelerators (e.g., on a gantry, etc.) loaded with different high intensity targets. The high intensity targets can be different types (e.g., different configurations, materials, shapes, etc.). The high intensity targets can be associated with different treatment doses/effects. In one exemplary implementation, one of the accelerators is loaded with a first type of target (e.g., tungsten, etc.) and another accelerator loaded with a second type of target (e.g., copper, etc.) and different treatment doses/effects can be achieved by using a combination of radiation from different types of targets (either simultaneously or sequentially, etc.) but having an advantage over prior art.

Figure 49:
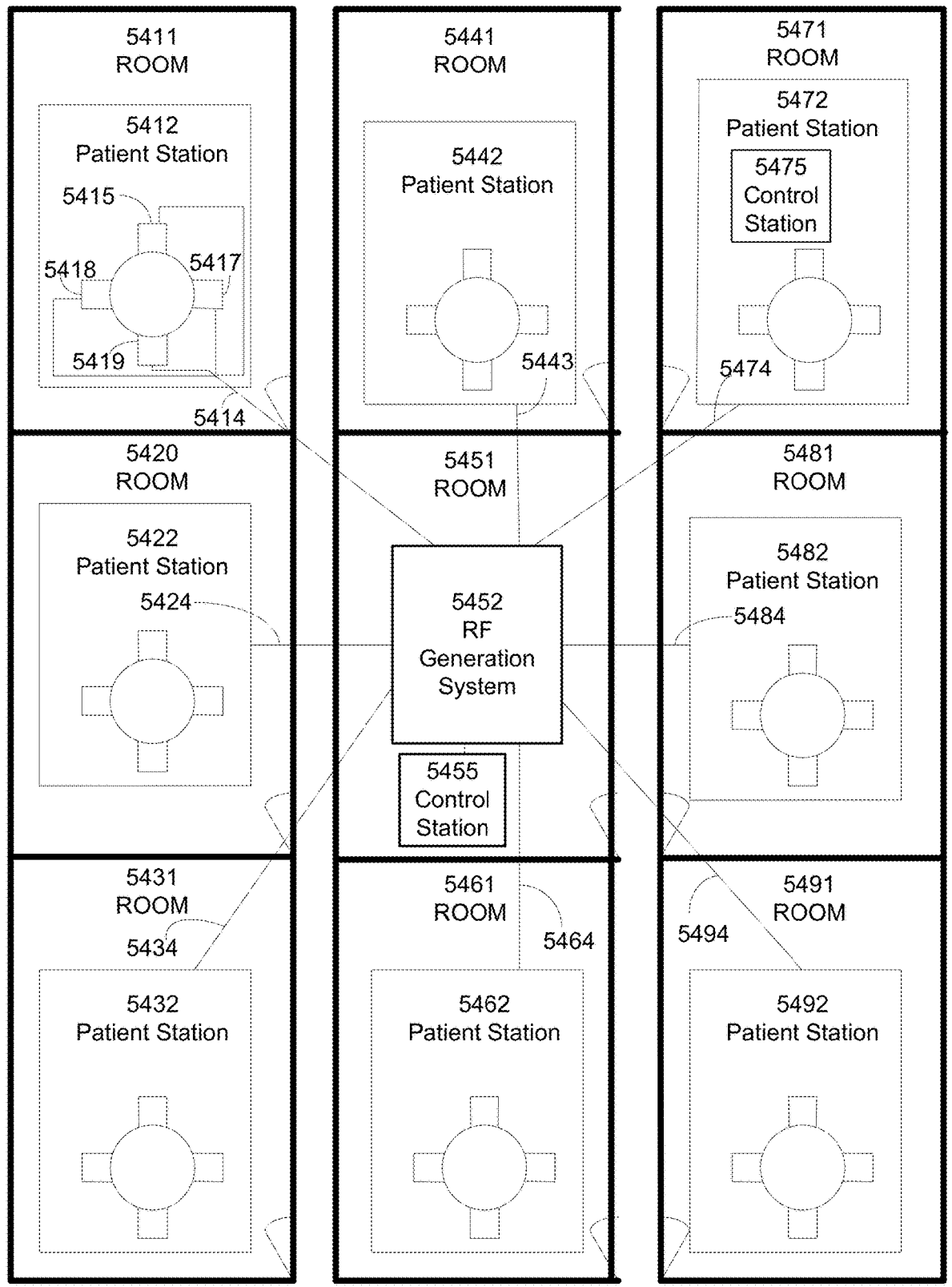
FIG. 49 is a block diagram of an exemplary multiple patient station radiation system in accordance with one embodiment.

FIG. 49 is a block diagram of an exemplary multiple patient station radiation system 5400 in accordance with one embodiment. Multiple patient station radiation system 5400 includes multiple patient stations (5412, 5422, 5432, 5442, 5462, 5472, 5482, and 5492). In one embodiment, a patient station includes a patient support (e.g., similar to support 105, 595, etc.) and multiple accelerator systems (e.g., similar to accelerator systems in FIG. 1, 37, 38, etc.). The patient stations (5412, 5422, 5432, 5442, 5462, 5472, 5482, and 5492) can be located in separate rooms (5411, 5420, 5431, 5441, 5461, 5471, 5481, and 5491). In one embodiment, patient stations 5412, 5422, 5432, 5442, 5462, 5472, 5482, and 5492 can be located in a single room. Multiple patient station radiation system 5400 includes a RF generation system 5452 configured to supply RF signals (e.g., microwave, etc.) to the patient stations 5412, 5422, 5432, 5442, 5462, 5472, 5482, and 5492. In one embodiment, RF generation system 5452 is coupled to RF chains 5414, 5424, 5434, 5443, 5464, 5474, 5484, and 5494 which are coupled to the patient stations 5412, 5422, 5432, 5442, 5462, 5472, 5482, and 5492, respectively. In one exemplary implementation, waveguide 5414 supplies RF signals to accelerators 5415, 5417, 5418, and 5419.

Multiple patient station radiation system 5400 can also include a control station 5455 that is communicatively coupled to other components of multiple patient station radiation system 5400. Control station 5455 can provide direction/control of the other components, including directing operations in accordance with various radiation medical plans. In one embodiment, control station 5455 is considered a central control station configured to control multiple patient stations (e.g., 5412, 5431, 5441, etc.). Control station 5455 can provide various monitoring features. The control and monitoring can include tracking and directing various high intensity target operations. Directing replacement regimes, receiving alarms when a target is not replaced properly, and so on. In one embodiment, control station 5455 can include a computer system (e.g., including a processor, memory, display, input/output components, communication components, user interface, etc.). In one exemplary implementation, control station 5455 is similar to control system 120 in FIG. 1.

In one embodiment, various features and capabilities can be shared between the different components within a high intensity target system. In one exemplary implementation, capabilities of RF generation system 5452 and control station 5455 are shared with patient stations (5412, 5422, 5432, 5442, 5462, 5472, 5482, and 5492). Leveraging the control station and RF generation system capabilities across the multiple patient stations can be overall less expensive and facilitate cost savings compared to a system in which control station and RF generation systems capabilities are utilized by only one accelerator. In one exemplary implementation, RF generation system signals are time multiplexed to the different ones of the plurality of patient stations. In one exemplary implementation, control station capabilities can be time multiplexed to the different patient stations. In one exemplary implementation, control station capabilities can operate in parallel with the different patient stations.

It is appreciated that systems can have different configurations and different portions/components of a system can be shared between a plurality of stations or dedicated to a particular station. In one embodiment, an entire microwave generation system can be shared by multiple patient stations. In one embodiment, a first patient station and a second patient station can be configured to share a first subset of components included in the microwave generation system. The first patient station and a second patient station can be configured with respective dedicated/unshared second subsets of components included in the microwave generation system. The first subset of components can include a first type of component included in the microwave generation system and the second subset of component can include a second type of component included in the microwave generation system. In one embodiment, a modulator bank is shared, but each station has their own microwave source. In one exemplary implementation, a switching unit of a modulator is shared between multiple stations while pulse transformers and klystrons are dedicated to individual stations.

Figure 50:
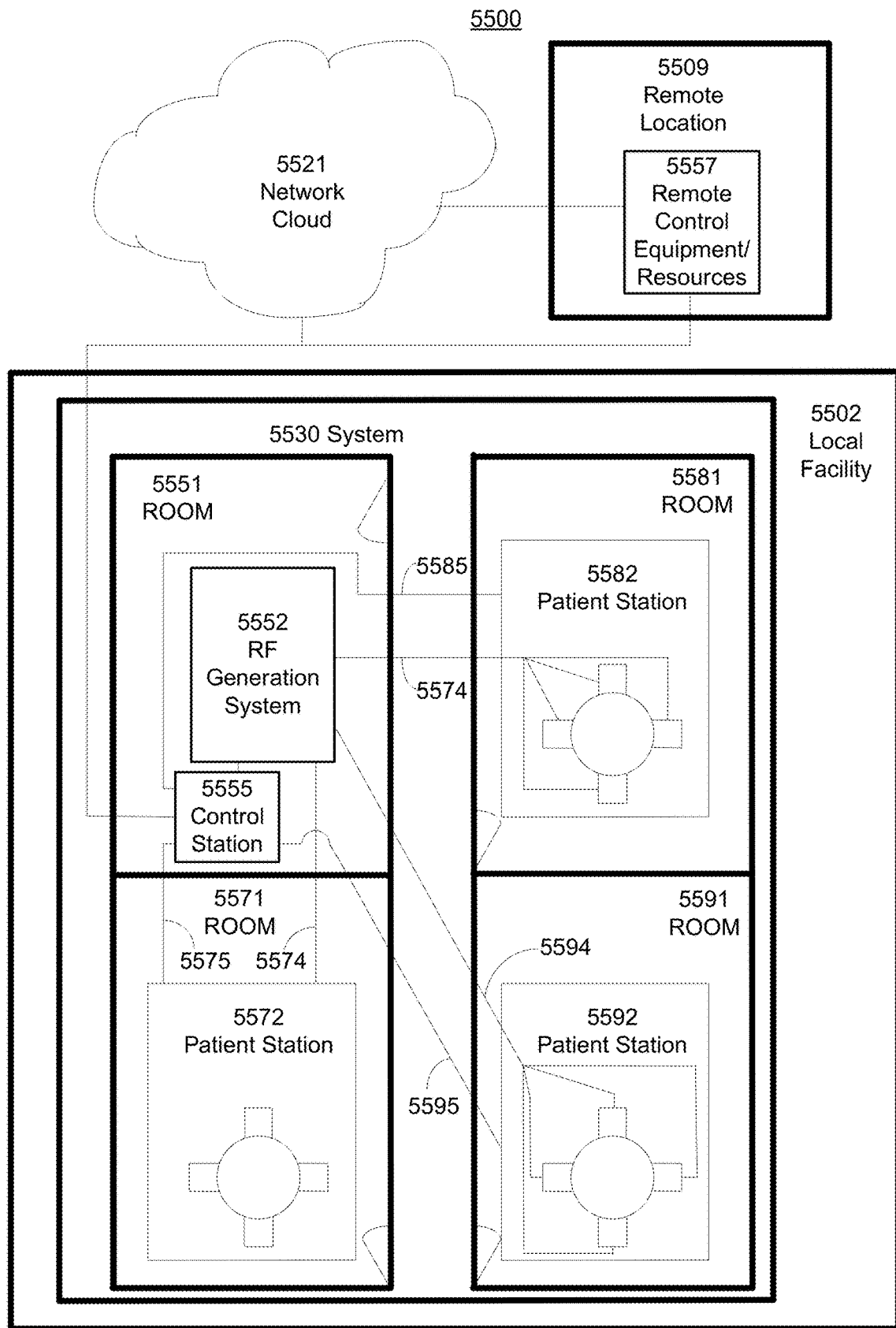
FIG. 50 is a block diagram of an exemplary remote resource system in accordance with one embodiment.

FIG. 50 is a block diagram of an exemplary remote resource system 5500 in accordance with one embodiment. Remote resource system 5500 includes local facility 5502, network 5521, and remote resources 5557. Local facility 5502 includes multiple patient stations 5572, 5582, and 5592 and RF generation system 5552 in separate rooms 5571, 5581, 5591, and 5551. Patient stations 5572, 5582, and 5592 are coupled to RF generation system (5552) via RF chains (e.g., 5584, 5594, etc.). In one embodiment, local facility 5502 is similar to multiple patient station radiation system 5400. In one embodiment, a patient station includes a patient support (e.g., similar to support 105, 595, etc.) and multiple accelerator systems (e.g., similar to accelerator systems in FIG. 1, 38, etc.). The patient stations (5572, 5582, and 5592) can be located in separate rooms (5571, 5581, and 5591). In one embodiment, patient stations 5572, 5582, and 5592 can be located in a single room. Room 5551 includes a RF generation system 5552 configured to supply microwave signals to the patient stations 5572, 5582, and 5592. In one embodiment, microwave generation system 5552 is coupled to RF chains 5574, 5584, and 5594, which are coupled to the patient stations 5572, 5582, and 5592. It is appreciated that a local facility can include various radiation system configurations (e.g., similar to radiation systems 100, 200, 5300, 5400, etc.).

Multiple patient station radiation system 5500 can also include a control station 5555 that is communicatively coupled to other components of multiple patient station radiation system 5500. In one embodiment, control station 5555 can include a computer system similar to control station 5455. In one embodiment control station 5555 is coupled to RF generation system 5552 and stations 5572, 5582, and 5592. Control station 5555 can provide direction to/control of the other components, including directing operations in accordance with various radiation medical plans. Control station 5555 can provide various monitoring features. The control and monitoring can include tracking and directing various high intensity target operations. In one exemplary implementation, Control station 5555 operations can include directing high intensity target replacement regimes, receiving alarms when a high intensity target is not replaced properly, and so on. Control station 5555 can utilize artificial intelligence resources, expert systems, machine learning, etc. Control station 5555 in local facility 5505 (e.g., a medical facility, a specialized treatment facility, a hospital, a doctor's office, etc.) can also communicate with network 5521 and remote resources 5557 in remote location 5509 (e.g., another medical facility, radiation system equipment manufacture/service, high intensity target supplier, etc.). In one embodiment, network 5521 includes various cloud resources that control station 5555 and remote resources 5557 can utilize and leverage.

In some embodiments, a high intensity target is compatible with precision controllability of the radiation beam. In some embodiments, a high intensity target facilitates generation and control of a relatively small diameter or circumference radiation beam. In some embodiments, radiation generation control facilitates ultra-high radiation dose rates with high fidelity delivery. The systems and methods can be compatible with pulse width modulation and timing control resolution is configured to facilitate delivery fidelity approaching intra-pulse and micro-bunch levels (e.g., corresponding to individual bunches per radio frequency cycle in a pulse width, etc.). The radio frequency can be in the microwave range. The systems and methods are also compatible with multiple field treatment approaches and can enable dose delivery for each fraction/field to be effectively controlled. In one embodiment, a high intensity target system can be implemented in systems running at beam power levels greater than 1.5 kW.

Thus, the presented systems and methods facilitate efficient and effective radiation beam generation. In some embodiments, a high intensity target system and method enables improved performance at higher energy levels over limited traditional Xray target approaches. The configuration of a high intensity target and adjustment of particle impact locations enables changes and improvements over conventional approaches, including operating at higher energy, dissipating great heat emission, and so on. In some embodiments, X-ray fluences can be increased by at least an order of magnitude over conventional levels. In some embodiments, a radiation system including a high intensity target produces intrinsic beam fluences with comparable or better spectral quality as those produced by a conventional Xray target. A high intensity target configuration can also facilitate better resolution and decreased treatment spot sizes. In some embodiments, a radiation system comprising a high intensity target configuration facilitates small focal spots for new and current treatments. The high intensity target system configuration can facilitate sharper edge definition during treatment.

It is appreciated that high intensity target configurations can be utilized in applications other than medical radiation applications. In some embodiments, high intensity target configurations can be utilized in various applications (e.g., medical, industrial, security, etc.). The high intensity target configuration can facilitate improved (e.g., faster, better image resolution, etc.) scanning of enclosed containers (e.g., packages, baggage, cargo scanning, etc.)

In one embodiment, a high intensity target approach is based on heat transmission characteristics, unlike conventional approaches. Conventional improvements to a solid Xray target are usually difficult to employ and do not typically offer much improvement in heat dissipation. While some traditional approaches may include a moving target that is not readily replaceable (e.g., Xray tube targets, etc.), the movement and characteristics of the target are not sufficient to disseminate heat at rates used in FLASH treatments. In addition, use of rotating targets in traditional diagnostics (e.g., Xray tubes targets, targets that are angled with X-rays emitted out an orthogonal side, particles impact and X-rays emitted from same side of the target, etc.) are very different from high energy targets used for treatment therapy (e.g., transmission target, particles impact one side of the target material and X-rays are emitted from an opposite side of the target material, etc.) Traditional approaches using free flowing liquid Xray jet streams can result in reduced and inconsistent radiation generation.

Presented high intensity target systems and methods can help overcome barriers for developing photon flash treatments, including limitations on dose delivery capabilities of conventional photon radiotherapy systems. High intensity target system dose delivery is considerably improved and allows for Flash treatments. Overcoming conventional barriers enables realization of multiple and significant advantages associated with x-ray photons. Photons can reach deep seated tumors at far lower energies than are required for electrons and ions (e.g., <10 MeV for photons vs>>100 MeV for electrons and ions, etc.). Photons can be emitted almost isotropically. In one embodiment, no raster scanning is needed. In one exemplary implementation, a 10 MeV Photon Flash system can fit into existing bunkers. In one embodiment, a high intensity target system can use mostly off-the shelf commercially available components. In one embodiment, a high intensity target system is considerably more economically than conventional systems. Significantly, x-ray sources in high intensity target systems can be inexpensive and compact enough to allow for multiple simultaneous beams from different angles. Delivering multiple simultaneous beams facilitates combination of the benefits from IMRT or arc therapy with the FLASH effect.

Some portions of the detailed descriptions are presented in terms of procedures, logic blocks, processing, and other symbolic representations of operations on data bits within a computer memory. These descriptions and representations are the means generally used by those skilled in data processing arts to effectively convey the substance of their work to others skilled in the art. A procedure, logic block, process, etc., is here, and generally, conceived to be a self-consistent sequence of steps or instructions leading to a desired result. The steps include physical manipulations of physical quantities. Usually, though not necessarily, these quantities take the form of electrical, magnetic, optical, or quantum signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are associated with the appropriate physical quantities and are merely convenient labels applied to these quantities. Unless specifically stated otherwise as apparent from the following discussions, it is appreciated that throughout the present application, discussions utilizing terms such as "processing", "computing", "calculating", "determining", "displaying" or the like, refer to the action and processes of a computer system, or similar processing device (e.g., an electrical, optical or quantum computing device) that manipulates and transforms data represented as physical (e.g., electronic) quantities. The terms refer to actions and processes of the processing devices that manipulate or transform physical quantities within a computer system's component (e.g., registers, memories, other such information storage, transmission or display devices, etc.) into other data similarly represented as physical quantities within other components.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as suited to the particular use contemplated. It is intended that the scope of the invention be defined by the Claims appended hereto and their equivalents. The listing of steps within method claims do not imply any particular order to performing the steps, unless explicitly stated in the claim.

The invention claimed is:

1. A radiation generation component comprising:
 a high intensity target configured to produce Bremsstrahlung radiation with average dose rates of at least 40 greys per second (Gy/s) in response to impacts by charged particles as the high intensity target is moved laterally, the high intensity target including
  a first Bremsstrahlung radiation zone configured to generate radiation in response to impacts by a first set of charged particles included in a first set of pulses of an electron beam, a second Bremsstrahlung radiation zone configured to generate radiation in response to impacts by a second set of charged particles included in a second set of pulses of an electron beam, and a third zone located laterally between the first Bremsstrahlung radiation zone and the second Bremsstrahlung radiation zone, wherein the high intensity target has operating parameters used to determine operating limitations based on catastrophic failure mechanisms rather than fatigue failure mechanisms and the third zone is an air gap between the first Bremsstrahlung radiation zone and the second Bremsstrahlung radiation zone.

2. The radiation generation component of claim 1, wherein the high intensity target comprises a material with a melting temperature in a range of 800 C. to 3,700 C.

3. The radiation generation component of claim 1, further comprising:

an accelerator enclosure including an access drawer, the access drawer configured to open and close to load the high intensity target within the accelerator enclosure.

4. The radiation generation component of claim 1, wherein the high intensity target comprises an identification feature.

5. The radiation generation component of claim 1, wherein the third zone is configured to mitigate detrimental effects associated with the impacts of the first set of charged particles on the second Bremsstrahlung radiation zone, mitigation of the detrimental effects including preventing heat diffusion from the first Bremsstrahlung radiation zone reaching the second Bremsstrahlung radiation zone before the impacts of the second set of charged particles in the second Bremsstrahlung radiation zone.

6. The radiation generation component of claim 1, further comprising:

a plurality of high intensity targets, wherein the high intensity target is among the plurality of high intensity targets.

7. The radiation generation component of claim 1, wherein the high intensity target is a multilayer structure and at least two layers of the multilayer structure include different materials.

8. The radiation generation component of claim 1, wherein the high intensity target is a monolithic structure comprising at least 80 percent of one metal by atomic weight.

9. The radiation generation component of claim 1, wherein the high intensity target includes at least one of copper, tungsten, or steel.

10. A radiation generation component comprising:

a high intensity target configured to generate Bremsstrahlung radiation with average dose rates of at least 40 greys per second (Gy/s) in response to impacts by charged particles as the high intensity target is moved laterally, the high intensity target including a first Bremsstrahlung radiation zone configured to generate radiation in response to impacts by a first set of charged particles included in a first set of pulses of an electron beam, a second Bremsstrahlung radiation zone configured to generate radiation in response to impacts by a second set of charged particles included in a second set of pulses of an electron beam, and a third zone located laterally between the first Bremsstrahlung radiation zone and the second Bremsstrahlung radiation zone, wherein the high intensity target has operating parameters used to determine operating limitations based on catastrophic failure mechanisms rather than fatigue failure mechanisms, said Bremsstrahlung radiation corresponds to peak dose rates greater than 0.001 Greys per pulse (Gy/pulse), the high intensity target is configured to be compatible with a radiation generation system, the high intensity target is configured to be loaded in the radiation generation system in under 5 minutes and unloaded from the radiation generation system in under 5 minutes, and the third zone is configured to prevent heat dissipation from the first Bremsstrahlung radiation zone from reaching the second Bremsstrahlung radiation zone in less than 1 millisecond.

11. The radiation generation component of claim 1, wherein the high intensity target is configured to be compatible with a loading system of a radiation generation system.

12. The radiation generation component of claim 1, wherein the high intensity target has a surface area that is rectangular.

13. The radiation generation component of claim 1, wherein the high intensity target further includes a handle for adjustment of the high intensity target with respect to a holding system of the high intensity target.

* * * * *